US011110291B2

(12) United States Patent
Bloch et al.

(10) Patent No.: US 11,110,291 B2
(45) Date of Patent: Sep. 7, 2021

(54) ORAL TREATMENT DEVICE, SYSTEM AND METHOD

(71) Applicant: Colgate-Palmolive Company, New York, NY (US)

(72) Inventors: Brian Bloch, Hillsborough, NJ (US); Michael Lefebvre, Phoenix, AZ (US)

(73) Assignee: Colgate-Palmolive Company, New York, NY (US)

( * ) Notice: Subject to any disclaimer, the term of this patent is extended or adjusted under 35 U.S.C. 154(b) by 378 days.

(21) Appl. No.: 16/157,198

(22) Filed: Oct. 11, 2018

(65) Prior Publication Data

US 2020/0114166 A1   Apr. 16, 2020

(51) Int. Cl.
*A61N 5/06* (2006.01)
*A61C 19/06* (2006.01)
*A61C 1/08* (2006.01)

(52) U.S. Cl.
CPC ............ *A61N 5/0603* (2013.01); *A61C 1/088* (2013.01); *A61C 19/066* (2013.01); *A61N 5/062* (2013.01); *A61N 2005/0606* (2013.01); *A61N 2005/0654* (2013.01); *A61N 2005/0663* (2013.01)

(58) Field of Classification Search
CPC ... A61C 19/003; A61C 19/063; A61C 19/066; A61C 19/06; A61C 1/088; A61N 5/0603; A61N 5/0613; A61N 5/0652; A61N 5/062; A61N 2005/0606; A61N 2005/0643; A61N 2005/0654; H01R 13/2414
See application file for complete search history.

(56) References Cited

U.S. PATENT DOCUMENTS

| | | | |
|---|---|---|---|
| 5,316,473 | A | 5/1994 | Hare |
| 5,487,662 | A | 1/1996 | Kipke et al. |
| 6,616,447 | B1 | 9/2003 | Rizoiu et al. |
| 6,650,018 | B1 | 11/2003 | Zhao et al. |
| 6,893,259 | B1 | 5/2005 | Reizenson |

(Continued)

FOREIGN PATENT DOCUMENTS

| | | |
|---|---|---|
| CN | 102188294 | 9/2011 |
| CN | 204293299 | 4/2015 |

(Continued)

OTHER PUBLICATIONS

International Search Report and Written Opinion for PCT/US2016/067564 dated Mar. 16, 2017.

(Continued)

*Primary Examiner* — Jacqueline T Johanas
*Assistant Examiner* — Shannel Nicole Belk

(57) ABSTRACT

An oral treatment device that emits electromagnetic radiation onto surfaces of a user's teeth. The oral treatment device may include an intraoral mouthpiece and a handle extending therefrom, the handle containing the control circuitry required for operation of the device. The mouthpiece may include a lamp support structure, a lamp, a lens plate, and a guard component. The lamp may include an electromagnetic radiation source that includes a flexible sheet and a plurality of illumination elements located thereon. The illumination elements may be light emitting diodes printed with an electrically conductive. Additional electronic components such as a processor and a power source may also be included in the device.

25 Claims, 30 Drawing Sheets

(56) References Cited

U.S. PATENT DOCUMENTS

| | | | |
|---|---|---|---|
| 6,976,841 B1* | 12/2005 | Osterwalder | A61C 19/063 433/29 |
| 7,331,784 B2 | 2/2008 | Suzuki | |
| 7,572,124 B2 | 8/2009 | Cipolla et al. | |
| 7,645,137 B2 | 1/2010 | Wasyluch | |
| 7,802,988 B2 | 9/2010 | Yarborough | |
| 8,172,570 B2 | 5/2012 | Baughman | |
| 8,215,954 B2 | 7/2012 | Levine | |
| 8,241,035 B2 | 8/2012 | Jones et al. | |
| 8,591,227 B2 | 11/2013 | Levine | |
| 8,602,774 B2 | 12/2013 | Wasylucha | |
| 8,905,759 B2 | 12/2014 | De Sousa et al. | |
| 9,299,887 B2 | 3/2016 | Lowenthal et al. | |
| 9,492,257 B2 | 11/2016 | Jablow et al. | |
| 9,539,075 B2 | 1/2017 | Sanders et al. | |
| 9,636,198 B2 | 5/2017 | Kodama | |
| 9,889,315 B2 | 2/2018 | Demarest et al. | |
| 9,901,744 B2 | 2/2018 | Demarest et al. | |
| 9,913,992 B2 | 3/2018 | Demarest et al. | |
| 10,369,375 B2 | 8/2019 | Demarest et al. | |
| 10,716,652 B2 | 7/2020 | Stewart et al. | |
| 10,758,330 B2 | 9/2020 | Bloemen et al. | |
| 2004/0152051 A1 | 8/2004 | Craig | |
| 2005/0048444 A1 | 3/2005 | Creamer | |
| 2005/0064370 A1 | 3/2005 | Duret | |
| 2005/0153256 A1 | 7/2005 | Livolsi | |
| 2005/0186539 A1 | 8/2005 | McLean et al. | |
| 2005/0191913 A1* | 9/2005 | Farnworth | B33Y 80/00 439/862 |
| 2005/0202363 A1 | 9/2005 | Osterwalder | |
| 2005/0244792 A1 | 11/2005 | Verdi et al. | |
| 2005/0266370 A1 | 12/2005 | Suzuki | |
| 2006/0003284 A1 | 1/2006 | Sale et al. | |
| 2006/0019214 A1 | 1/2006 | Lawrence et al. | |
| 2006/0039874 A1 | 2/2006 | Wong | |
| 2006/0141422 A1 | 6/2006 | Philp et al. | |
| 2006/0172260 A1 | 8/2006 | Allred et al. | |
| 2006/0201520 A1 | 9/2006 | Christensen | |
| 2007/0003905 A1 | 1/2007 | Nguyen et al. | |
| 2007/0009856 A1 | 1/2007 | Jones et al. | |
| 2007/0054233 A1 | 3/2007 | Rizoiu et al. | |
| 2008/0032253 A1 | 2/2008 | Montgomery et al. | |
| 2008/0050693 A1 | 2/2008 | Fischer et al. | |
| 2008/0063999 A1 | 3/2008 | Osborn | |
| 2008/0233541 A1 | 9/2008 | De Vreese et al. | |
| 2009/0017422 A1 | 1/2009 | Creamer | |
| 2009/0155740 A1 | 6/2009 | Jensen et al. | |
| 2010/0136498 A1 | 6/2010 | Baughman | |
| 2010/0311007 A1 | 12/2010 | Eliyahov | |
| 2011/0076636 A1 | 3/2011 | Wolff et al. | |
| 2011/0104631 A1 | 5/2011 | Levine | |
| 2011/0104633 A1 | 5/2011 | Levine | |
| 2011/0266031 A1* | 11/2011 | Kim | H01R 13/2414 174/126.2 |
| 2012/0183919 A1 | 7/2012 | Levine | |
| 2012/0214122 A1 | 8/2012 | Dwyer et al. | |
| 2012/0295212 A1 | 11/2012 | Sakimura et al. | |
| 2013/0026504 A1 | 1/2013 | Marx et al. | |
| 2013/0029291 A1 | 1/2013 | Williams | |
| 2013/0045457 A1 | 2/2013 | Chetiar et al. | |
| 2013/0052613 A1 | 2/2013 | Chetiar et al. | |
| 2013/0175515 A1 | 7/2013 | Ray et al. | |
| 2013/0280671 A1* | 10/2013 | Brawn | A61N 5/0603 433/24 |
| 2014/0186789 A1 | 7/2014 | Valoir | |
| 2014/0227657 A1 | 8/2014 | Sanders | |
| 2014/0272770 A1* | 9/2014 | Hurley | A61C 5/90 433/29 |
| 2014/0355251 A1 | 12/2014 | Kahrs et al. | |
| 2015/0004556 A1 | 1/2015 | Jin | |
| 2015/0044628 A1 | 2/2015 | Flyash | |
| 2015/0132709 A1* | 5/2015 | Park | A61C 19/066 433/29 |
| 2015/0140502 A1 | 5/2015 | Brawn et al. | |
| 2015/0164618 A1 | 6/2015 | Heacock et al. | |
| 2015/0204490 A1 | 7/2015 | Zheng et al. | |
| 2015/0360606 A1 | 12/2015 | Thompson et al. | |
| 2016/0035924 A1 | 2/2016 | Oraw et al. | |
| 2016/0235511 A1* | 8/2016 | Kodama | A61C 19/06 |
| 2016/0271415 A1* | 9/2016 | Min | A61C 19/066 |
| 2016/0331487 A1 | 11/2016 | Newman et al. | |
| 2017/0080249 A1 | 3/2017 | Brawn et al. | |
| 2017/0172717 A1 | 6/2017 | Deng et al. | |
| 2017/0173353 A1* | 6/2017 | Demarest | A61C 19/063 |
| 2017/0173355 A1* | 6/2017 | Demarest | A61C 19/066 |
| 2017/0189149 A1 | 7/2017 | Golub et al. | |
| 2019/0000601 A1* | 1/2019 | Huang | A46B 13/023 |
| 2019/0388206 A1* | 12/2019 | Whitney | A61C 19/02 |
| 2019/0388208 A1* | 12/2019 | Whitney | A61C 19/02 |
| 2020/0093576 A1 | 3/2020 | Cinader et al. | |
| 2020/0112013 A1* | 4/2020 | Kramer | H01R 4/58 |
| 2020/0114166 A1* | 4/2020 | Bloch | A61N 5/062 |
| 2020/0261197 A1 | 8/2020 | Bakker-Van Der Kamp et al. | |

FOREIGN PATENT DOCUMENTS

| | | |
|---|---|---|
| DE | 202011104169 | 10/2011 |
| EP | 1741407 | 1/2007 |
| EP | 1054642 B1 | 5/2008 |
| EP | 2386264 | 11/2011 |
| EP | 2386264 A2 | 11/2011 |
| KR | 100773379 B1 | 11/2007 |
| KR | 200442332 | 10/2008 |
| KR | 101525123 B1 | 6/2015 |
| KR | 20170029050 | 3/2017 |
| RU | 2352321 | 4/2009 |
| WO | WO 2005/107637 | 11/2005 |
| WO | WO 2006/020128 A2 | 2/2006 |
| WO | 2010/098764 | 9/2010 |
| WO | WO 2010/098761 A1 | 9/2010 |
| WO | WO 2011/152585 A1 | 12/2011 |
| WO | WO 2011/159522 A1 | 12/2011 |
| WO | WO 2011/163220 A2 | 12/2011 |
| WO | WO 2013/093743 A1 | 6/2013 |
| WO | WO 2013/155366 | 10/2013 |

OTHER PUBLICATIONS

International Search Report and Written Opinion for PCT/US2016/067573 dated Jun. 13, 2017.

Barolet, Daniel, Light-Emitting Diodes (LEDs) in Dermatology, Seminars in Cutaneous Medicine and Surgery, 2008, vol. 27, pp. 227-238.

Belikov, A.V et al., "Study of the Dynamics of the Absorption Spectra of Human Tooth Enamel and Dentine under Heating and Ablation by Submillisecond Pulse Radiation of an Erbium Laser with a Generation Wavelength of 2.79 um," Biomedical Optics and Spectroscopy, 2010, vol. 109, No. 2, pp. 211-216.

Brodbelt, R.H.W. et al., "Translucency of Human Dental Enamel," Journal of Dental Research, Oct. 1981, 60(10): 1749-1753.

DeMoor, Roeland J.G. et al., "The Use of the KTP Laser, an Added Value for Tooth Bleaching," Journal of Oral Laser Applications, 2009, 9:219-226.

Elliott, Annabel Fenwick, "Teeth Whitening, Spot Zapping, Hair Taming and Even Wrinkle Erasing: So Could BLUE Technology be the Future of Beauty," May 31, 2015. Published online at http://www.dailymail.co.uk/femail/article-3099582/Teeth-whiteening-spot-zapping-hair-taming-wrinkle-erasing-BLUE-technology-future-beauty.html.

Hirmer, Marion et al., "Spectroscopic Study of Human Teeth and Blood from Visible to Terahertz Frequencies for Clinical Diagnosis of Dental Pulp Vitality," Journal of Infared Milli Terahz Waves, 2012, 33:366-375.

Joiner, Andrew et al., "Tooth Colour: A Review of the Literature," Journal of Dentistry, 2004 32:3-12.

Spitzer, D. et al., "The Absorption and Scattering of Light in Bovine and Human Dental Enamel," Calcif. Tiss. Research, 1975, 17:129-137.

(56) References Cited

OTHER PUBLICATIONS

Bosch, J.J., et al., "Optical Properties of Dentin," *Dentine and Dentine Reactions in the Oral Cavity*, 1987, Chapter 3, pp. 59-65.
Young, Nigel et al., "A Study of Hydrogen Peroxide Chemistry and Photochemistry in Tea Stain Solution with Relevance to Clinical Tooth Whitening," Journal of Dentistry, 2012, 408:e11-e16.
Partial International Search Report issued in International Application PCT/US2016/067573 dated Mar. 22, 2017.
Galiatsatos, 2007, "Ch. 50: Refractive Index, Stress-Optical Coefficient, and Optical Configuration Parameter of Polymers," Physical Properties of Polymers Handbook, by James E. Mark, pp. 823-853.

\* cited by examiner

ORAL TREATMENT DEVICE, SYSTEM AND METHOD

BACKGROUND

Tooth whitening is an increasingly popular treatment and dentists and patients alike are searching for techniques that are both convenient and comfortable while also being effective. Typically, to whiten a user's teeth a composition containing hydrogen peroxide is applied to the teeth and allowed to remain in contact with the teeth to be bleached for a period of time. Current systems are available that allow a user to apply radiation or light to the surfaces of the teeth that are pre-coated with the whitening composition to enhance the effectiveness of the whitening composition. However, currently available systems are bulky and rigid and undesirable for one or more reasons. Specifically, current systems do not emit radiation or light onto the user's pre-coated teeth uniformly and in a manner that effectively covers the entire tooth surface. Thus, a need exists for a tooth whitening system that is able to effectively emit radiation or light onto a user's teeth.

BRIEF SUMMARY

The present invention may be directed, in one aspect, to an oral treatment device that emits electromagnetic radiation onto surfaces of the user's teeth. In certain aspects, the electromagnetic radiation is emitted by an electromagnetic radiation source that is coupled to a lamp support structure of a mouthpiece. The electromagnetic radiation source may comprise a flexible circuit and a plurality of illumination elements located thereon. In some aspects, the electromagnetic radiation source may be a printed light emitting diode circuit. The oral treatment device may include a mouthpiece or other structure that supports the electromagnetic radiation source as well as a handle. The handle may contain additional electronic components such as a processor and a power source.

In one aspect, the invention may be an oral treatment device comprising: an intraoral mouthpiece having a dental arch midline plane and comprising: a lamp support structure comprising: a curved support plate; a first relief element formed in the curved support plate on a first side of the dental arch midline plane that increases flexibility of a first end portion of the curved support plate relative to a central portion of the curved support plate; and a second relief element formed in the curved support plate on a second side of the dental arch midline plane that increases flexibility of a second end portion of the curved support plate relative to the central portion of the curved support plate; and a lamp mounted to the lamp support structure and configured to emit electromagnetic radiation onto oral surfaces when the intraoral mouthpiece is positioned within a mouth of a user and activated.

In another aspect, the invention may be an oral treatment device comprising: a control circuit that comprises, in operable coupling, a power source, a first compressible electrical contact having a first electrical charge, and a second compressible electrical contact having a second electrical charge that is opposite the first electrical charge; an intraoral mouthpiece comprising: a lamp comprising a flexible sheet body having first and second electrical contacts on a rear surface of the flexible sheet body, the lamp configured to generate and emit electromagnetic radiation from a front surface of the lamp; and wherein the lamp is mounted within the oral treatment device so that the first and second electrical contacts of the lamp are aligned and pressed into contact with the first and second compressible electrical contacts of the control circuit, respectively.

In yet another aspect, the invention may be an oral care treatment device comprising: an intraoral mouthpiece having a dental arch midline plane and comprising: a lamp support structure comprising: a lamp support surface having a concave curvature; at least one upper overhang structure defining an upper slot having an open bottom between the upper overhang structure and the lamp support surface; at least one lower overhang structure defining a lower slot having an open top between the upper overhang structure and the lamp support surface; and a lamp comprising a flexible sheet body and configured to generate and emit electromagnetic radiation; and the lamp is mounted to the lamp support structure so that a top edge of the flexible sheet body nests within the upper slot and a bottom edge of the flexible sheet body nests within the lower slot, the flexible sheet body being maintained in a flexed state along the lamp support surface due, at least in part, to contact with the upper and lower overhang structures.

In still another aspect, the invention may be a method of forming an intraoral mouthpiece of an oral treatment system, the method comprising: a) providing a lamp support structure comprising: a lamp support surface having a concave curvature; at least one upper overhang structure defining an upper slot having an open bottom between the upper overhang structure and the lamp support surface; and at least one lower overhang structure defining a lower slot having an open top between the upper overhang structure and the lamp support surface; and b) mounting a lamp to the lamp support structure by inserting a top edge of a flexible sheet body of the lamp into the upper slot and a bottom edge of the flexible sheet body into the lower slot, the flexible sheet body being maintained in a flexed state along the lamp support surface due, at least in part, to contact with the upper and lower overhang structures.

In a further aspect, the invention may be an oral treatment device comprising: a control circuit that comprises, in operable coupling, a power source, a first electrical contact having a first electrical charge, and a second electrical contact having a second electrical charge that is opposite the first electrical charge; an intraoral mouthpiece having a dental arch midline plane and comprising: a lamp comprising a sheet body and a plurality of illumination zones, each of the illumination zones comprising a plurality of light emitters embedded within the sheet body and disposed within an electrically conductive ink, the plurality of illumination zones electrically isolated from one another; the lamp further comprising a first electrical contact and a second electrical contact, each of the plurality of illumination zones in electrical coupling with the first and second electrical contacts of the lamp; and the first and second electrical contacts of the lamp electrically coupled to the first and second electrical contacts of the control circuit respectively so that each of the plurality of illumination zones receives power from the power source and emits electromagnetic radiation from a front surface of the flexible sheet body.

In a still further aspect, the invention may be an oral treatment system comprising: an oral treatment device comprising: a control circuit comprising a power source; an intraoral mouthpiece comprising: a lamp operably coupled to the power source, the lamp comprising a sheet body and a plurality of light emitters embedded within the sheet body, the sheet body comprising a lamp lens plate forming a front surface of the flexible sheet body, the lamp lens plate formed of a material having a first refractive index; and a cover lens plate overlying the front surface of the sheet body of the lamp and being adjacent the lamp lens plate so that a lamp-cover interface is formed between the lamp lens plate and the cover lens plate, the lamp lens plate being formed of a material having a second refractive index that is less that the first refractive index; and wherein upon the lamp being activated, light generated by the plurality of light emitters passes though the lamp lens plate and the cover lens plate prior to exiting the oral treatment device.

In another aspect, the invention may be a method of whitening facial surfaces of teeth comprising: a) applying a teeth whitening material having a third refractive index to at least one of the facial surfaces of the teeth or a front surface of a cover lens plate of an oral treatment device, the oral treatment device comprising: a lamp comprising one or more light emitters and a lamp lens plate, the lamp lens plate formed of a material having a first refractive index; and the cover lens plate overlying the lamp lens plate so that a lamp-cover interface is formed between the lamp lens plate and the cover lens plate, the lamp lens plate being formed of a material having a second refractive index that is less that the first refractive index; b) positioning the oral treatment device adjacent the facial surfaces of the teeth so that the teeth whitening material contacts the teeth and the front surface of the cover lens plate, the third refractive index being less than the second refractive index; and c) activating the lamp so that the one or more light emitters generate light that passes through the lamp lens plate, the cover lens plate, and the oral care material.

In yet another aspect, the invention may be an oral treatment device comprising: a control circuit that comprises, in operable coupling, a power source, a first electrical contact having a first electrical charge, and a second electrical contact having a second electrical charge that is opposite the first electrical charge; an intraoral mouthpiece comprising: a lamp comprising a flexible sheet body and a plurality of light emitters, the flexible sheet body having first and second electrical contacts on a rear surface of the flexible sheet body; a lamp support surface having a concave curvature, the lamp mounted to the lamp support surface; a curved cover lens plate overlying the lamp, the lamp positioned between the curved cover lens plate and the lamp support surface, the cover lens plate comprising one or more protuberances extending from a convex rear surface of the curved cover lens plate that are aligned with the first and second electrical contacts of the lamp and press the flexible sheet body of the lamp against the first and second electrical contacts.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION

Figure 1:
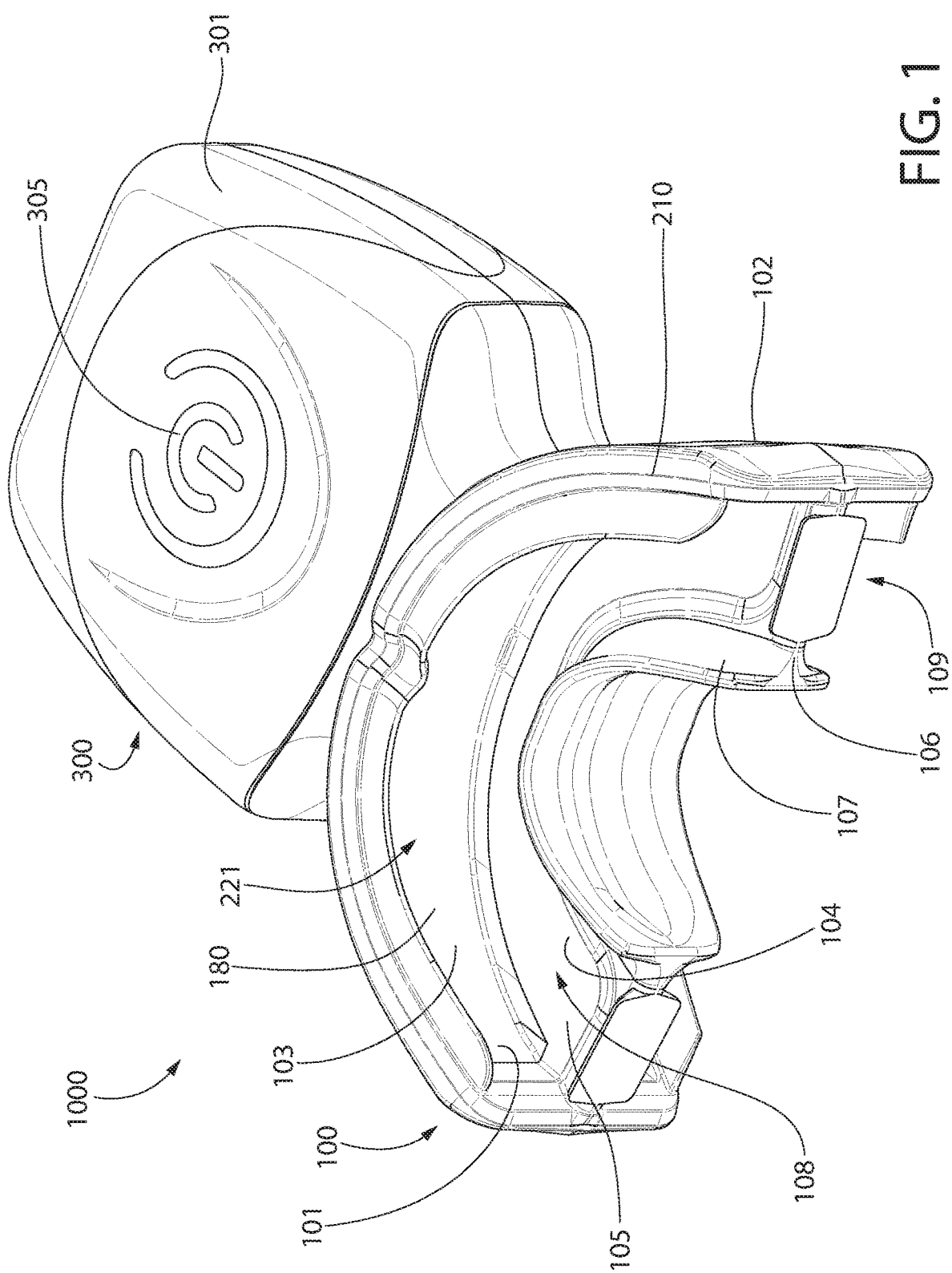
FIG. 1 is top front perspective view of an oral treatment device in accordance with an embodiment of the present invention.
Figure 2:
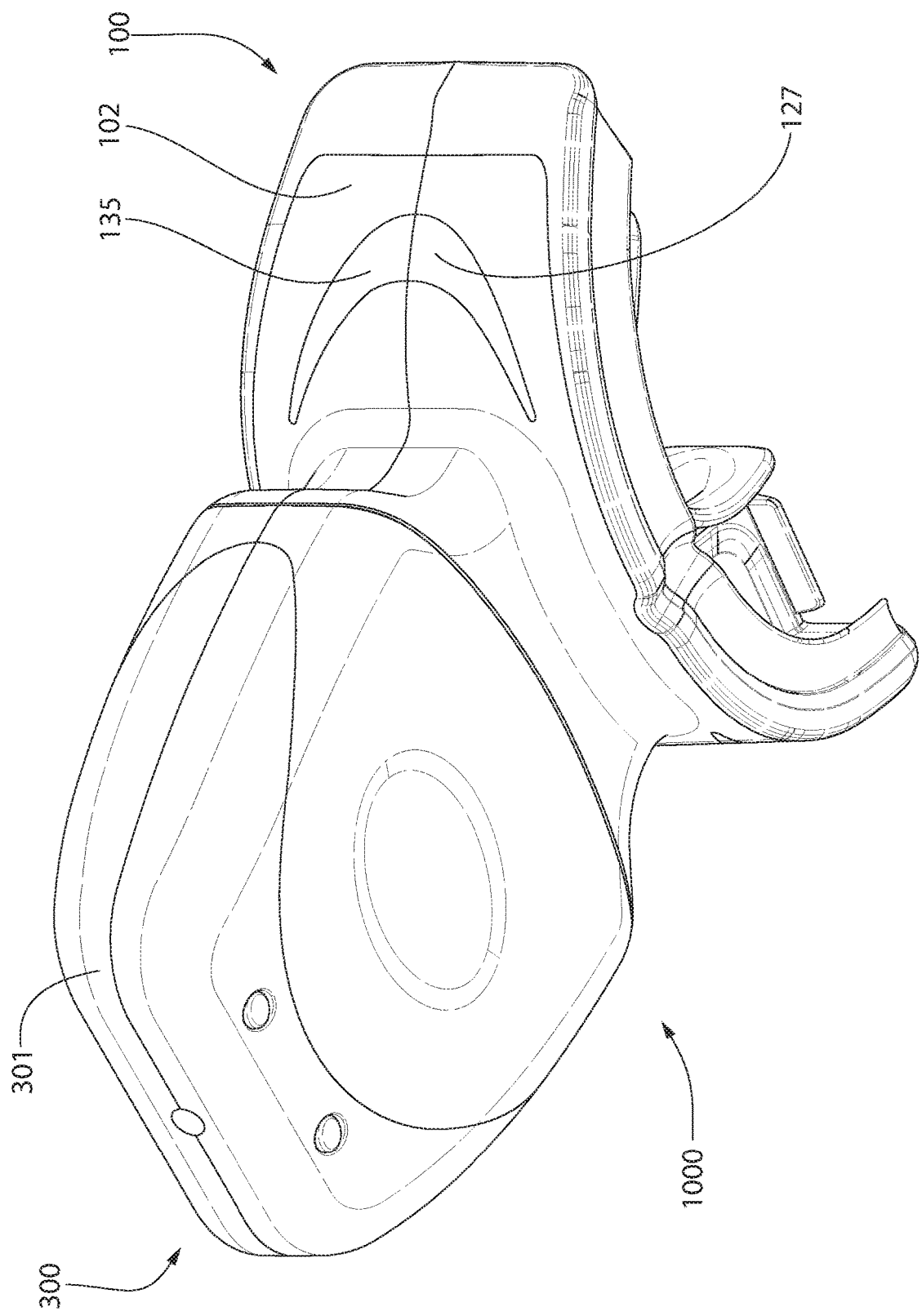
FIG. 2 is a bottom rear perspective view of the oral treatment device of FIG. 1.

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

Referring to FIGS. 1-5 concurrently, an oral treatment device 1000 will be described in accordance with an embodiment of the present invention. It is known in teeth whitening systems that a more effective whitening result can be achieved by applying a tooth whitening material to a user's teeth and then emitting light or electromagnetic radiation onto the teeth with the tooth whitening material pre-applied thereon in order to activate the tooth whitening material. Thus, the oral treatment device 1000 is one such device that is configured to emit electromagnetic radiation onto oral surfaces when the oral treatment device 1000, or portions thereof, is positioned within a mouth of a user and activated.

The oral treatment device 1000 generally comprises an intraoral mouthpiece (hereinafter, "the mouthpiece") 100 and a handle 300. The mouthpiece 100 comprises a concave front surface 101 from which the electromagnetic radiation is emitted onto the user's teeth during use and a convex rear surface 102. The handle 300 extends from the convex rear surface 102. Thus, the handle 300 extends from the mouthpiece 100 in a direction generally opposite the direction in which electromagnetic radiation/light is emitted from the mouthpiece 100. The handle 300 comprises a housing 301 that houses a control circuit 350 (see FIGS. 6A and 6B) of the oral treatment device 1000. The control circuit 350 and its positioning inside the housing 301 of the handle 300 will be described in greater detail below.

In the exemplified embodiment, the handle 300 comprises an actuator 305 (i.e., a power button) for activating the control circuit 350 for operation of the oral treatment device 100. Specifically, actuation of the actuator 305 will power the oral treatment device 1000 on so that power is transmitted from a power source to an electromagnetic radiation source so that the electromagnetic radiation source can emit the electromagnetic radiation onto the user's teeth as described herein. The oral treatment device 100 may power off automatically after a predetermined period of time, and/or the oral treatment device 100 may power off upon a second actuation of the actuator 305. In the exemplified embodiment, the actuator 305 is a depressible button, but the invention is not to be so limited and other types of actuators may be used. Specifically, the actuator 305 can be any type of device that upon actuation powers on and/or off one or more of the electrical components stored within the housing 301. For example, the actuator 305 can be a slide switch, a touch pad, a knob, a capacitive sensor, or any other component that upon actuation causes the oral treatment device 1000 to function as described herein. The actuator 305 may be operably coupled to a processor so that upon depressing or otherwise actuating the actuator 305, the processor initiates operation of the oral treatment device 1000 (i.e., powers on the electromagnetic radiation source) as described in more detail below.

The mouthpiece 100 (which, as discussed below, may be formed by a plurality of components) generally comprises an arch-shaped wall 103 from which the electromagnetic radiation (i.e., light) is emitted and a bite platform (or bite plate) 104 extending horizontally from the arch-shaped wall 103. The arch-shaped wall 103 may have a curvature that generally corresponds to the arch of the human dentiture. The mouthpiece 100 is designed to emit electromagnetic radiation both above and below the bite platform 104. Thus, the arch-shaped wall 103 forms a light emitting surface of the mouthpiece 100. The mouthpiece 100 may include a plurality of illumination zones (described in more detail below) so that at least one of the illumination zones is located above the bite platform 104 and at least one of the illumination zones is located below the bite platform 104.

In the exemplified embodiment, the arch-shaped wall 103 has a concave curvature and it is configured to emit electromagnetic radiation simultaneously onto the user's maxillary and mandibular teeth (and more specifically onto the facial surfaces of those teeth). Of course, in other embodiments the mouthpiece 100 may be modified so that it only emits electromagnetic radiation onto one of the user's maxillary or mandibular teeth at a time, but not both simultaneously. In the exemplified embodiment, the electromagnetic radiation is emitted by a lamp having a flexible sheet body, the details of which will be described in greater detail below with specific reference to FIGS. 11-15. In other embodiments, however, the light emitted by the mouthpiece 100 may be generated with other light sources that are either embedded in the arch-shaped wall 103 and/or transmitted to the light emitting surface of the mouthpiece 100 using light piping or other suitable techniques. As will be discussed in greater detail below, the light emitting surface of the mouthpiece 100 is designed to be positioned close to and optimally oriented relative to the user's maxillary and mandibular teeth when the oral treatment device 100 is being used.

The bite platform 104 comprises a horizontal portion 105 that extends horizontally from the arched wall 103 to a distal end 106 and a vertical portion 107 that extends both upwardly and downwardly from the horizontal portion 105 at the distal end 106. Thus, a first channel 108 is formed by the arched wall 103 and the bite platform 104, and specifically the horizontal portion 105 and the portion of the vertical portion 107 that extends upwardly from the horizontal portion 105. Similarly, a second channel 109 is formed by the arched wall 103 and the bite platform 104, and specifically the horizontal portion 105 and the portion of the vertical portion 107 that extends downwardly from the horizontal portion 105. The first and second channels 108, 109 are configured to receive a user's upper (maxillary) and lower (mandibular) teeth, respectively, during a tooth whitening session. The first and second channels 108, 109 may also receive a tooth whitening or treatment material prior to inserting the mouthpiece 100 into a user's oral cavity.

Figure 3:
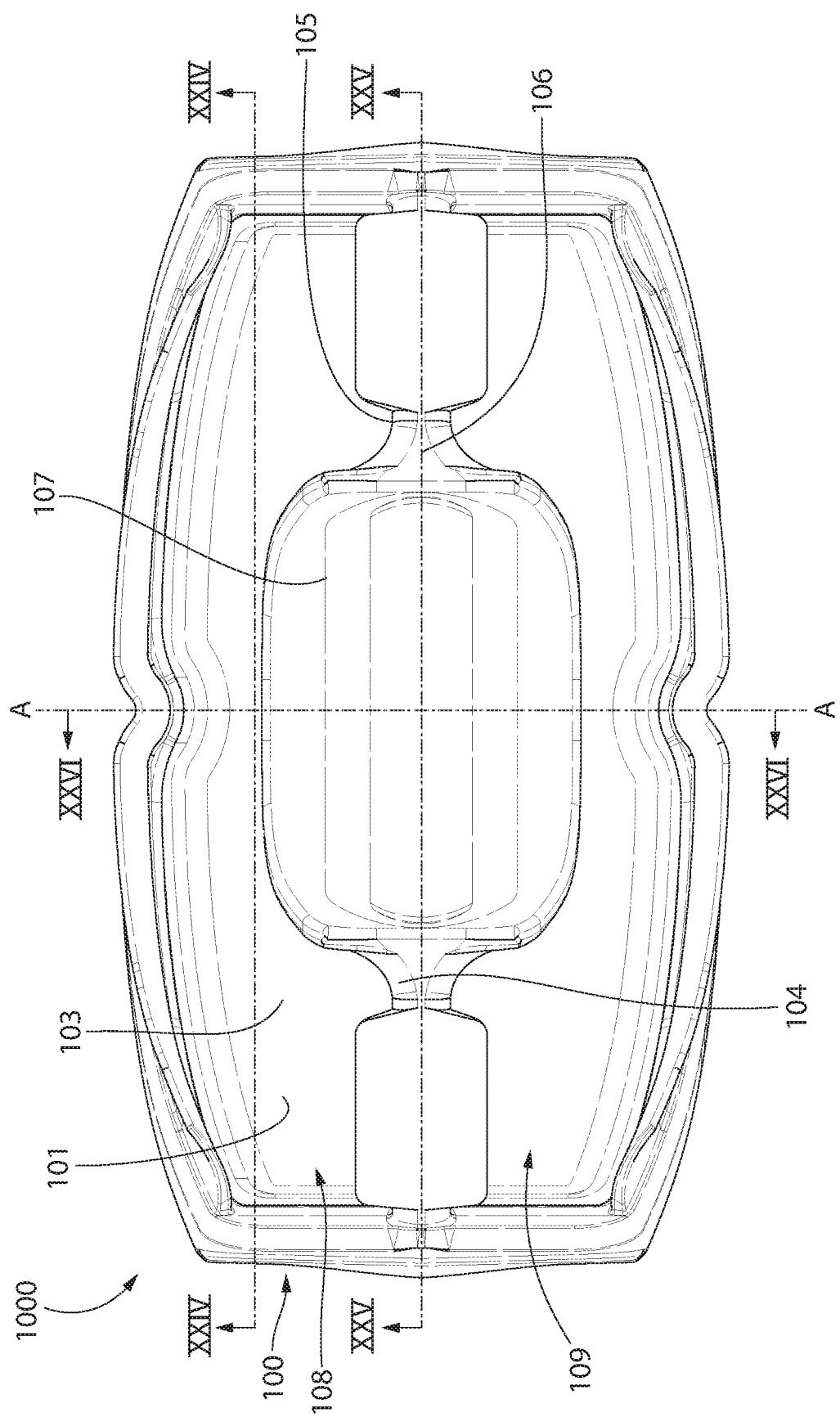
FIG. 3 is a front view of the oral treatment device of FIG. 1.
Figure 4:
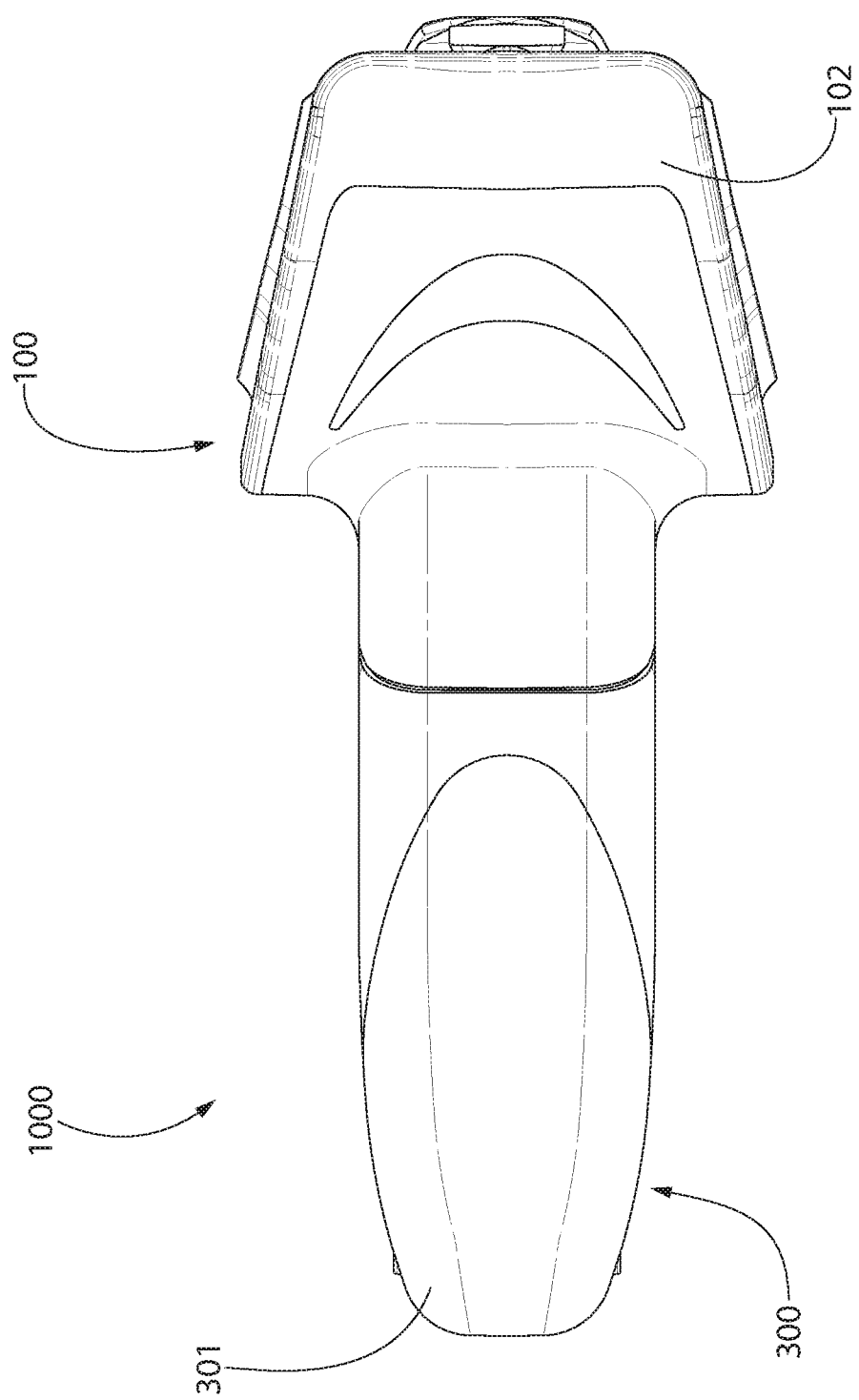
FIG. 4 is a side view of the oral treatment device of FIG. 1.
Figure 5:
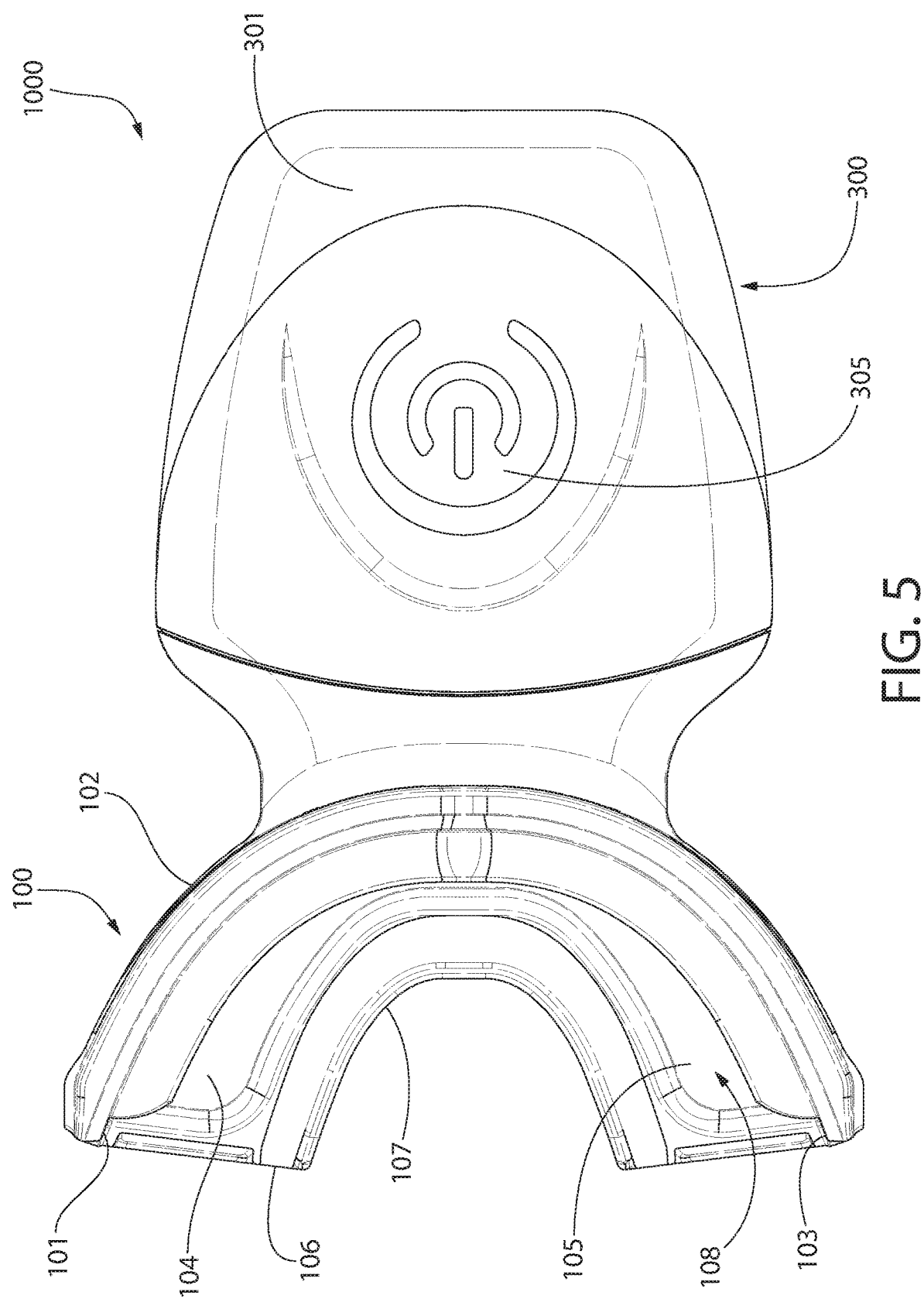
FIG. 5 is a top view of the oral treatment device of FIG. 1.

The mouthpiece 100 comprises a dental arch midline plane A-A illustrated in FIG. 3. The dental arch midline plane A-A is a plane that is located centrally between the two side ends of the mouthpiece 100 that intersects the upper and lower ends of the mouthpiece 100 and is perpendicular to an arcuate axis upon which the arched wall 103 extends. The dental arch midline plane A-A will be referenced later for purposes of providing a reference location along the mouthpiece 100 and components thereof.

During use, the mouthpiece 100 is inserted into a user's mouth such that the bite platform 104 is trapped or sandwiched between the user's maxillary and mandibular teeth. When so positioned, the upper portion of the light emitting surface (which is formed by the arch-shaped wall 103 of the mouthpiece 100) that is adjacent to the facial surfaces of the user's maxillary teeth has a curvature such that the upper portion of the light emitting surface generally corresponds to at least the anterior portion of the arch of the maxillary teeth. Similarly, the lower portion of the light emitting surface (which is formed by the arch-shaped wall 103 of the mouthpiece 100) that is adjacent the facial surfaces of the user's mandibular teeth has a curvature such that the lower portion of the light emitting surface generally corresponds to at least the anterior portion of the arch of the mandibular teeth.

It should be noted, however, that in certain embodiments of the invention, the mouthpiece 100 may be designed such that the bite platform 104 is omitted. In one such embodiment, the upper and lower light emitting surfaces may be maintained as separate and distinct light emitting areas, each of which emits light only onto the facial surfaces of the maxillary teeth and the facial surfaces of the mandibular teeth, respectively. In another such embodiment, the upper and lower light emitting surfaces may be merged into a single light emitting area that emits light onto the facial surfaces of both the maxillary and mandibular teeth. In another embodiment, the bite platform 104 may be omitted and only a single light emitting surface may be provided that emits light only onto the facial surfaces of the maxillary teeth or only onto the facial surfaces of the mandibular teeth at any given time. In still another embodiment, the bite platform 104 can be included and only one of the upper or lower light emitting surfaces may be provided.

In certain embodiments, the mouthpiece 101 (including all of the components thereof that come into contact with the oral cavity) may be formed of a biocompatible material, such as a food grade polymer. Suitable biocompatible materials include, without limitation, polyethylene terephthalate (PET), polypropylene (PP), polyethylene naphthalate (PEN), polyethylene (PE), silicone, ethylene propylene diene monomer (EPDM), and other plastics. Of course, the invention is not to be so limited in all embodiments and other materials are possible for construction of the mouthpiece 100, and various components thereof. In certain embodiments, the mouthpiece 100, or at least portions thereof, may be formed of an elastomeric material. The specific materials of some of the components of the mouthpiece 100 and the housing 300 will be described in greater detail below.

Figure 6A:
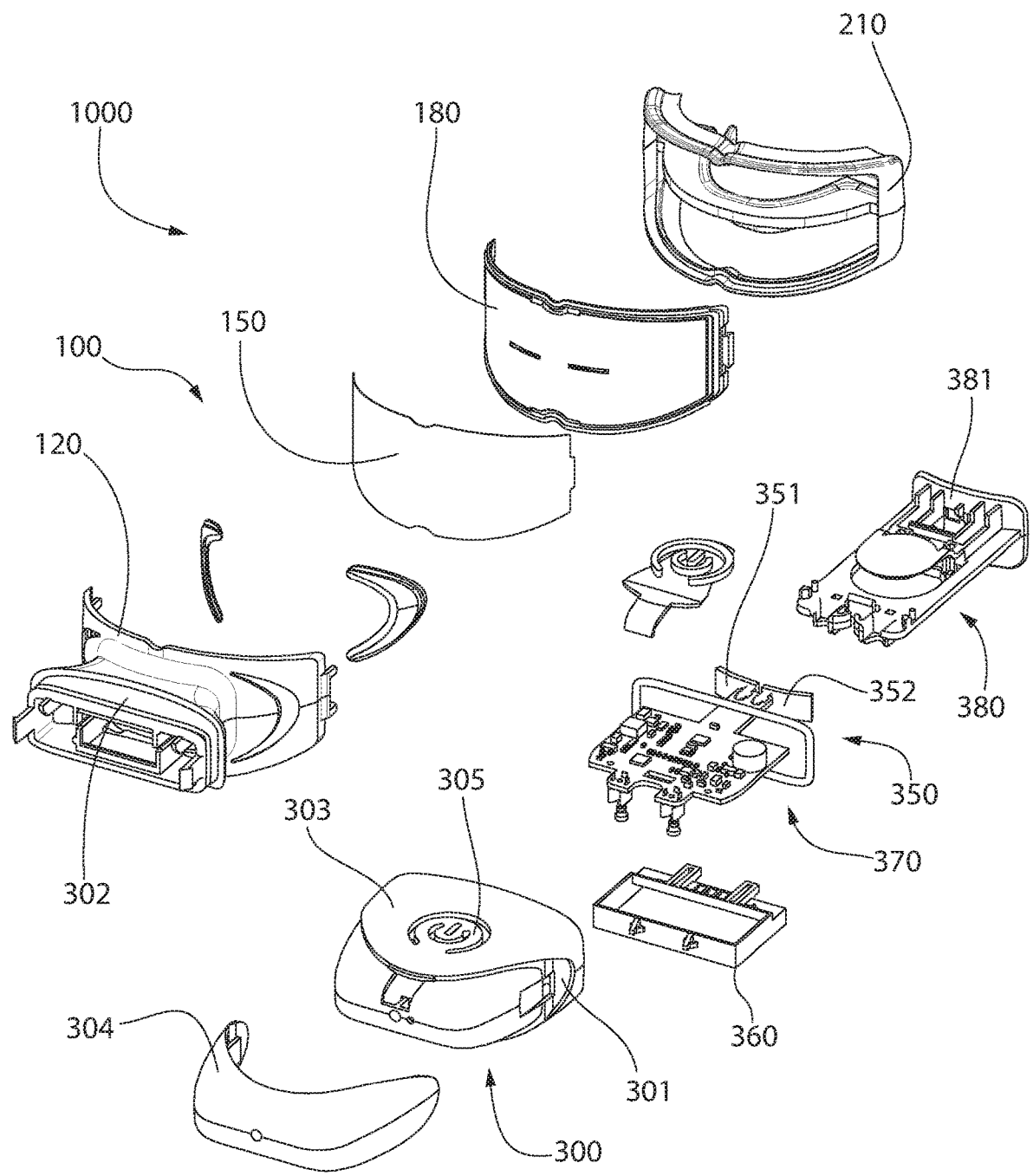
FIGS. 6A and 6B are perspective exploded views of the oral treatment device of FIG. 1.
Figure 6B:
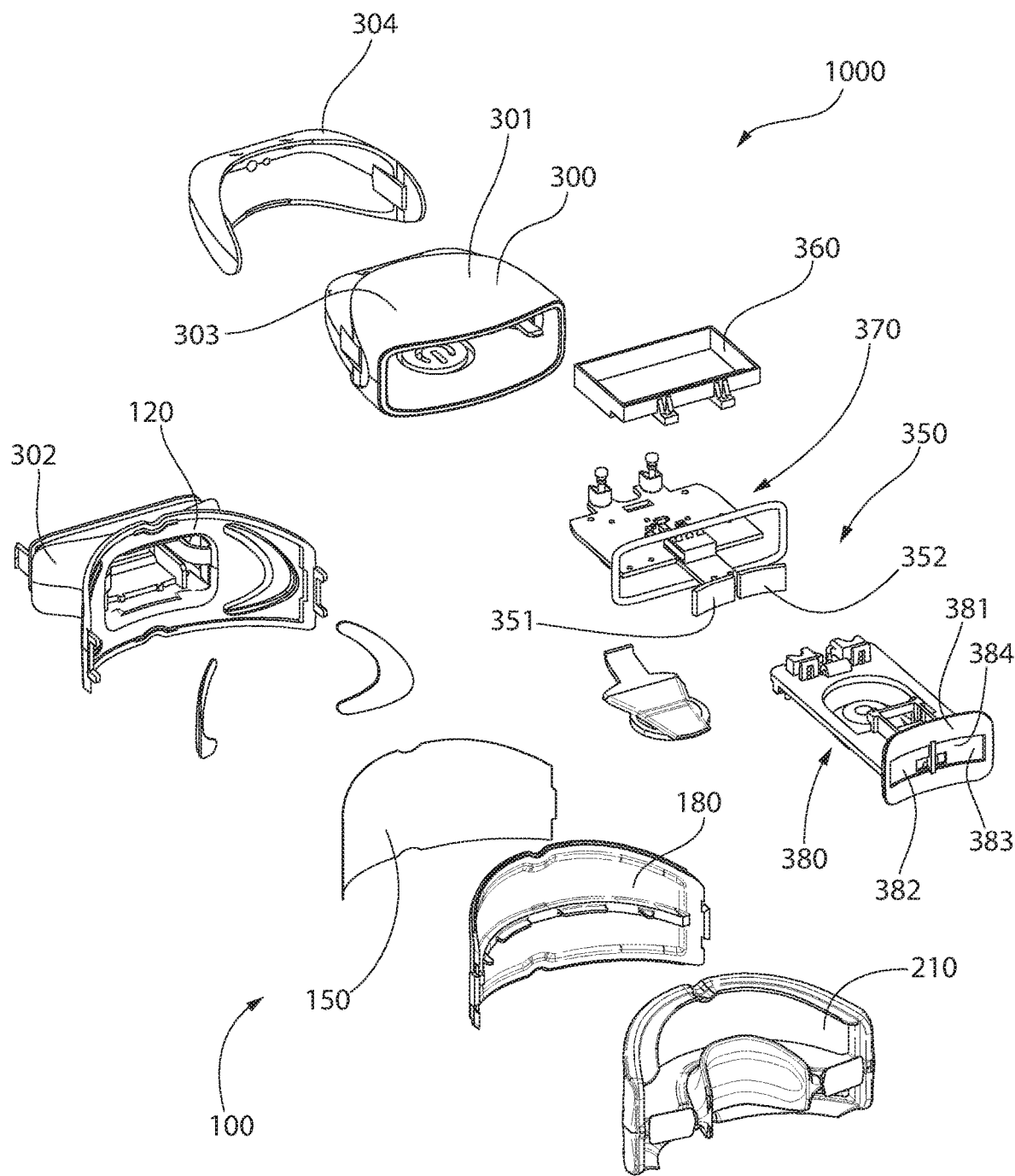

Referring to FIGS. 6A and 6B, the components of the oral treatment device 1000 will be mentioned and briefly described, with a more detailed description of some of the components being provided in the figures and description that follow. The mouthpiece 100 of the oral treatment device 1000 generally comprises a lamp support structure 120, a lamp 150, a lens plate or cover lens plate 180, and a guard component 210. Also illustrated in these exploded views are the handle 300 and the control circuit 350 that is housed within the housing 301 of the handle 300. When fully assembled, the lamp 150 is coupled to the lamp support structure 120 and then the lens plate 180 is coupled to the lamp support structure 120 thereby sandwiching the lamp 150 between the lamp support structure 120 and the lens plate 180. The guard component 210 is then coupled to the lens plate 180. In some embodiments, the guard component 210 may be formed of a resilient or elastomeric material, such as a thermoplastic elastomer. In such embodiments, the guard component 210 may be injection molded onto the lens plate 180 after the lens plate 180 is coupled to the lamp support structure 120 as described herein.

Referring to FIGS. 6A, 6B, 24, and 26 concurrently, the housing 301 and the components housed therein will be briefly described. As can be seen in these figures, a first portion 302 of the housing 301 is integrally formed with the lamp support structure 120 as a monolithic structure and a second portion 303 of the housing 301 is integrally formed with the handle 300. The handle 300 is coupled to the lamp support structure 120 by coupling the first and second portions 302, 303 of the housing together, which forms the fully enclosed housing 301, whereby portions of the housing 301 are formed by each of the handle 300 and the lamp support structure 120. The handle 300 also comprises an end cap 304 that is separate from and coupled to the second portion 303 of the housing 301.

Figure 24:
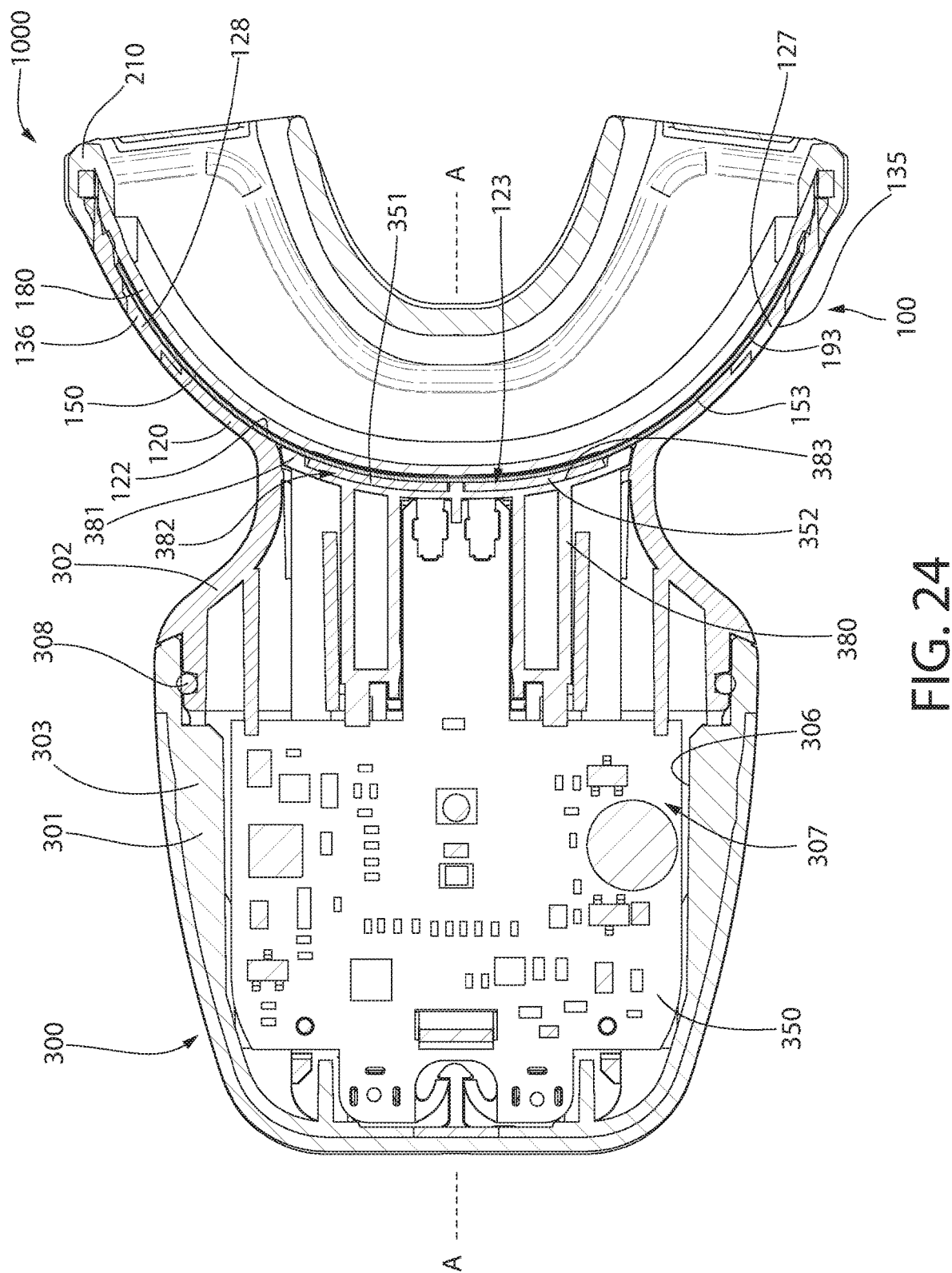
FIG. 24 is a cross-section taken along line XXIV-XXIV of FIG. 3.

As mentioned above, the housing 301 contains a control circuit 350. The control circuit 350 comprises a control unit 370 and an actuation unit 380. The control unit 370 and the actuation unit 380 are separate components, but when the oral treatment device 1000 is assembled they are operably coupled together. The actuation unit 380 operates in conjunction with the actuator 305 to power the oral treatment device 1000 on and off. Furthermore, the actuation unit 380 comprises a front wall 381 with depressions 382, 383 therein, the depressions 382, 383 each having a floor 384. As best shown in FIG. 24 and described in more detail below, when the oral treatment device 1000 is assembled, the front wall 381 of the actuation unit 380 forms a portion of a lamp support surface to which the lamp 150 is coupled. Specifically, the lamp support structure 120 and the front wall 381 of the actuation unit 380 collectively form the lamp support surface.

The control unit 370 generally comprises, among other components, a properly programmed processor, a memory device, a power source 360, and a timer that are operably coupled together. The control unit 370 is also operably coupled to the actuation unit 380 and specifically to the actuator 305. The control circuit 350 also comprises a first compressible electrical contact 351 and a second compressible electrical contact 352, each of which is operably coupled to the power source 360. The first compressible electrical contact 351 has a first electrical charge and the second compressible electrical contact 352 has a second electrical charge, the first and second electrical charges being opposite to one another. Thus, if the first electrical charge is positive, then the second electrical charge is negative, and vice versa.

The control circuit 350, in turn, is operably and electrically coupled to the lamp 150 so that the control circuit 350 can control the operation thereof. More specifically, and as described in much more detail below, the lamp 150 comprises electrical contacts that contact the first and second compressible electrical contacts 351, 352 of the control circuit 350 to transmit power from the power source 360 to the lamp 150 so that light or other electromagnetic radiation may be generated by the lamp and emitted from the oral treatment device 1000.

In the exemplified embodiment, the first and second electrical contacts 351, 352 are indicated as being compressible. This means that the first and second compressible electrical contacts 351, 352 may compress when a force is applied thereto. In some embodiments, the first and second compressible electrical contacts 351, 352 comprise a body formed of a compressible material and an electrically conductive layer on the compressible material. In certain embodiments, the first and second compressible electrical contacts 351, 352 may be formed from an electrically conductive mesh that is filled with a compressible material. The compressible material may in some embodiments be foam, although other materials are possible so long as it permits compression of the electrical contacts 351, 352, which as will be discussed further below increases the physical contact between the first and second electrical contacts 351, 352 and electrical contacts on the lamp 150. In some embodiments, the first and second compressible electrical contacts 351, 352 are resilient such that they can be compressed or otherwise deformed in response to a force being applied therein. The first and second compressible electrical contacts 351, 352 should have an electrically conductive material (e.g., the electrically conductive mesh) on their exterior for facilitating the electrical coupling with the lamp 150 and the power source 360. The electrically conductive mesh may be a metal (e.g., such as silver, copper, aluminum, iron, steel, brass, or the like) or other electrically conductive material as may be desired. In some embodiments, the electrically conductive mesh may be woven like a tube with the foam acting as a compressible material residing inside of the tube-like electrically conductive mesh.

Of course, the first and second compressible electrical contacts 351, 352 need not be compressible in all embodiments. Rather, the first and second compressible electrical contacts 351, 352 could instead be traditional electrical contacts that are formed from an electrically conductive material (i.e., metal such as silver, copper, aluminum, iron, steel, brass, or the like) but that are not compressible. The compressible feature of the first and second compressible electrical contacts 351, 352 increases the electrical coupling between the electrical contacts of the lamp 150 and the first and second compressible electrical contacts 351, 352, but is not required in all embodiments.

When the device is assembled as shown in FIG. 24, the first and second compressible electrical contacts 351, 352 nest within the depression 382 of the front wall 381 of the actuation unit 380 of the control circuit 350. However, the first and second compressible electrical contacts 351, 352 protrude slightly from the front wall 381. As a result, when the lamp 150 is coupled to the lamp support structure 120, electrical contacts of the lamp 150 (described below) contact and compress the compressible electrical contacts 351, 352 thereby electrically coupling the lamp 150 to the compressible electrical contacts 351, 352. This will be described in greater detail below with reference to FIG. 21B.

The properly programmed processor may be any suitable microprocessor based programmable logic controller, personal computer, or the like that has memory for storing various instructions to control the operation of the lamp 150. The processor is programmed with algorithms to receive data from the various other electrical components and sensors, analyze the data, and cause the electrical components to operate in a desired or predetermined manner based on instructions that are stored in the memory device or an integrated memory area of the processor.

In the illustrated embodiment, the power source 360 is operably and electrically coupled to the processor and to the lamp 150 so that electrical energy can be provided thereto for powering the same. The power source 360 may be one or more batteries, battery cells, printed batteries, rechargeable batteries, super capacitors, or a control circuit that stores electrical energy. Alternatively, in certain embodiments the power source 360 may be omitted and instead the electronic components of the oral treatment device 1000 may be powered by a plug that is coupled to a power supply, such as a wall socket.

Figure 7:
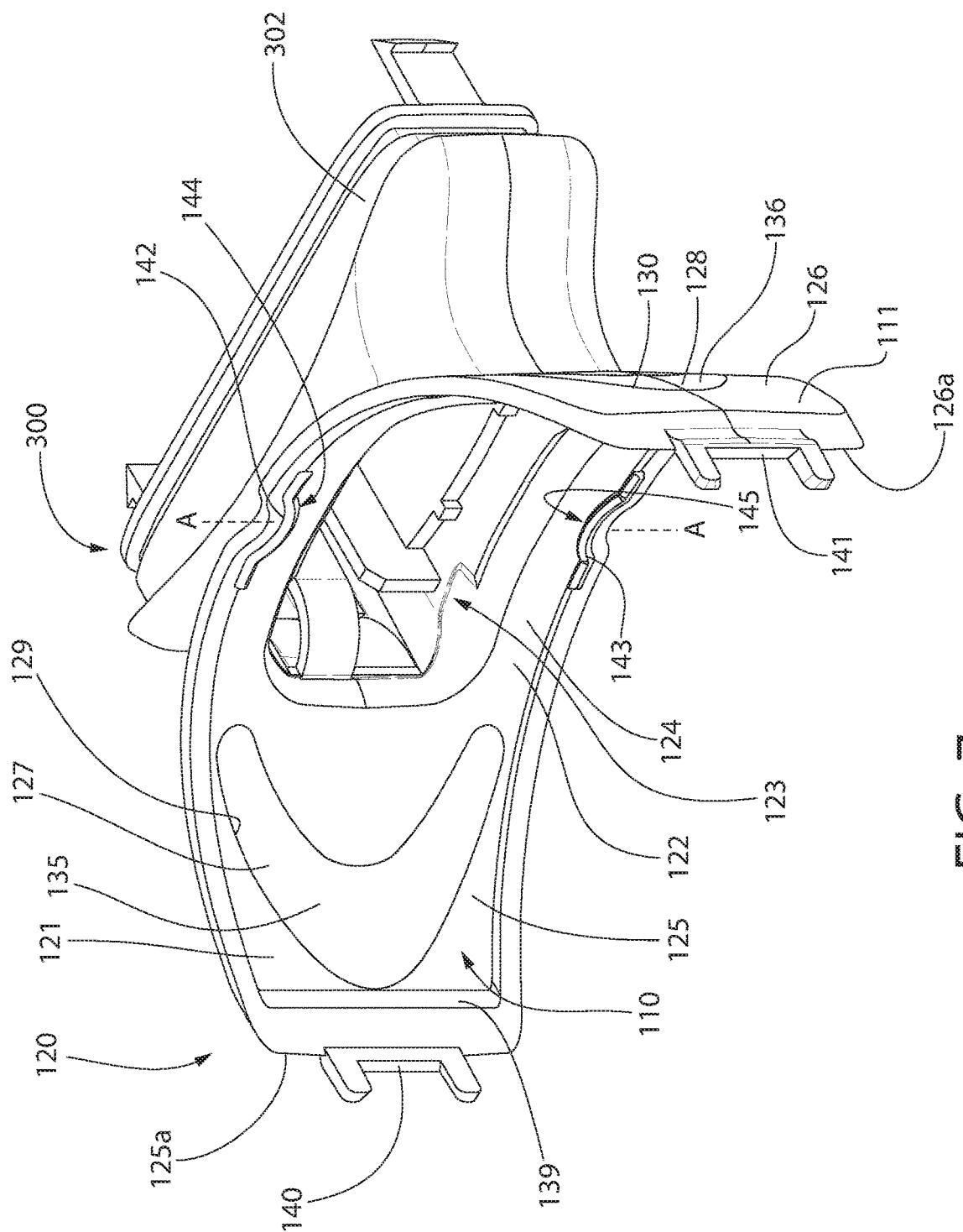
FIG. 7 is a front perspective view of a lamp support structure of the oral treatment device of FIG. 1, in accordance with an embodiment of the present invention.
Figure 8:
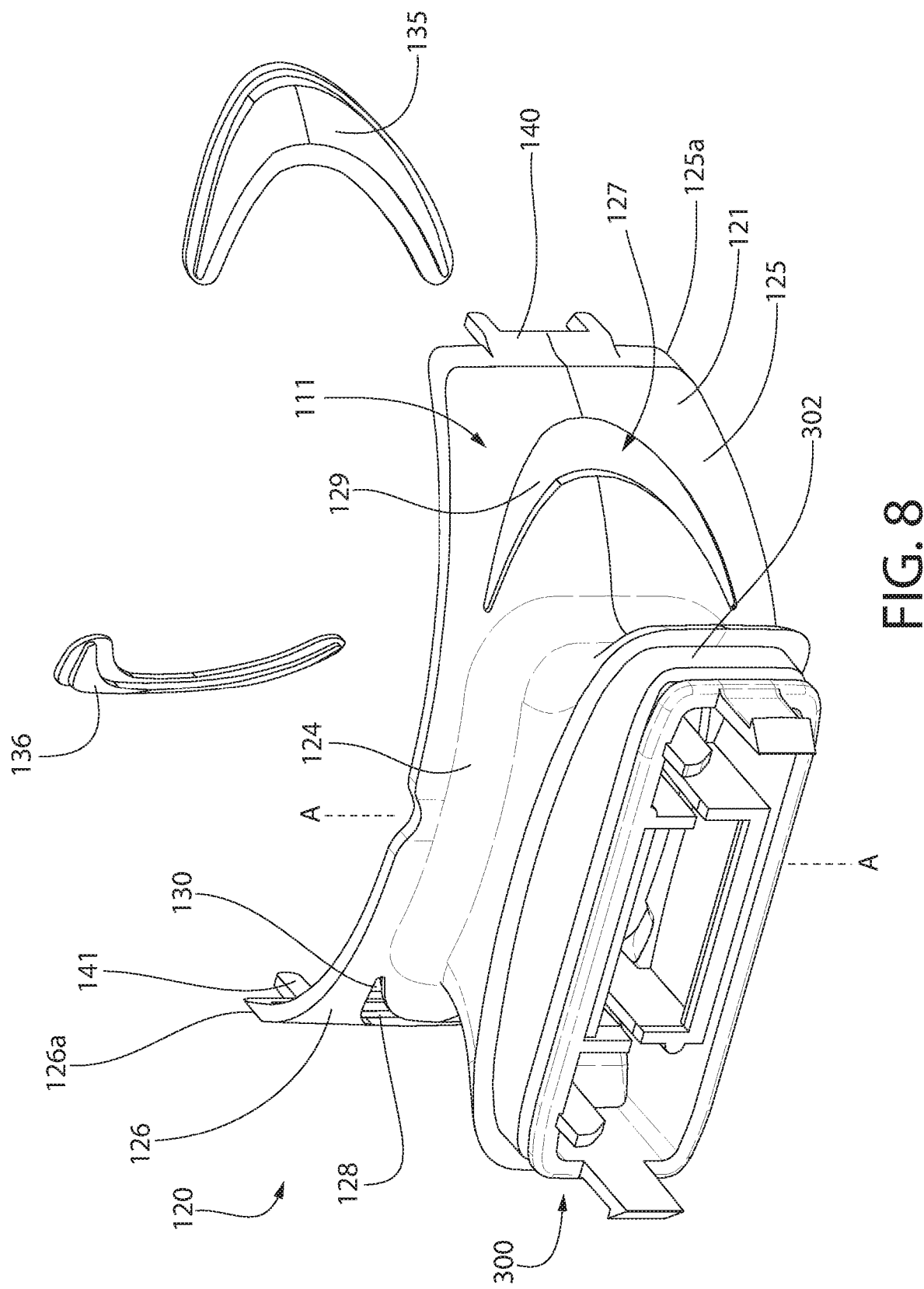
FIG. 8 is a rear perspective view of the lamp support structure of FIG. 7, with an elastomeric material that fills in relief slots thereof being exploded away.
Figure 9:
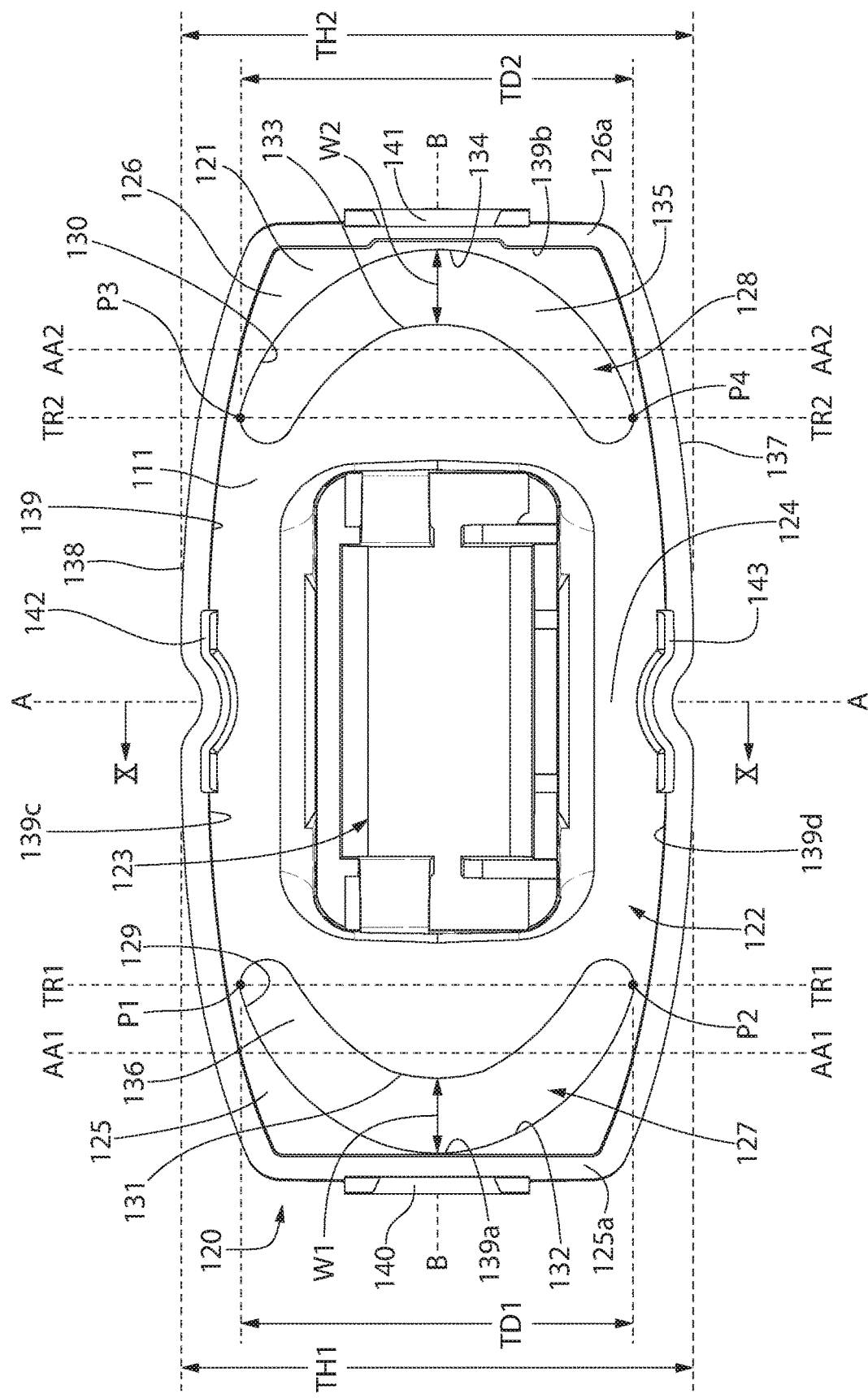
FIG. 9 is a front view of the lamp support structure of FIG. 7.
Figure 16:
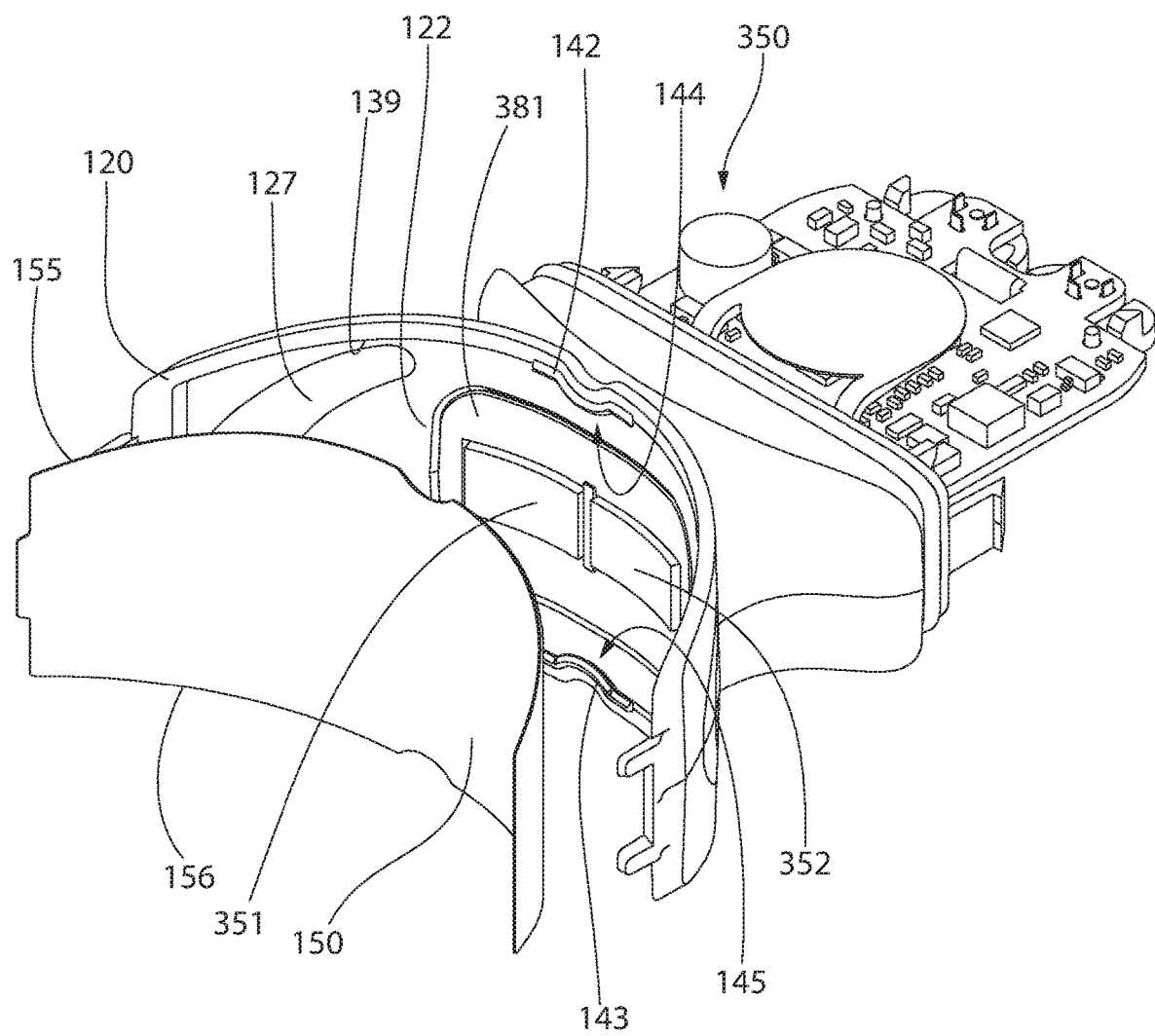
FIG. 16 is a perspective view illustrating the lamp adjacent to the lamp support structure in preparation for coupling those two components together.

Referring to FIGS. 7-9, the lamp support structure 120 will be further described. The lamp support structure 120 comprises a curved support plate 121 and the first portion 302 of the housing 300. The curved support plate 121 comprises a concave front surface 110 and a convex rear surface 111. The concave front surface 110 of the lamp support structure 120 forms at least a portion of a lamp support surface 122 (the rest of the lamp support surface 122 being formed by the front wall 381 of the actuation unit 380 as mentioned above). The lamp support structure 120 comprises an opening 123 formed into the lamp support surface 122 that extends all the way through to the back end of the first portion 302 of the housing 300. In the assembled oral treatment device 1000, portions of the control circuit 350 extend through the first portion 302 of the housing 300 and into the opening 123 in the lamp support surface 122. Specifically, as best seen in FIGS. 16 and 24, the actuation unit 380 is positioned so that the front wall 381 and the first and second compressible electrical contacts 351, 352 extend into the opening 123. Thus, in the fully assembled oral treatment device 1000, the lamp support surface 122 is formed partially by the lamp support structure 120 and partially by the front wall 381 and the first and second compressible electrical contacts 351, 352 of the actuation unit 380. This will be described in greater detail below with reference to FIG. 16.

The lamp support structure 120 extends along an arcuate longitudinal axis B-B that extends from a first distal side edge 125a of the curved support plate 121 to a second distal side edge 126a of the curved support plate 121. The curved support plate 121 comprises a central portion 124, a first end portion 125 extending from the central portion 124 to the first distal side edge 125a, and a second end portion 126 extending from the central portion 124 to the second distal side edge 126a. Furthermore, the curved support plate 121 comprises a first relief element 127 located on a first side of the dental arch midline plane A-A and a second relief element 128 located on a second side of the dental arch midline plane A-A. The first relief element 127 is located within the first end portion 125 of the curved support plate 121 and the second relief element 128 is located within the second end portion 126 of the curved support plate 121.

Figure 9A:
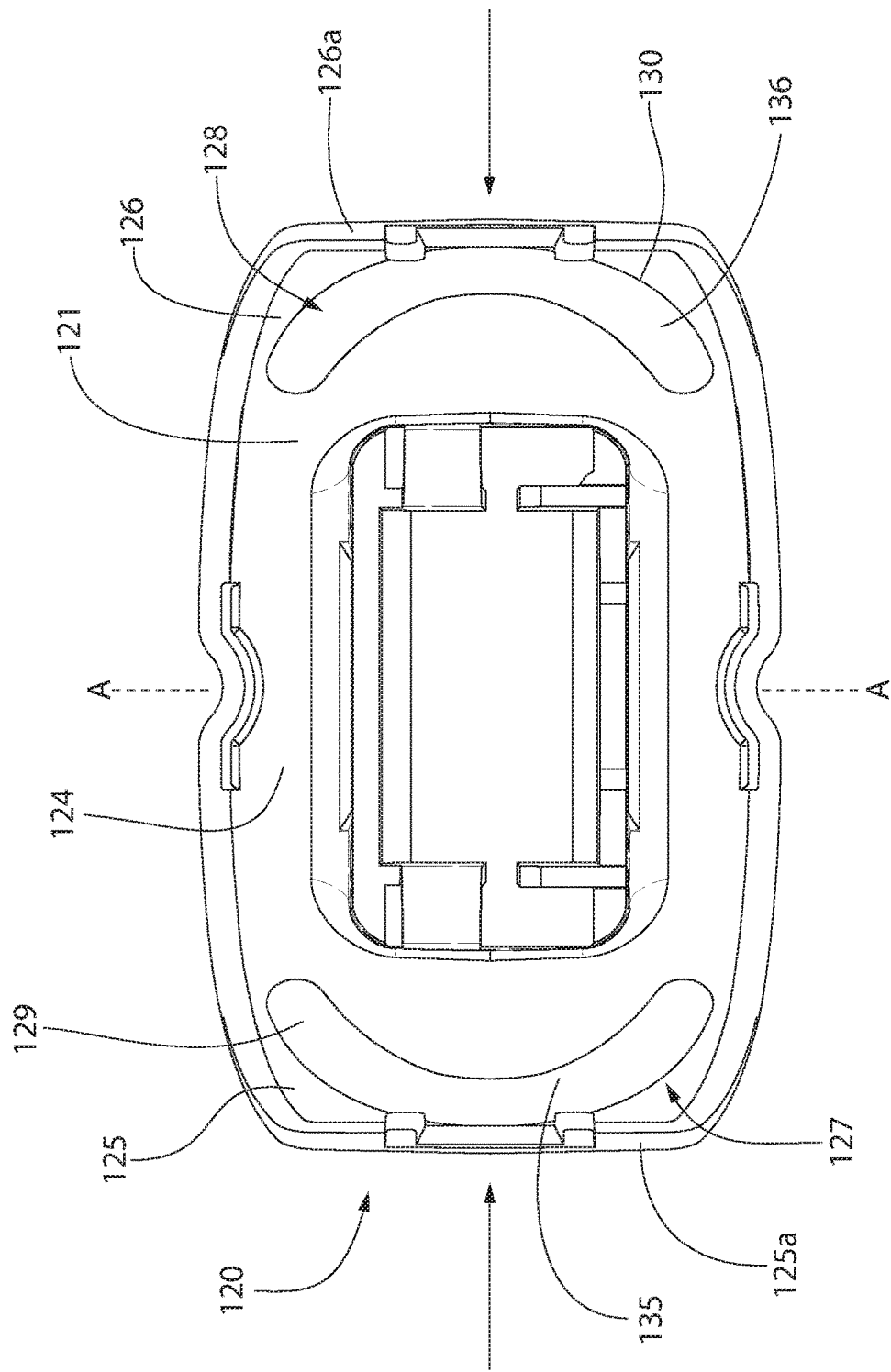
FIG. 9A is the front view of the lamp support structure shown in FIG. 9 with first and second end portions in a flexed state.
Figure 10:
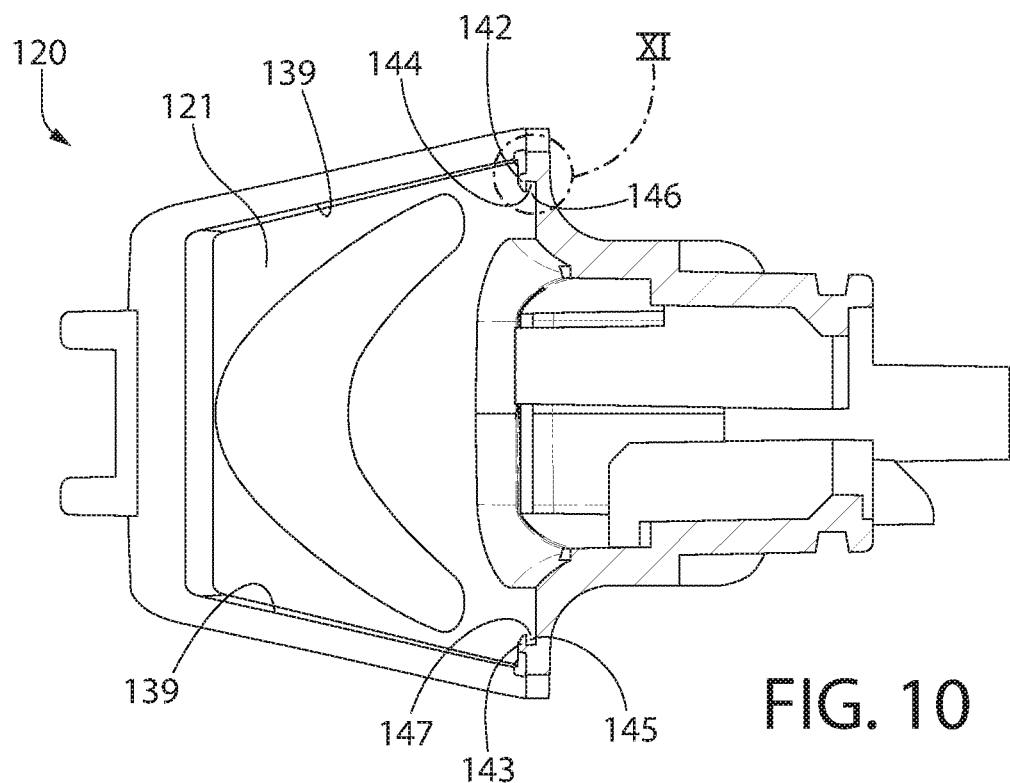
FIG. 10 is a cross-sectional view taken along line X-X of FIG. 9
Figure 11:
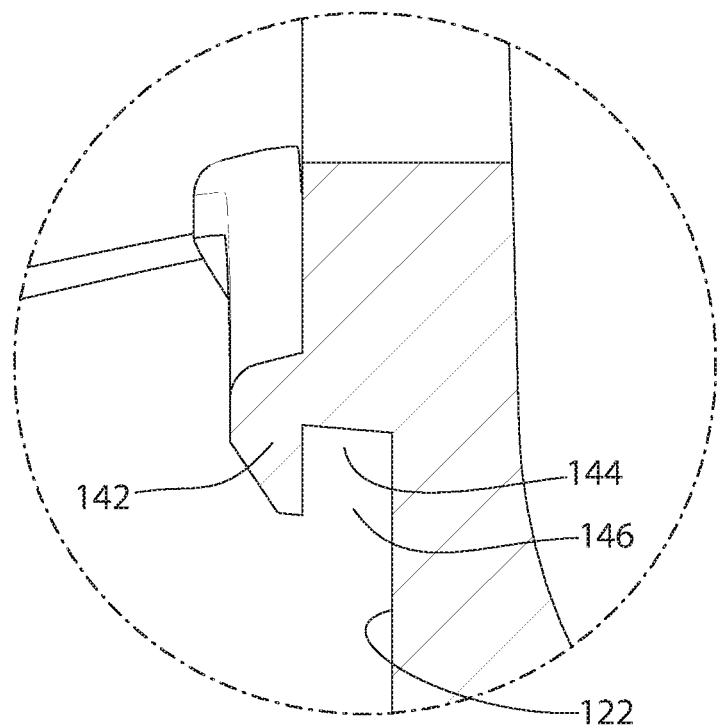
FIG. 11 is a close-up view of area XI-XI of FIG. 10.
Figure 12:
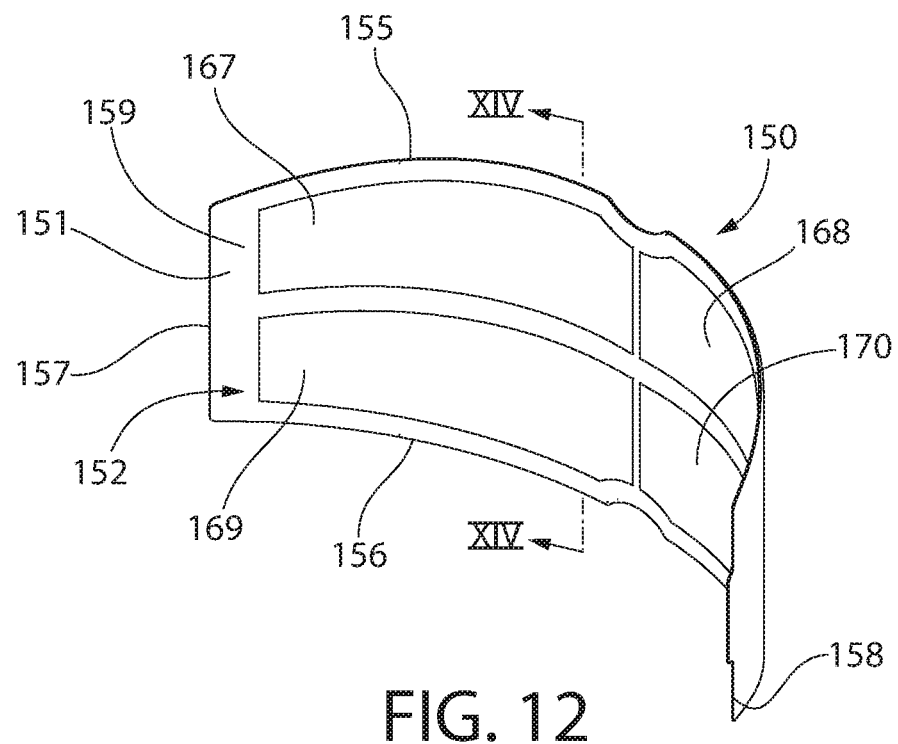
FIG. 12 is a front perspective view of a lamp of the oral treatment device of FIG. 1 in accordance with an embodiment of the present invention.
Figure 13:
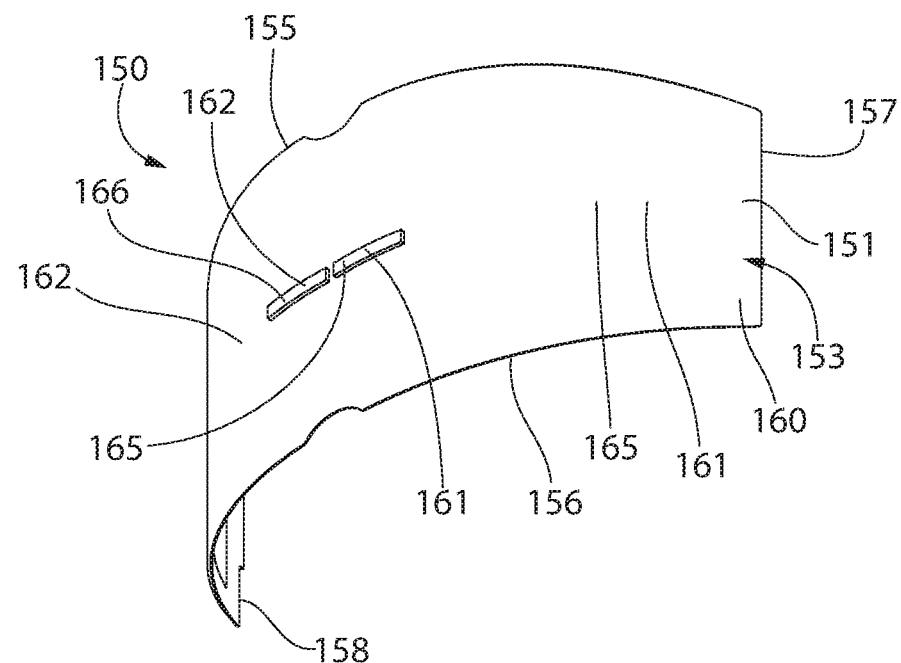
FIG. 13 is a rear perspective view of the lamp of FIG. 11.
Figure 14:
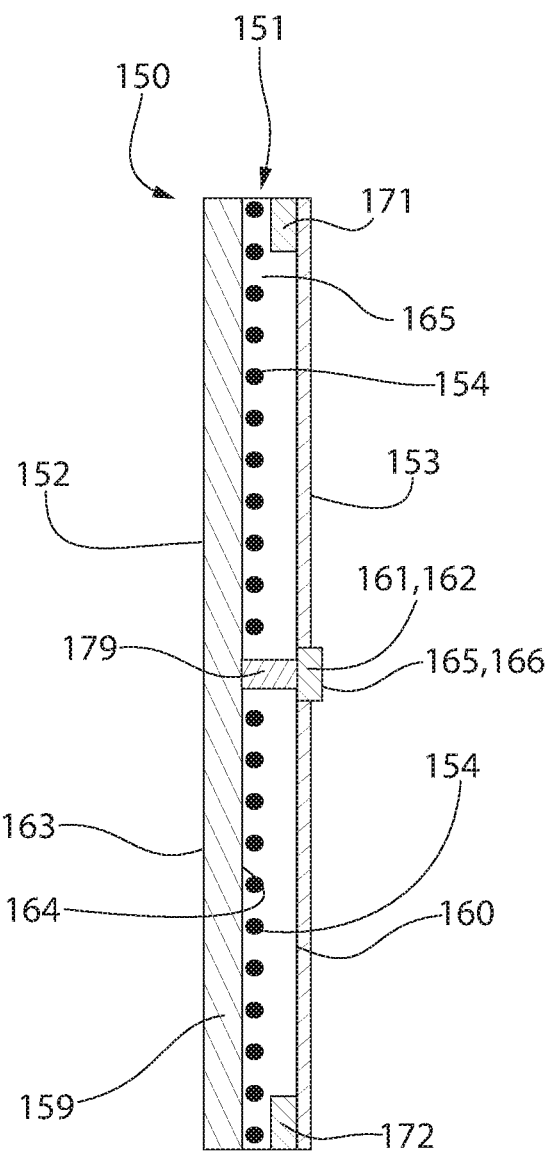
FIG. 14 is a cross-sectional view taken along line XIV-XIV of FIG. 12.

The first relief element 127 increases flexibility of the first end portion 125 of the curved support plate 121 relative to the central portion 124 and the second relief element 128 increases flexibility of the second end portion 126 of the curved support plate 121 relative to the central portion 124. Specifically, referring to FIGS. 9 and 9A, the flexibility of the curved support plate 121 is illustrated. In FIG. 9A, the first and second end portions 125, 126 of the curved support plate 121 are being flexed relative to the central portion 124 of the curved support plate 121. This flexing is achieved by applying a force onto the first and second distal side edges 125a, 125b of the curved support plate 121. The first and second relief elements 127, 128 facilitate this flexing capability of the curved support plate 121.

The curved support plate 121 is generally formed of a rigid material, such as a hard plastic. Thus, without the first and second relief elements 127, 128, the curved support plate 121 would only be able to be flexed very minimally, if at all. However, in some embodiments the mouthpiece 100 is not custom made, but rather the same size and shape device is intended to be used by different people having different mouth sizes and shapes. For example, the mouthpiece 100 may come in a few different sizes (e.g., small, medium, large). However, people have more than three different mouth sizes, so such standard sizing is not always optimal. By including the first and second relief elements 127, 128, the curved support plate 121 is able to flex so that the mouthpiece 100 can fit into mouths of different size. Specifically, if a person with a smaller mouth were to insert the mouthpiece into his/her mouth, both of the first and second end portions 125, 126 of the curved support plate 121 would flex relative to the central portion 124 of the curved support plate 121 to facilitate insertion into the smaller mouth.

In the exemplified embodiment, the first relief element 127 is a first elongated aperture 129 and the second relief element 128 is a second elongated aperture 130 (best shown in FIG. 8) formed through the curved support plate 121. Each of the first and second elongated apertures 129, 130 is a closed-geometry aperture defined entirely by the curved support plate 121. Furthermore, in the exemplified embodiment, each of the first and second elongated apertures 129, 130 is arcuate in shape. Thus, in the exemplified embodiment, the first elongated aperture 129 is defined, at least in part, by a first convex edge 131 of the central portion 124 of the curved support plate 121 and a first concave edge 132 of the first end portion 125 of the curved support plate 121. Similarly, the second elongated aperture 130 is defined, at least in part, by a second convex edge 133 of the central portion 124 of the curved support plate 121 and a second concave edge 134 of the second end portion 126 of the curved support plate 121. Of course, the invention is not to be limited by the exact shape of the elongated apertures 129, 130 in all embodiments and the first and second elongated apertures 129, 130 may take other shapes, such as rectangular, square, triangular, irregular, or the like, while still permitting and facilitating the desired flexing of the curved support plate 121 as described herein.

In the exemplified embodiment, each of the first and second elongated apertures 129, 130 is filled with an elastomeric material. Thus, the lamp support structure 120, in its final assembled state, does not have openings in the curved support plate 121. Rather, the openings that form the first and second elongated apertures 129, 130 are filled with an elastomeric material, such as a thermoplastic elastomer or the like. Thus, the first elongated aperture 129 may be filled with a first elastomeric component 135 and the second elongated aperture 130 may be filled with a second elastomeric component 136. The first and second elastomeric components 135, 136 may be injection molded directly into the first and second elongated apertures 129, 130, or they may be formed separately from the curved support plate 121 and coupled thereto using an interference fit or other mechanical means.

The curved support plate 121 is formed of a hard plastic material and the elastomeric material filler in the first and second elongated apertures 129, 130 is much more resilient and flexible than the hard plastic. Stated another way, the curved support plate 121 is formed of a first material having a first hardness and the first and second relief elements 127, 128 are sealed with a second material (i.e., the first and second elastomeric components 135, 136, for example) having a second hardness which is less than the first hardness. Thus, even though the elongated apertures 129, 130 are filled, the relief elements 127, 128 are still capable of increasing the flexibility of the first and second end portions 125, 126 of the curved support plate 121 relative to the central portion 124 of the curved support plate 121.

The first relief element 127 extends from a first point P1 above the arcuate longitudinal axis B-B to a second point P2 below the arcuate longitudinal axis B-B. Similarly, the second relief element 128 extends from a first point P4 above the arcuate longitudinal axis B-B to a second point P4 below the arcuate longitudinal axis B-B. Each of the first and second relief elements 127, 128 is symmetric about the arcuate longitudinal axis B-B of the lamp support structure 120. Furthermore, the first and second relief elements 127 have lengths that extend for most of the height of the curved support plate 121. This is needed to allow for the desired flexing of the curved support plate as described herein above. Thus, a first transverse distance TD1 between the first and second points P1, P2 of the first relief element 127 measured along a first transverse reference line TR1 is at least a majority of a first transverse height TH1 of the curved support plate 120 measured along the first transverse reference line TR1 from a bottom edge 137 of the curved support plate 121 to a top edge 138 of the curved support plate 121. Similarly, a second transverse distance TD2 between the first and second points P3, P4 of the second relief element 128 measured along a second transverse reference line TR2 is at least a majority of a second transverse height TH2 of the curved support plate 121 measured along the second transverse reference line TR2 from the bottom edge 137 of the curved support plate 121 to the top edge 138 of the curved support plate 121. In the exemplified embodiment, the first and second transverse distances TD1, TD2 are at least 70%, or at least 75%, or at least 80%, or at least 85%, or at least 90%, or at least 95% of the first and second transverse heights TH1, TH2 of the curved support plate 120. Thus, only a small percentage of the curved support plate 121 is formed of the hard plastic in this region, the remainder being formed from a resilient material (or an opening), thereby enhancing the flexibility of the curved support plate 121 as described herein.

Moreover, the first elongated aperture 129 of the first relief element 127 extends along a first aperture axis AA1-AA1 and the second elongated aperture 130 of the second relief element 128 extends along a second aperture axis AA2-AA2. The first elongated aperture 129 has a first aperture width W1 measured in a direction transverse to the first aperture axis AA1-AA1. The first aperture width W1 decreases with distance from the arcuate longitudinal axis B-B of the lamp support structure 120 in both directions towards the first point P1 and towards the second point P2. The second elongated aperture 130 has a second aperture width W2 measured in a direction transverse to the second aperture axis AA2-AA2. The second aperture width W2 decreases with distance from the arcuate longitudinal axis B-B of the lamp support structure 120 in both directions towards the first point P3 and towards the second point P4.

Still referring to FIGS. 7-9, the lamp support structure 120, and more specifically the curved support plate 121 thereof, comprises a perimetric lamp retaining wall 139 protruding from and surrounding the lamp support surface 122. The perimetric lamp retaining wall 139 comprises a first side lamp retaining wall 139a, a second side lamp retaining wall 139b, an upper lamp retaining wall 139c, and a lower lamp retaining wall 139d. The first and second side lamp retaining walls 139a, 139b and the upper and lower lamp retaining walls 139c, 139d collectively define the perimetric lamp retaining wall 139, which is a closed geometric wall. The perimetric lamp retaining wall 139 extends upwardly away from the lamp support surface 122 such that the lamp support surface 122 is recessed relative to an outermost surface of the curved support plate 121 of the lamp support structure 120. When the lamp 150 is coupled to the lamp support structure 120, the lamp 150 is located entirely within the lamp support surface 122. Thus, the lamp 150, when so positioned, is surrounded by the perimetric lamp retaining wall 139. The perimetric lamp retaining wall 139 assists in maintaining the lamp 150 within the lamp support surface 122 of the lamp support structure 120.

The lamp support structure 129 further comprises a first connection element 140 protruding from the first distal side edge 125a of the curved support plate 121 and a second connection element 141 protruding from the second distal side edge 126a of the curved support plate 121. In the exemplified embodiment, each of the first and second connection elements 140, 141 of the lamp support structure 129 comprises two legs that protrude from the first and second distal side edges 125a, 126a, respectively, in a spaced apart manner. Thus, there is a gap between the two legs of each of the first and second connection elements 140, 141. The first and second connection elements 140, 141 are configured to interact and mate with connection elements on the lens plate 180, as discussed more fully below with reference to FIGS. 20 and 21, to couple the lens plate 180 to the lamp support structure 129.

Referring to FIGS. 7 and 9-11, the lamp support structure 120 further comprises at least one upper overhang structure 142 and at least one lower overhang structure 143. There is exactly one of the upper overhang structures 142 and one of the lower overhang structures 143 in the exemplified embodiment. However, in alternative embodiments more than one of one or both of the upper and lower overhang structures 142, 143 could be included on the lamp support structure 120. As seen in FIG. 9, in the exemplified embodiment each of the upper and lower overhang structures 142, 143 are located on the dental arch midline plane A-A. However, this is not required in all embodiments and the upper and lower overhang structures 142, 143 could be located at other positions in other embodiments. However, centering the upper and lower overhang structures 142, 143 along the lamp support surface 122 assists in retaining the lamp 150 thereon and maintaining the lamp 150 in its flexed and curved shape, as will be discussed in more detail below.

The upper overhang structure 142 protrudes from and extends downwardly from the upper lamp retaining wall 139c at a distal end of the upper lamp retaining wall 139c. Thus, the upper overhang structure 142 is spaced apart from the lamp support surface 122. As a result, the upper overhang structure 142 defines an upper slot 144 having an open bottom 146, the upper slot 144 being defined between the upper overhang structure 142 and the lamp support surface 122. The lower overhang structure 143 protrudes from and extends upwardly from the lower lamp retaining wall 139d at a distal end of the lower lamp retaining wall 139d. Thus, the lower overhang structure 143 is spaced apart from the lamp support surface 122. As a result, the lower overhang structure 143 defines a lower slot 145 having an open top 147, the lower slot 145 being defined between the lower overhang structure 143 and the lamp support surface 122.

Thus, the lamp 150 can be inserted into the upper slot 144 through the open bottom 146 thereof and into the lower slot 145 through the open top 147 thereof. Once in the upper and lower slots 144, 145, the upper and lower overhang structures 142, 143 serve to hold the lamp 150 in place. Thus, the upper and lower overhang structures 142, 143 form a single point contact that holds the lamp in place 150. The curvature of the lamp 150 biases the lamp 150 against the end points and the lamp 150 snaps into place during assembly. The interaction between the lamp 150 and the lamp support structure 120 will be described in greater detail below with reference to FIGS. 16, 17, and 17A.

Referring to FIGS. 12-15, the lamp 150 will be described. In the exemplified embodiment, the lamp 150 is a singular structure that, when the oral treatment device 1000 is assembled, is located along the lamp support surface 122 of the lamp support structure 120. The lamp 150 comprises a flexible sheet body 151, which is an elongated sheet that is sufficiently flexible such that it can be bent from a planar state into a contoured shape having a curvature that generally corresponds to the arch of a user's dentiture. In one embodiment, the flexible sheet body 151 is in a planar state when no bending force is applied thereto. In another embodiment, the flexible sheet body 151 is flat when no bending force is applied thereto, but the flexible sheet body 151 can be bent into the desired curvature such as for example to match the curvature of the lamp support surface 122.

The flexible sheet body 151 of the lamp 150 generally comprises a front surface 152 and a rear surface 153. The lamp 150 also comprises a plurality of light emitters 154 embedded within the flexible sheet body 151 that generate light which is emitted from the front surface 152 of the flexible sheet body 151. In one embodiment, the light emitted by the plurality of light emitters 154 has a wavelength in a range of 375 nm to 520 nm. In another embodiment, the light emitted by the plurality of light emitters 154 has a wavelength in a range of 400 nm to 430 nm. In a further embodiment, the light emitted by the plurality of light emitters 154 has a wavelength in a range of 400 nm to 420 nm, and in still another embodiment the wavelength is in a range of 405 nm to 415 nm. The wavelength of light emitted by the light emitters 154 is generally known to be effective to whiten teeth.

The flexible sheet body 151 of the lamp 150 comprises an upper edge 155, a lower edge 156, a first side edge 157, and a second side edge 158. The flexible sheet body 151 comprises a length measured from the first side edge 157 to the second side edge 158 and a width measured from the upper edge 155 to the lower edge 156. The length may be in a range of 55-70 mm, more specifically 60-65 mm, and still more specifically 62-63 mm. The width may be in a range of 15-30 mm, more specifically 20-25 mm, and still more specifically 22-23 mm. In the exemplified embodiment, the flexible sheet body 151 is a laminate structure that generally comprises a flexible lens plate 159, a flexible reflective substrate 160, first and second electrical contacts 161, 162, an upper bus bar 171, and a lower bus bar 172. The plurality of light emitters 154 are disposed between the flexible lens plate 159 and the flexible reflective substrate 160. The upper and lower bus bars 171, 172 and portions of the first and second electrical contacts 161, 162 may also be located between the flexible lens plate 159 and the flexible reflective substrate 160. In some embodiments, when assembled, the flexible reflective substrate 160 is adjacent to the lamp support surface 122 and the light is emitted from the flexible lens plate 159 side of the flexible sheet body 151.

In one embodiment, the flexible lens plate 159 of the flexible sheet body 151 has a front surface 163 and a rear surface 164. The front surface 163 of the flexible lens plate 159 forms the front surface 153 of the flexible sheet body 151. The flexible lens plate 159 may be formed of a transparent biocompatible material, such as transparent PET. The plurality of light emitters 154, in one embodiment, are light emitting diodes ("LEDs") printed to the rear surface 164 of the flexible lens plate 159 of the flexible sheet body 151. In one such embodiment, the LEDs may be printed to the rear surface 164 with an electrically conductive ink 165.

Printed LEDs may be formed by depositing micro LED chips via a conductive ink formulation that can be printed in any shape to best conform to the teeth and jaw structure, which is ideal for optimized efficacy. Specifically, gallium nitride may be used to form the LEDs in some embodiments, which may then be mixed with resin and binders to form an ink, and a standard screen printer may be used to deposit the resulting ink over a desired surface. The electrically conductive ink 165 may include electrically conductive materials, such as by infusing graphite or other conductive materials into the ink. Although described herein as being printed LEDs, the plurality of light emitters 154 may, in certain embodiments, be any type of light source, particularly solid state light sources, which may include LEDs, OLEDs, HBLEDs, electroluminescent elements, or the like. In certain other embodiments, the plurality of light emitters 154 can be printed inorganic LEDs, micro conventional LEDs that are surface mounted to a flexible substrate/circuit, organic LEDs (OLEDs), or electroluminescence. In still other embodiments, the plurality of light emitters 154 can be any of the LEDs noted herein mounted to a rigid rather than a flexible substrate. In the exemplified embodiment, after the LEDs are printed onto the rear surface 164 of the flexible lens plate 159 and the conductive ink 165 is printed, a dielectric material 179 may be provided to insulate different regions/illumination zones of the lamp 150 from one another, as described in more detail below.

The lamp 150 may operate with a driving current that is less than or equal to 130 mA, although in some embodiments it may be between 75 mA and 105 mA. The lamp 150 may have an emittance at 90 mA that is greater than 9.2 mW/cm2. The lamp 150 may be divided into a plurality of distinct regions of equal surface area. Regardless of the breakdown of the regions, the lamp 150 may have a uniformity that is greater than 75% among the distinct regions. The lamp 150 may have a surface operating temperature that is below 48° C. when driven in accordance with the parameters set forth herein for a time period of 10 minutes.

After the LEDs are printed and the dielectric material 179 is added, the first and second electrical contacts 161, 162 and the upper and lower bus bars 171, 172 may be added, by printing or in any other manner (such as placing an electrically conductive material onto the conductive ink 165 or near it and then electrically coupling it to the conductive ink 165. The first and second electrical contacts 161, 162 and the upper and lower bus bars 171, 172 may be placed or otherwise provided onto the exposed side of the electrically conductive ink 165 and dielectric 179 that is opposite the rear surface 164 of the flexible lamp lens 159. Next, electrical contacts (e.g., the diodes depicted in FIG. 15) may be added between the upper and lower bus bars 171, 172 and the illumination zones and between the first and second electrical contacts 161, 162 and the illumination zones, as will be described in more detail below, in order to electrically couple the upper and lower bus bars 171, 172 and the electrical contacts 161, 162 to the illumination zones of the lamp 150.

Finally, the reflective layer 160, which is not conductive and may be considered an insulating layer, is positioned so as to completely cover the conductive ink 165, the dielectric 179, and the upper and lower bus bars 171, 172. Although in the exemplified embodiment the reflective layer 160 covers the upper and lower bus bars 171, 172 completely, in other embodiments at least portions of the upper and lower bus bars 171, 172 may remain exposed. The reflective layer 160 may also cover a portion of the first and second electrodes 161, 162 as shown, although a portion of the first and second electrodes 161, 162 must be left exposed so that they can make contact with, and therefore be electrically coupled to, the first and second compressible electrodes 351, 352 of the control circuit 350. Thus, a percentage (i.e., 50%, 60%, 75%) of the first and second electrical contacts 161, 162 may be covered by the reflective layer 160 while the rest of the first and second electrical contacts 161, 162 remains exposed. The exposed portions of the first and second electrical contacts 161, 162 that will be aligned with the first and second compressible electrical contacts 351, 352 in the assembled oral treatment device 1000 should be exposed.

Thus, portions of the first and second electrical contacts 161, 162 are exposed on the rear surface 153 of the flexible sheet body 151. The first electrical contact 161 has a first contact surface 165 and the second electrical contact 162 has a second contact surface 166. The first and second electrical contacts 161, 162 are spaced apart from one another. One of the first and second electrical contacts 161 operates as a positive electrical contact and the other of the first and second electrical contacts 162 operates as a negative electrical contact. Thus, the first and second electrical contacts 161, 162 must not be in contact with one another to avoid shorting the circuit.

Figure 15:
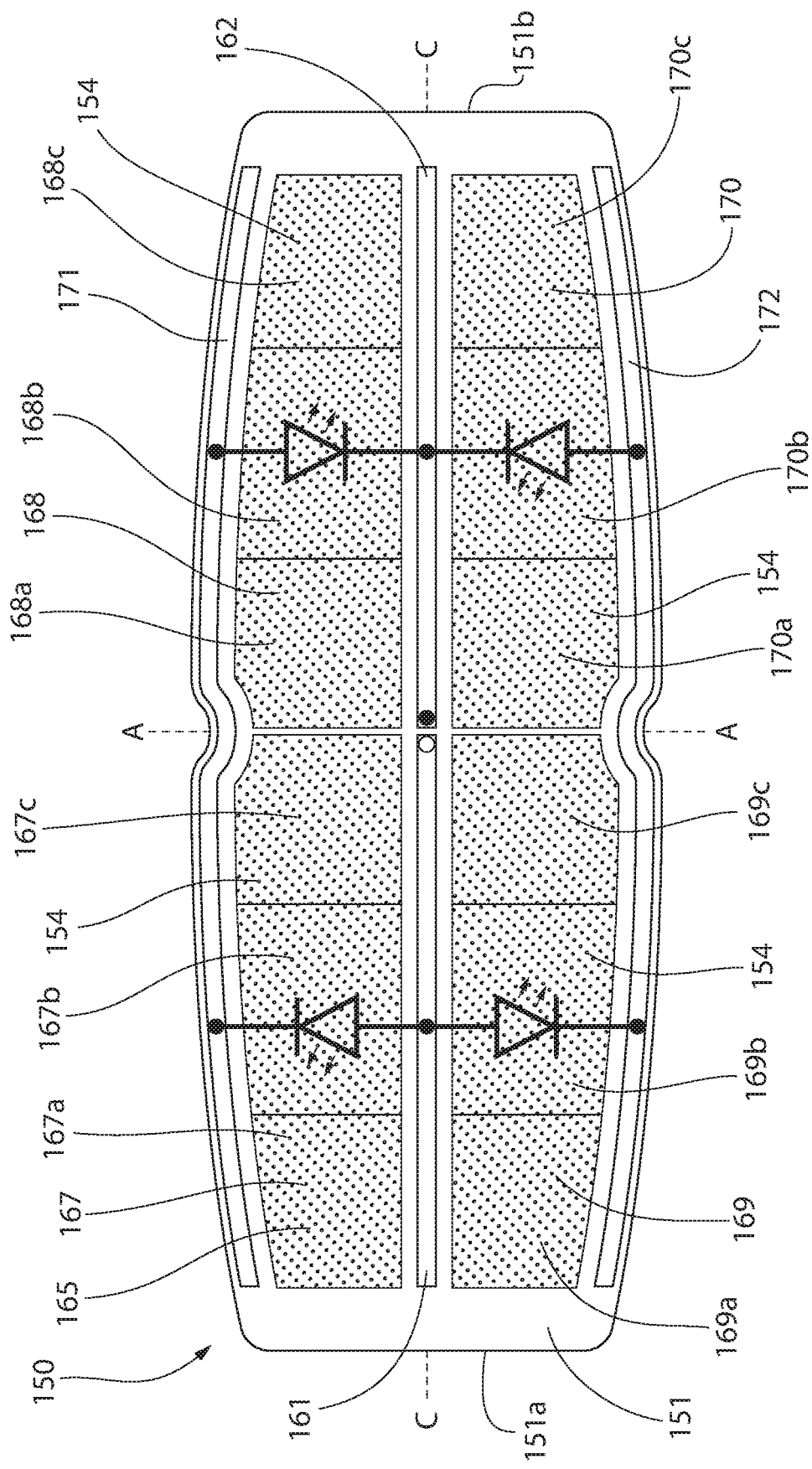
FIG. 15 is a schematic front view of the lamp of FIG. 11.

As illustrated, each of the first and second electrical contacts 161, 162 is in the form of an elongated strip that extends approximately one-half of the length of the lamp 150. In the exemplified embodiment, the first and second electrical contacts 161, 162 are located equidistant from the upper and lower edges 155, 156 of the flexible sheet body 151. In some embodiments, the first electrical contact 161 may be a first bus bar and the second electrical contact 162 may be a second bus bar. The first and second electrical contacts 161, 162 are spaced apart from one another along a midline of the flexible sheet body 151, perhaps as best shown in FIG. 15.

In one embodiment, the lamp 150 has an illumination area (i.e., area of the front surface 152 that comprises the plurality of light emitters 154) that is in a range of 10 cm$^2$ to 20 cm$^2$, more preferably in a range of 12 cm$^2$ to 16 cm$^2$, and most preferably in a range of 14 cm$^2$ to 15 cm$^2$. The height of illumination area may be in a range of 1 cm to 3 cm, and more preferably 2 cm to 3 cm, with 2.25 cm being most preferred. The length of illumination area may be in a range of 4 cm to 8 cm, more preferably in a range of 5 cm to 7 cm, and most preferably in a range of 6 cm to 6.5 cm. Of course, dimensions outside of these ranges are certainly possible. However, these ranges have been selected to optimize the side of the lamp 150 for different users having different sized oral cavities and mouths while ensuring that the mouthpiece 100 remains comfortable for all users for the desired treatment time.

The lamp 150 extends along a lamp longitudinal axis C-C from a first lamp side edge 151*a* of the flexible sheet body 151 to a second lamp side edge 151*b* of the flexible sheet body 151. In the exemplified embodiment, the first and second electrical contacts 161, 162 are located on the lamp longitudinal axis C-C, although this is not necessarily required in all embodiments. Thus, the first and second electrical contacts 161, 162 may be located at other positions along the rear surface 153 of the flexible sheet body 151 so long as they are positioned so as to come into electrical contact with the first and second compressible electrical contacts 351, 352 of the control circuit 350 when the oral treatment device 1000 is assembled. The lamp 150 also comprises a plurality of illumination zones that are electrically isolated from one another. However, each of the plurality of illumination zones is in electrical coupling with one of the first and second electrical contacts 161, 162 of the lamp 150 and one of the upper and lower bus bars 171, 172 that electrically couples at least two of the illumination zones together, which enables each of the illumination zones to receive power from the power source and to emit electromagnetic radiation from the front surface 152 of the flexible sheet body 151. The flow of current through the illumination zones will be described in greater detail below.

The plurality of illumination zones comprise a first upper illumination zone 167, a second upper illumination zone 168, a first lower illumination zone 169, and a second lower illumination zone 170. Although shown in FIG. 12, in actuality the various zones 167-170 will not be visible on the exterior of the lamp 150. Rather, the exterior of the lamp 150 will have a very plain, unassuming appearance. The demarcation of the various zones 167-170 takes place internally within the flexible sheet body 151, as described herein. FIG. 15 is a schematic illustration of the lamp 150 and thus it depicts the various zones 167-170 and other features that are not actually visible on the lamp 150 itself.

In the exemplified embodiment, the first and second upper illumination zones 167, 168 are located above the lamp longitudinal axis C-C and the first and second lower illumination zones 169, 170 are located below the lamp longitudinal axis C-C. In the assembled oral treatment device 1000, the first and second upper illumination zones 167, 168 are located above the bite platform 104 and the first and second lower illumination zones 169, 170 are located below the bite platform 104. Furthermore, in the exemplified embodiment the first and second upper illumination zones 167, 168 are arranged in series with one another between the first and second electrical contacts 161, 162 of the lamp 150 and the first and second lower illumination zones 169, 170 are arranged in series with one another between the first and second electrical contacts 161, 162 of the lamp 150. The first and second upper illumination zones 167, 168 are arranged in parallel to the first and second lower illumination zones 169, 170. In the exemplified embodiment, the lamp 150 comprises a single flexible sheet body 151 and each of the plurality of illumination zones 167-170 is on a single flexible sheet body 151

The upper bus bar 171 is located above the first and second upper illumination zones 167, 168, and more specifically between the first and second upper illumination zones 167, 168 and the upper edge 155 of the flexible sheet body 151. The upper bus bar 171 is an elongated strip formed of an electrically conductive material such as a metal that is elongated between the first and second side edges 151*a*, 151*b* of the flexible sheet body 151. The upper bus bar 171 extends in an uninterrupted manner for its entire length above each of the first and second upper illumination zones 167, 168. The upper bus bar 171 electrically couples the first and second upper illumination zones 167, 168 together, as described below.

The lower bus bar 172 is located below the first and second lower illumination zones 169, 170, and more specifically between the first and second lower illumination zones 169, 170 and the lower edge 156 of the flexible sheet body 161. The lower bus bar 172 electrically couples the first and second lower illumination zones 169, 170 together. The lower bus bar 172 is an elongated strip formed of an electrically conductive material such as a metal (e.g., silver, copper, aluminum, iron, steel, brass, or the like) that is elongated between the first and second side edges 151*a*, 151*b* of the flexible sheet body 151. The lower bus bar 172 extends in an uninterrupted manner below each of the first and second lower illumination zones 169, 170 along its entire length.

In the exemplified embodiment, portions of the first and second electrical contacts 161, 162 are located on (or exposed on) the rear surface 153 of the flexible sheet body 151 the upper and lower bus bars 171, 172 are embedded within the flexible sheet body 151 as described above and illustrated in FIG. 14. The first and second electrical contacts 161, 162 are adjacent to one another and axially spaced apart from one another. The upper and lower bus bars 171, 172 extend in a direction that is generally parallel to the first and second electrical contacts 161, 162, although in the exemplified embodiment the upper and lower bus bars 171, 172 may have a slight curve rather than being perfectly straight. Thus, the upper and lower bus bars 171, 172 are elongated in the same direction that the first and second electrical contacts 161, 162 are elongated. The upper and lower bus bars 171, 172 are spaced apart from one another and from each of the first and second electrical contacts 161, 162, with the first and second electrical contacts 161, 162 being located between the upper and lower bus bars 171, 172 in a direction that is transverse to the lamp longitudinal axis C-C.

The first electrical contact 161 is a first bus bar formed of an electrically conductive material such as a metal that is elongated and positioned between the first upper illumination zone 167 and the first lower illumination zone 169. The second electrical contact 162 is a second bus bar formed of an electrically conductive material such as a metal that is elongated and positioned between the second upper illumination zone 168 and the second lower illumination zone 170. The first upper illumination zone 167, the first lower illumination zone 169, and the first electrical contact 161 are located on a first side of the dental arch midline plane A-A. The second upper illumination zone 168, the second lower illumination zone 170, and the second electrical contact 162 are located on a second side of the dental arch midline plane A-A that is opposite the first side. The upper and lower bus bars 171, 172 are each located on both sides of the dental arch midline plane A-A. The first and second electrical contacts 161, 162 may be any electrically conductive material, but possible metals include silver, copper, aluminum, iron, steel, brass, or the like.

As described above, in the exemplified embodiment, the plurality of light emitters 154 comprises a plurality of LEDs or the like that are printed with an electrically conductive ink 165. In such an embodiment, the electrically conductive ink 165 is electrically coupled to each of the first and second electrical contacts 161, 162 and each of the upper and lower bus bars 171, 172 of the lamp 150. More specifically, the electrically conductive ink 165 in the first upper illumination zone 167 is electrically coupled to the first electrical contact 161 and to the upper bus bar 171, the electrically conductive ink 165 in the second upper illumination zone 168 is electrically coupled to the upper bus bar 171 and the second electrical contact 162, the electrically conductive ink 165 in the first lower illumination zone 169 is electrically coupled to the first electrical contact 161 and the lower bus bar 172, and the electrically conductive ink 165 in the second lower illumination zone 170 is electrically coupled to the lower bus bar 172 and the second electrical contact 162.

As shown schematically in FIG. 15, this electrical coupling between the various illumination zones and the electrical contacts/bus bars is achieved with diodes. Thus, a first diode is electrically coupled to the first electrical contact 161, the first upper illumination zone 167, and the upper bus bar 171. A second diode is electrically coupled to the upper bus bar 171, the second upper illumination zone 168, and the second electrical contact 162. A third diode is electrically coupled to the first electrical contact 161, the first lower illumination zone 169, and the lower bus bar 172. A fourth diode is electrically coupled to the lower bus bar 172, the second lower illumination zone 170, and the second electrical contact 162. When the oral treatment device 1000 is assembled, the first electrical contact 161 of the lamp 150 is electrically coupled to the first compressible electrical contact element 351 and the second electrical contact 162 of the lamp 150 is electrically coupled to the second compressible electrical contact element 352. These electrical couplings facilitate providing power to each of the illumination zones 167-170 so that each can emit electromagnetic radiation/light as described herein.

Due to the electrical coupling between the various electrical contacts 161, 162, bus bars 171, 172, and the electrically conductive ink 165 (in the various illumination zones 167-170), current will flow as follows: (1) from the first electrical contact 161 through the electrically conductive ink 165 in the first upper illumination zone 167 of the lamp 150 to the upper bus bar 171; (2) from the upper bus bar 171 through the electrically conductive ink 165 in the second upper illumination zone 168 of the lamp 150 to the second electrical contact 162; (3) from the first electrical contact 161 through the electrically conductive ink 165 in the first lower illumination zone 169 of the lamp 150 to the lower bus bar 172; and (4) from the lower bus bar 172 through the electrically conductive ink 165 in the second lower illumination zone 169 of the lamp 150 to the second electrical contact 162. As a result, all of the illumination zones 167-170 will be powered simultaneously when the first and second electrical contacts 161, 162 are coupled to the first and second compressible electrical contacts 351, 352, which are in turn coupled to the power source 360. Thus, the upper illumination zones 167, 168 are in series with one another, the lower illumination zones 169, 170 are in series with one another, the first upper illumination zone 167 is in parallel with the first lower illumination zone 169, and the second upper illumination zone 168 is in parallel with the second lower illumination zone 170.

Referring to FIG. 15, in some embodiments the illumination zones 167-170 may be subdivided into a plurality of sub-zones. Thus, the first upper illumination zone 167 may comprise first, second, and third sub-zones 167a, 167b, 167c, the second upper illumination zone 168 may comprise first, second, and third sub-zones 168a, 168b, 168c, the first lower illumination zone 169 may comprise first, second, and third sub-zones 169a, 169b, 169c, and the second lower illumination zone 170 may comprise first, second, and third sub-zones 170a, 170b, 170c. In some embodiments, the second and third sub-zones 167b, 167c of the first upper illumination zone 167 and the first and second sub-zones 168a, 168b of the second upper illumination zone 168 may form the four critical zones of the lamp 150. The reason for this is that the teeth that are most visible in day-to-day life are the front four teeth of a user's top jaw (i.e., the maxillary incisors). The four critical zones of the lamp 150 are aligned with the maxillary incisors during a normal tooth whitening procedure using the oral treatment device 1000 described herein.

In certain embodiments, the twelve sub-zones noted above have greater than 75% uniformity, more preferably greater than 85% uniformity. Furthermore, the four critical zones have greater than 90% uniformity. While the uniformity of the twelve sub-zones may decrease slightly after twenty-five hours of operation of the oral treatment device 1000, the uniformity of the four critical zones will not have any such drop. As used herein, uniformity refers to the consistency of the irradiance of the lamp 150 within the various indicated zones and sub-zones, irradiance being the radiant flux (i.e., power) received by a surface per unit area having an SI unit of watt per square meter ($W/m^2$).

Figure 17:
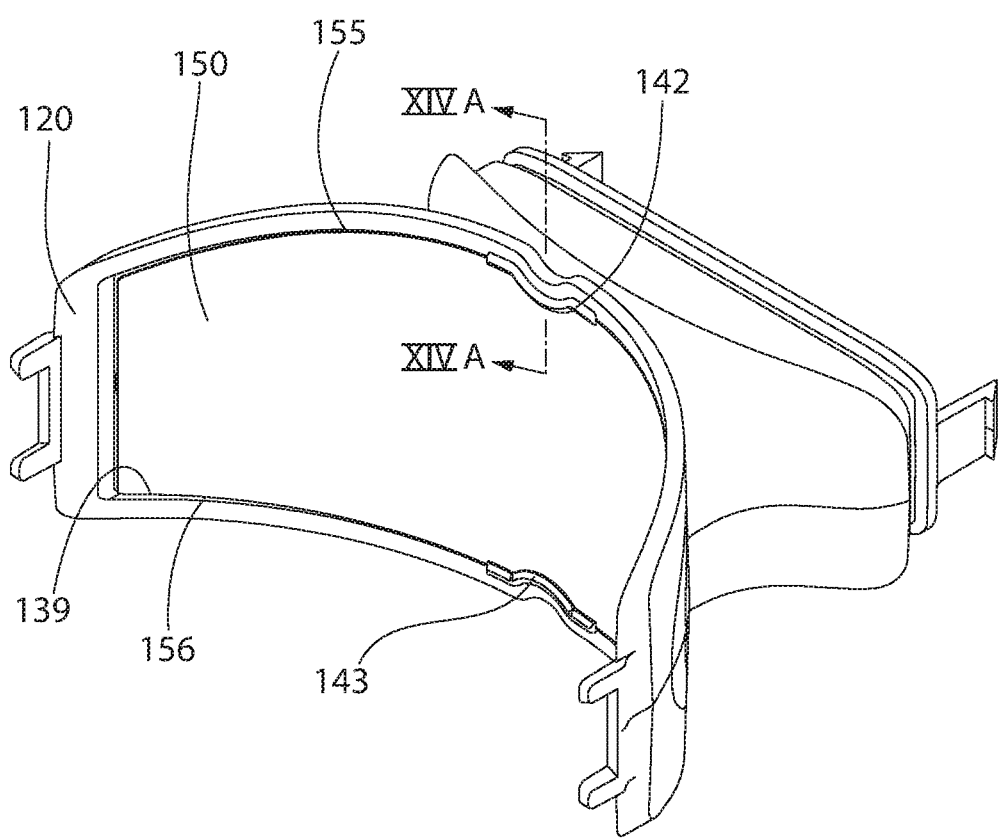
FIG. 17 is a perspective view illustrating the lamp and the lamp support structure coupled together in an assembled state.
Figure 17A:
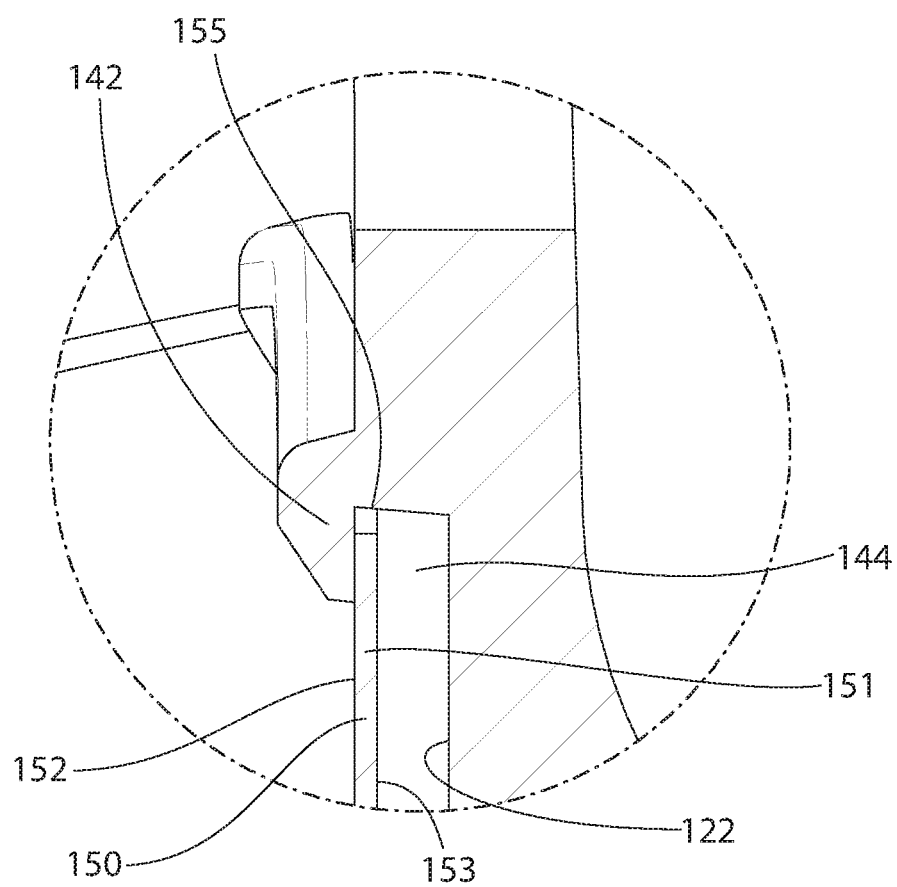
FIG. 17A is a cross-sectional view taken along line XVIIA-XVIIA of FIG. 17.

Referring to FIGS. 16, 17, and 17A concurrently, the coupling of the lamp 150 to the lamp support structure 120 will be described. As noted previously, when the control circuit 350 is in its assembled state/position, the front wall 381 of the actuation unit 380 forms a portion of the lamp support surface 122. The control circuit 350 is illustrated in position within the lamp support structure 120 in FIG. 16 to illustrate this. Furthermore, the first and second compressible electrical contact elements 351, 352 nest within the depressions 382, 383 (see FIG. 6B) formed into the front wall 381. However, the first and second compressible electrical contacts 351, 352 protrude from the lamp support surface 122 when they are in an uncompressed state (i.e., normal state without any forces acting thereon). As can be seen, the first and second electrical contacts 161, 162 on the lamp 150 are aligned with the first and second compressible electrical contacts 351, 352. Thus, as the lamp 150 comes into contact with the lamp support surface 122 during assembly, the electrical contacts 161, 162 of the lamp 150 come into electrical coupling with the first and second compressible electrical contact elements 351, 352 and cause the compressible electrical contacts 351, 352 to compress. This will be described in more detail below with reference to FIG. 21B.

To couple the lamp 150 to the lamp support structure 120, the upper edge 155 of the flexible sheet body 151 of the lamp 150 is inserted into the upper slot 144 defined between the upper overhang structure 142 and the lamp support surface 122. Similarly, the lower edge 156 of the flexible sheet body 151 of the lamp 150 is inserted into the lower slot 145 defined between the lower overhang structure 143 and the lamp support surface 122. Thus, a portion of the upper edge 155 of the lamp 150 nests within the upper slot 144 and a portion of the lower edge 156 of the lamp 150 nests within the lower slot 145. FIG. 17A provides a close-up view of the upper edge 155 of the lamp 150 being located within the upper slot 144. This holds the lamp 150 in place and snap fits the lamp against the lamp support surface 122. In some embodiments, the lamp 150 may have a pre-defined curvature that biases the lamp 150 against the entirety of the lamp support surface 122. In other embodiments, the lamp 150 may be maintained in a flexed state (i.e., curved as shown) along the lamp support surface 122 due, at least in part, to contact with the upper and lower overhang structures 142, 143. In some embodiments, the lamp 150 is snap-fit to the lamp support structure 120 due to the upper edge 155 of the flexible sheet body 151 flexing and snapping past the upper overhang structure 142 into the upper slot 144 and the lower edge 156 of the flexible sheet body 151 flexing and snapping past the lower overhang structure 143 into the lower slot 145.

As seen in FIG. 17, the edges of the lamp 150 may be retained by the perimetric lamp retaining wall 139 of the lamp support structure 120. In some embodiments, the edges of the lamp 150 may abut against or otherwise be in contact with the perimetric lamp retaining wall 139 or portions thereof, although this is not required in all embodiments. FIG. 17 illustrates the lamp 150 mounted to the lamp support structure 120. When so positioned, the lamp 150 is configured to emit electromagnetic radiation onto oral surfaces when the mouthpiece 100 is positioned within a mouth of a user and activated, as described herein.

Figure 18:
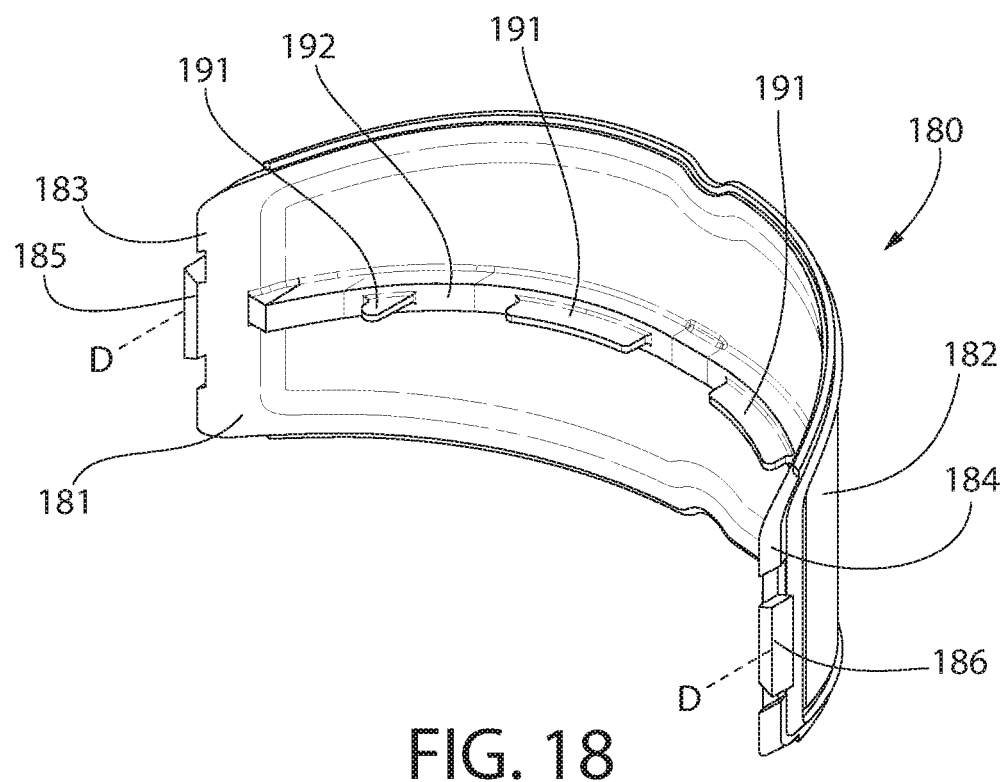
FIG. 18 is a front perspective view of a lens plate of the oral treatment device of FIG. 1 in accordance with an embodiment of the present invention.
Figure 19:
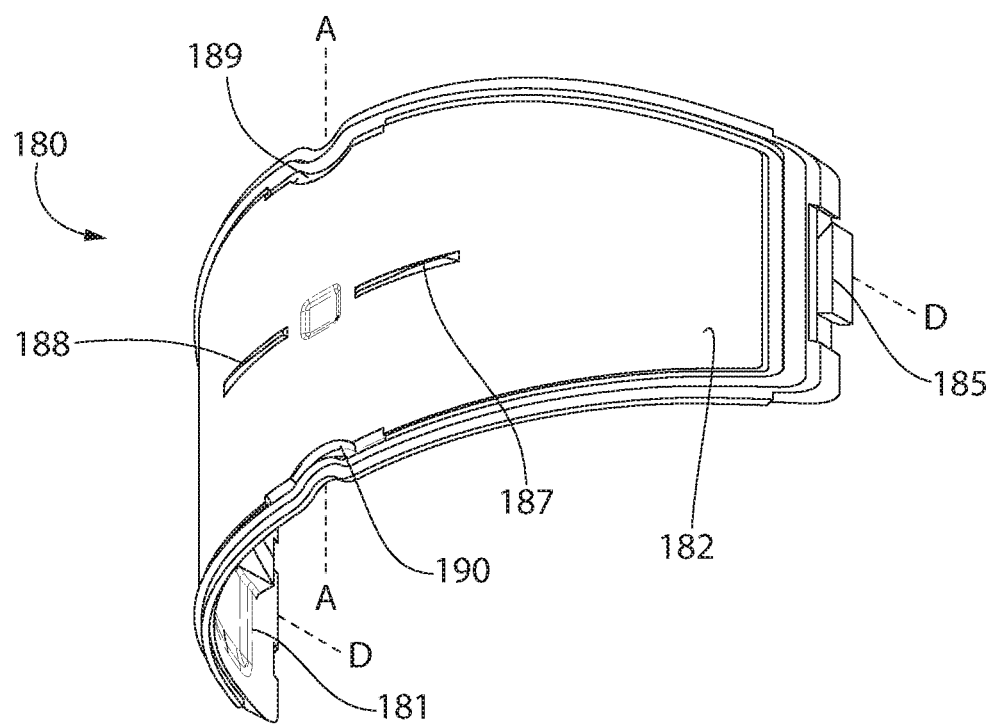
FIG. 19 is a rear perspective view of the lens plate of FIG. 18

Referring to FIGS. 18 and 19, the lens plate 180 will be described. The lens plate 180 may be referred to herein as a curved lens plate or a cover lens plate in various embodiments, but it should be appreciated that all of these terms refer to the same component. However, it should be appreciated that the lens plate 180 is a separate structure from the lamp 150, and therefore a separate structure form the flexible lens plate 159 that forms a part of the flexible sheet body 151 of the lamp 150. When the oral treatment device 1000 is assembled, the lens plate 180 is adjacent to the flexible lens plate 159 of the lamp 150. The lens plate 180 is coupled to the lamp support structure 120 so that the lamp 150 is positioned between the lamp support structure 120 and the lens plate 180. The lens plate 180 comprises a front surface 181 from which the light generated by the lamp 150 is emitted and a rear surface 182 opposite the front surface 181. The rear surface 182 of the lens plate 180 is adjacent to and faces the front surface 152 of the flexible sheet body 151 of the lamp 150. In the exemplified embodiment, the lens plate 180 has a curved shape such that the front surface 181 of the lens plate 180 is concave and the rear surface 182 of the lens plate 180 is convex. Thus, the shape of the lens plate 180 matches the shape of the lamp support surface 122.

Because the lens plate 180 covers the front surface 152 of the flexible sheet body 151 of the lamp 150, the lens plate 180 is formed of a light transmissive material so that the light generated by the light emitters of the lamp 150 can pass through the lens plate 180. Thus, in some embodiments the lens plate 180 may be formed of a transparent material. The lens plate 180 may also be formed of a translucent material. In some embodiments, the lens plate 180 may have a colored tint, while still being light transmissive so that light emitted by the lamp 150 can pass therethrough. In one particular embodiment, the lens plate 180 may be formed of a transparent biocompatible material. The lens plate 180 may be formed of a copolyester. In some embodiments the copolyester is Eastar™ BR003, although the invention is not to be so limited in all embodiments and the lens plate 180 may be formed of a number of different materials so long as it enables the light emitted by the lamp 150 to pass therethrough as described herein. One benefit of Eastar™ BR003 is that it contains a mold release additive and is nearly water-clear.

The lens plate 180 extends along an arcuate longitudinal axis D-D from a first end 183 to a second end 184. The lens plate 180 comprises a first connection element 185 located on the first end 183 and a second connection element 186 located on the second end 184. As will be described in more detail below, the first and second connection features 185, 186 of the lens plate 180 mate with the first and second connection features 140, 141 of the lamp support structure 120 to couple the lens plate 180 to the lamp support structure 120.

The lens plate 180 comprises a first protuberance 187 and a second protuberance 188 extending from the rear surface 182 in a spaced apart manner. In the exemplified embodiment, each of the first and second protuberances 187, 188 is located on the arcuate longitudinal axis D-D of the lens plate 180. Furthermore, the first and second protuberances 187, 188 are spaced apart from one another along the arcuate longitudinal axis D-D. Although two of the protuberances 187, 188 are depicted in the exemplified embodiment, it is possible that only one protuberance or more than two protuberances could be used in alternative embodiments. In one particular embodiment, the first and second protuberances 187, 188 could be connected to form a single, longer protuberance.

In the exemplified embodiment, each of the first and second protuberances 187, 188 is elongated in a direction that extends between the first and second ends 183, 184 of the lens plate 180. However, the invention is not to be particularly limited by the shape of the first and second protuberances 187, 188 in all embodiments. Thus, the first and second protuberances 187, 188 could take on other shapes while still being able to achieve the desired function, described in more detail herein below. For example, the first and second protuberances 187, 188 could be nubs that extend form the rear surface 182 without being elongated. When the oral treatment device 1000 is assembled, the first and second protuberances 187, 188 are aligned with the first and second electrical contacts 161, 172 on the rear surface 153 of the flexible sheet body 151 of the lamp 150 to press them into contact with the first and second compressible electrical contacts 351, 352 of the control circuit 350.

The lens plate 180 also comprises an upper recess 189 and a lower recess 190 that are aligned with one another along the dental arch midline plane A-A. Each of the upper and lower recesses 189, 190 are formed into the rear surface 182 of the lens plate 180, which is the surface that faces the lamp support surface 122 when the mouthpiece 100 is assembled as described herein. The upper and lower recesses 189, 190 have a shape that corresponds with the shape of the upper and lower overhang structures 142, 143 so that the upper and lower overhang structures 142, 143 of the lamp support structure 120 nest within the upper and lower recesses 189, 190 of the lens plate 180 when those two components are coupled together.

The upper and lower recesses 189, 190 may form alignment elements of the lens plate 180 and the upper and lower overhang structures 142, 143 may form alignment elements of the lamp support structure 120. In that way, the upper and lower recesses 189, 190 of the lens plate 180 and the upper and lower overhang structures 142, 143 of the lamp support structure 120 may mechanically mate with one another (by the upper and lower overhang structures 142, 143 being received within the upper and lower recesses 189, 190) to maintain the lens plate 180 and the lamp support structure 120 in relative alignment with one another. Thus, in the exemplified embodiment it is recesses (i.e., the upper and lower recesses 189, 190) of the lens plate 180 that mate with protrusions (i.e., the upper and lower overhang structures 142, 143) of the lamp support structure 120 to provide the alignment function. The invention is not to be so limited in all embodiments. In other embodiments, the lens plate 180 may be protrusions that interact/mate with recesses in the lamp support structure 120 to achieve the alignment. In other embodiments, these "alignment" elements may be omitted and alignment may be achieved by properly coupling the connection features 140, 141 of the lamp support structure 120 to the connection features 185, 186 of the lens plate.

In the exemplified embodiment, the lens plate 180 further comprises a plurality of protuberances 191 protruding from the front surface 181. More specifically, the lens plate 180 comprises a ridge 192 extending from the front surface 181 of the lens plate 180 along the arcuate longitudinal axis D-D. The plurality of protuberances 191 are located on and extend from the ridge 192 in a direction away from the front surface 181. The plurality of protuberances 191 are spaced apart along the arcuate longitudinal axis A-A. In the exemplified embodiment, there are four of the protuberances 191. However, any number of the protuberances 191 may be present in various alternative embodiments. In fact, it may be possible to properly manufacture the oral treatment device 1000 without including the protuberances 191 on the front surface 181 of the lens plate 180 and thus those protuberances 191 may be omitted in some embodiments.

In the exemplified embodiment, the protuberances 191 that extend from the front surface 181 of the lens plate 180 are aligned with the protuberances 187, 188 that extend from the rear surface 182 of the lens plate 180. Thus, at least one of the protuberances 191 on the front surface 181 of the lens plate 180 is aligned with/overlaps at least one of the protuberances 187, 188 on the rear surface 182 of the lens plate 180 In fact, in the exemplified embodiment the protuberances 191 on the front surface 181 and the protuberances 187, 188 on the rear surface 182 are all located on the arcuate longitudinal axis D-D. However, it should be appreciated that the protuberances 191 need not be aligned with the protuberances 187, 188 in all embodiments, although such alignment may facilitate a secure electrically coupling between the first and second electrical contacts 161, 162 of the lamp 150 of the first and second compressible electrical contacts 351, 352 of the control circuit 350.

Figure 20:
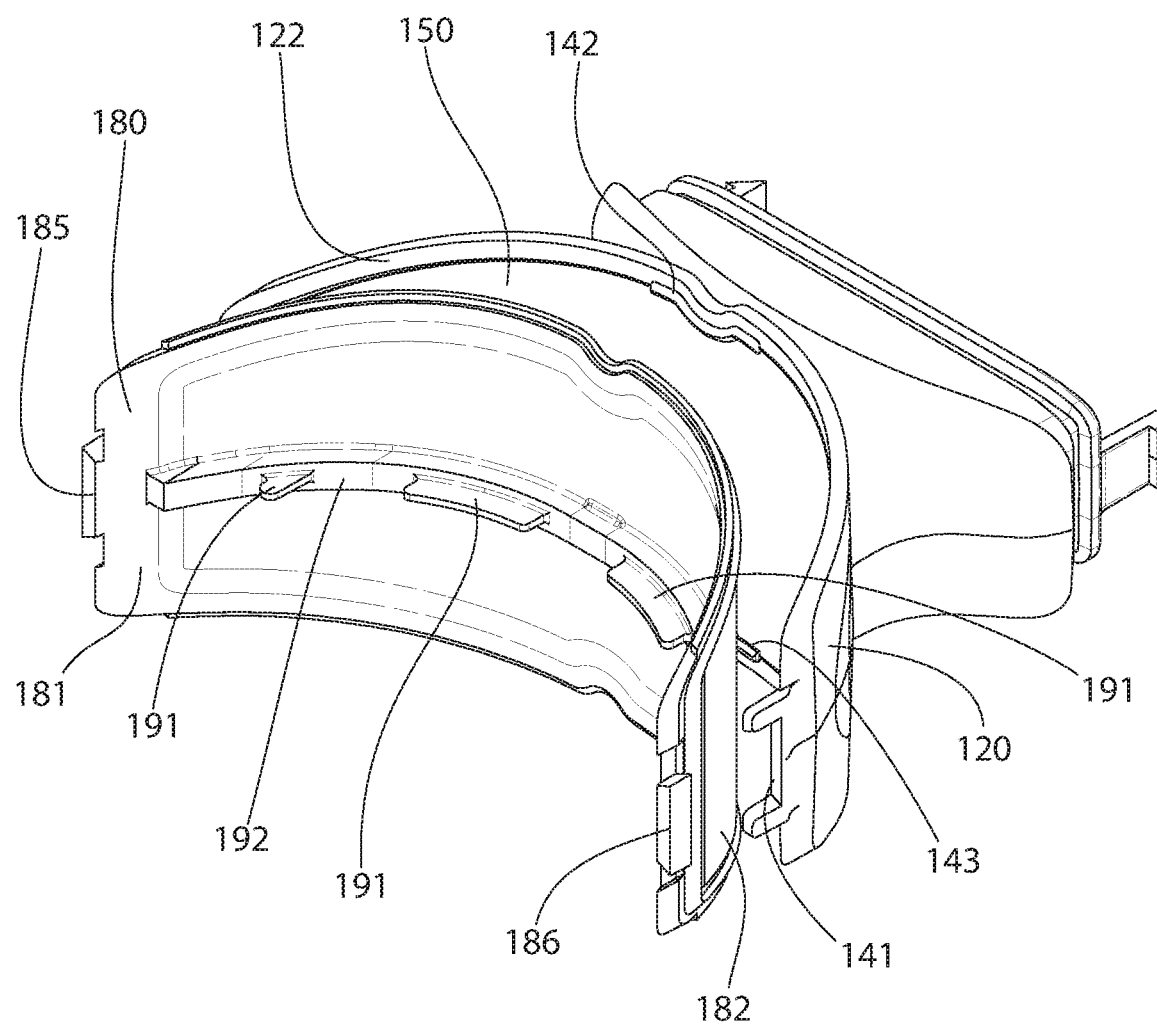
FIG. 20 is a front perspective view illustrating the lens plate adjacent to the assembled lamp and lamp support structure in preparation for being coupled thereto.
Figure 21:
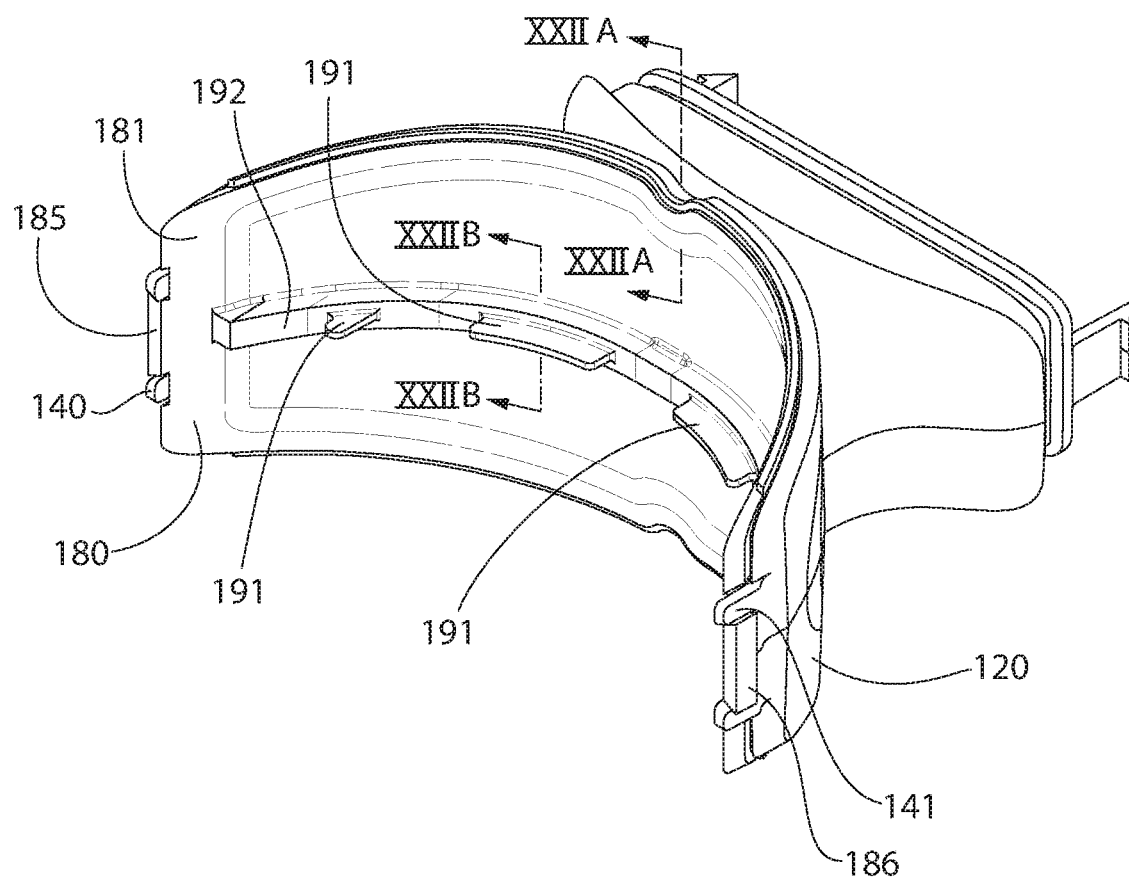
FIG. 21 is a front perspective view illustrating the lens plate, the lamp, and the lamp support structure coupled together in an assembled state.
Figure 21A:
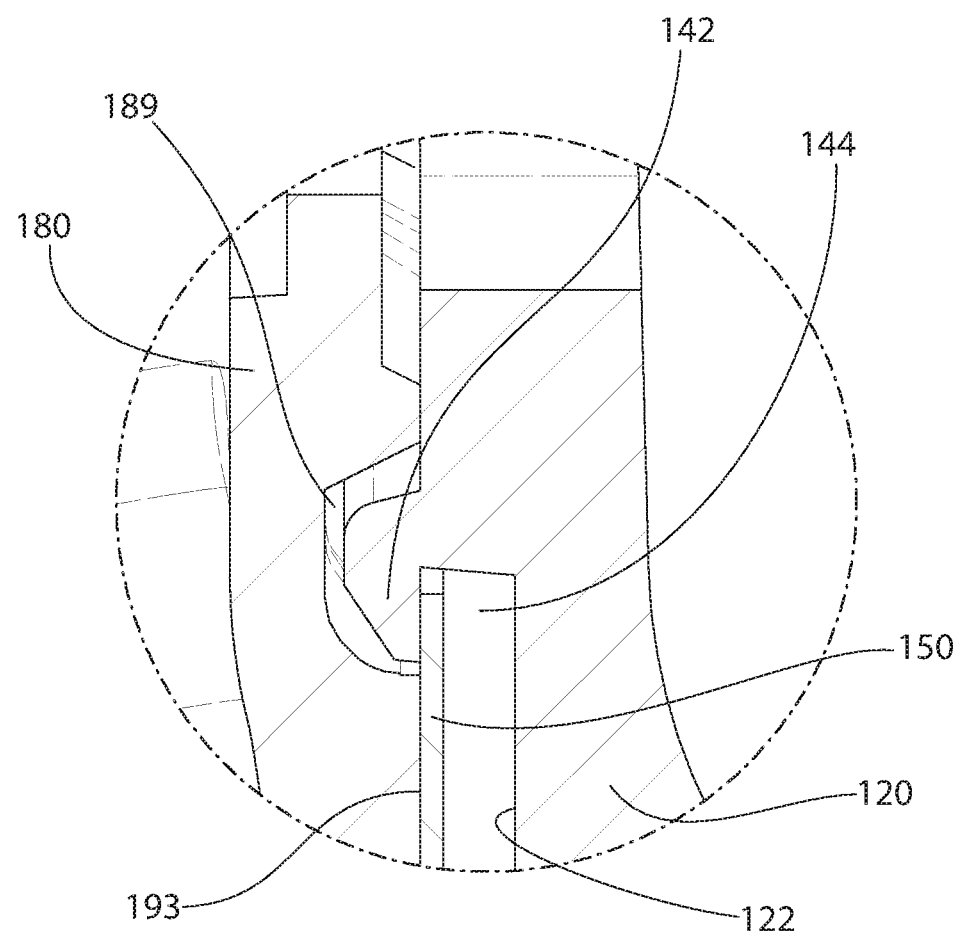
FIG. 21A is a cross-sectional view taken along line XXIA-XXA of FIG. 21.

Referring to FIGS. 20-21A, the coupling of the lens plate 180 to the lamp support structure 120 with the lamp 150 already coupled thereto will be described. The lens plate 180 is positioned with its rear surface 182 facing the lamp support surface 122 of the lamp support structure 120 and the lamp 150. The lens plate 180 is then moved towards the lamp support structure 120 until the first and second connection elements 185, 186 of the lens plate 180 are received between the legs of the first and second connection elements 140, 141 of the lamp support structure 120. The engagement and mating of the connection elements 185, 186 of the lens plate 180 with the connection elements 140, 141 of the lamp support structure 120 physically/mechanically couple the lens plate 180 to the support structure 120. Furthermore, as the lens plate 180 is moved towards the lamp support structure 120, the upper and lower overhang structures 142, 143 of the lamp support structure 120 enter into and nest within the upper and lower recesses 189, 190 on the rear surface 182 of the lens plate 180.

Figure 25:
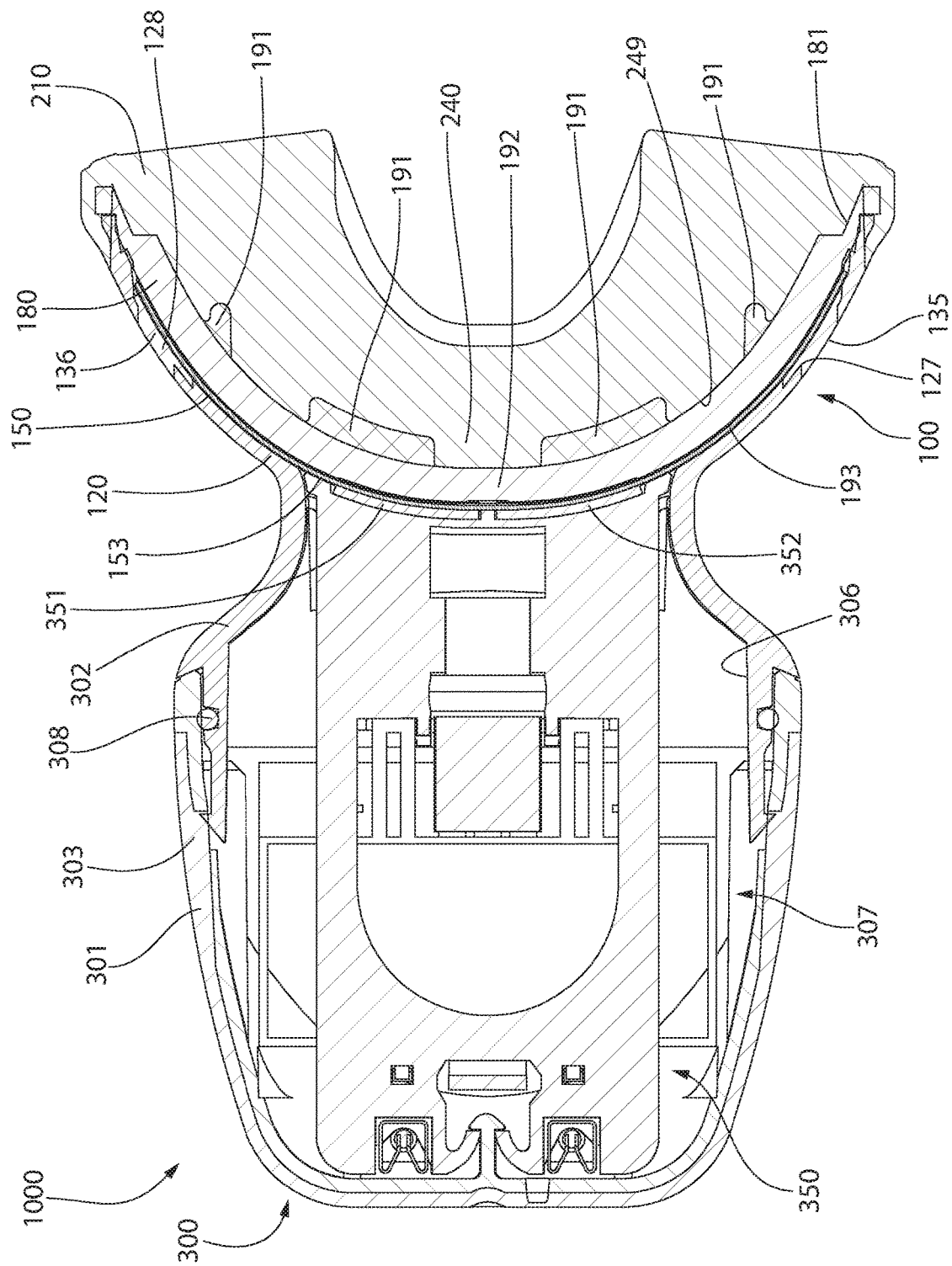
FIG. 25 is a cross-section taken along line XXV-XXV of FIG. 3.

Referring to FIGS. 21A, 24 and 25, when the lens plate 180 is coupled to the lamp support structure 120, the lens plate 180 overlies the front surface 152 of the flexible sheet body 151 of the lamp 150 so that the lens plate 180 is adjacent to the flexible lens plate 159 of the lamp 150. In this way, a lamp-cover interface 193 is formed between the flexible lens plate 159 of the lamp 150 and the lens plate 180. The flexible lens plate 159 of the lamp 150 is formed of a material having a first refractive index and the lens plate 180 is formed of a material having a second refractive index, with the second refractive index being less than the first refractive index. During operation, the light generated by the light emitters 154 passes through the flexible lens plate 159 of the lamp 150 and through the lens plate 180 prior to exiting the oral treatment device 1000. In the exemplified embodiment, the lens plate 180 and the lamp 150 have the same curved profile. Furthermore, the lens plate 180 and the lamp 150 are straight (i.e., perpendicular to the horizon) rather than being angled.

In some embodiments, a ratio of the second refractive index to the first refractive index is at least 0.8:1 and in other embodiments the ratio of the second refractive index to the first refractive index is at least 0.9:1. In some embodiments, the first refractive index may be in a range of 1.6 to 1.8, and more specifically in a range of 1.6 to 1.7. In some embodiments, the second refractive index may be in a range of 1.45 to 1.65, and more specifically in a range of 1.5 to 1.6. In some embodiments, an oral treatment material that is intended for use with the oral treatment device 1000 may couple the lens plate 180 to the oral surface to be treated (see element 400 in FIGS. 27A-29). The oral treatment material may have a third refractive index that is less than the second refractive index. In some embodiments, the third refractive index may be in a range of 1.3 to 1.5 and a ratio of the third refractive index to the second refractive index of the lens plate 180 may be at least 0.8:1. The oral treatment material may be a tooth whitening gel and the light emitted by the plurality of light emitters 154 may have a wavelength in a range of 380 nm to 500 nm, or more specifically 400 nm to 420 nm, as noted above.

Figure 21B:
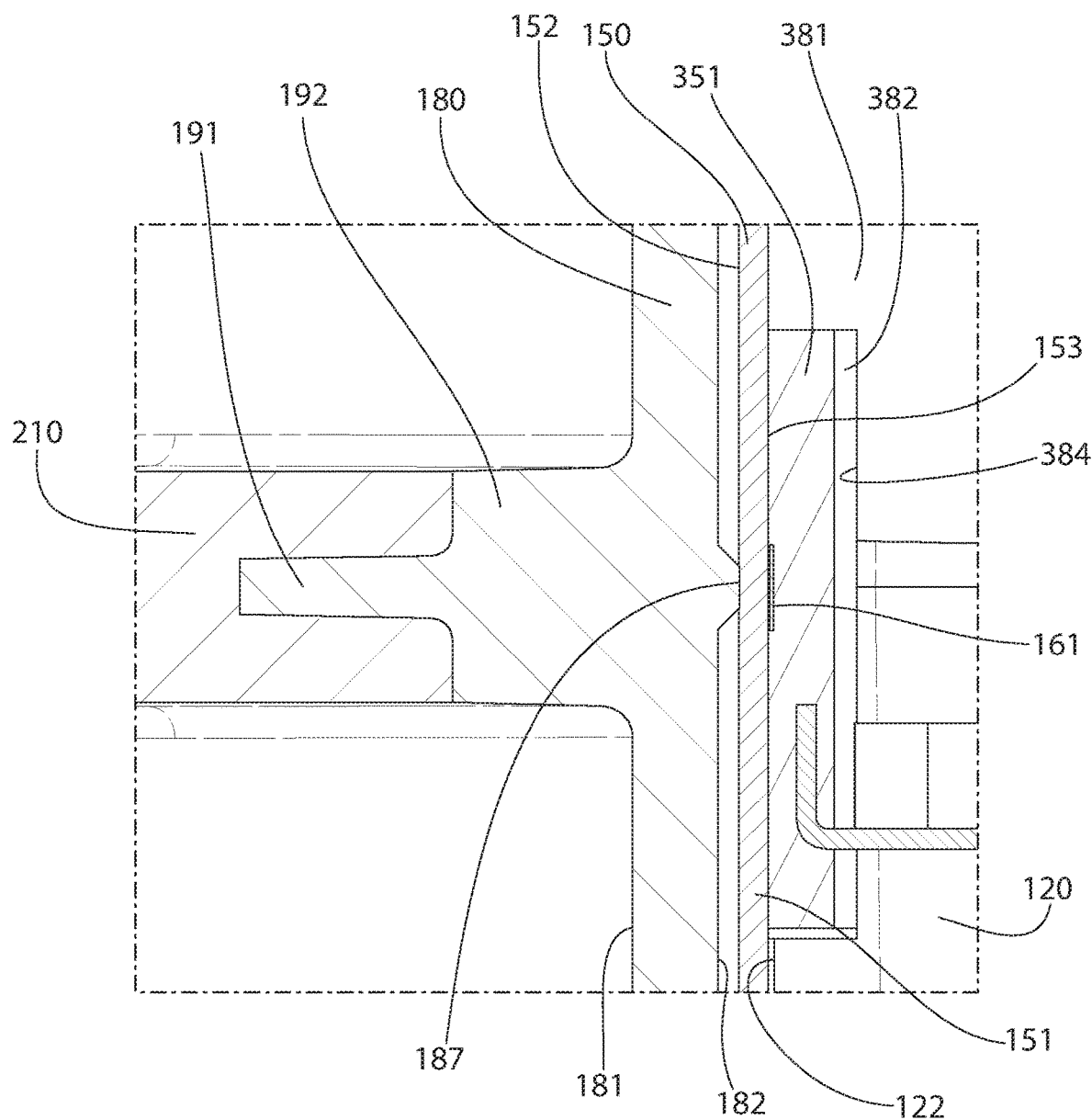
FIG. 21B is a cross-sectional view taken along line XXIB-XXIB of FIG. 21.

Referring to FIG. 21B, the relationship between the lens plate 180, the lamp 150, the first and second electrical contacts 161, 162 of the lamp 150, and the first and second compressible electrical contacts 351, 352 of the control circuit 350 will be described. The lamp support surface 122 comprises two depressions 382, 383, each of which are formed into the front wall 381 of the actuation unit 380 as described above. Specifically, because the front wall 381 of the actuation unit 380 forms a portion of the lamp support surface 122, the depressions 382, 383 formed into the front wall 381 of the actuation unit 380 are also depressions in the lamp support surface 122. The floor 384 of the depressions 382, 383 forms a wall surface upon which the first and second compressible electrical contacts 351, 352 may be compressed in the assembled oral treatment device 1000. As mentioned previously, the first and second compressible electrical contacts 351, 352 are located within the depressions 382, 383 and protrude out from the lamp support surface 122 in their normal, non-compressed state.

The lamp 150 is then coupled to the lamp support structure 120 adjacent to the lamp support surface 122 so that the rear surface 153 of the flexible sheet body 151 is in contact with the lamp support surface 122. When so positioned, the electrical contacts 161, 162 of the lamp 150 are aligned with the compressible electrical contacts 351, 352 of the control circuit 350. Next, the lens plate 180 is coupled to the lamp support structure 120 as described above so that the rear surface 182 of the lens plate 180 is adjacent to the front surface 152 of the flexible sheet body 151 of the lamp 150. As noted above, the protuberances 187, 188 extending from the rear surface 182 of the lens plate 180 are aligned with the first and second electrical contacts 161, 162 of the lamp 150 and the first and second compressible electrical contacts 351, 352 of the control circuit 350. Thus, when the lens plate 180 is coupled to the lamp support structure 120, the protuberances 187, 188 press the flexible sheet body 151 of the lamp 150, and more specifically the first and second electrical contacts 161, 162 of the lamp 150, against the first and second compressible electrical contacts 351, 352, thereby causing the first and second compressible electrical contacts 351, 352 to compress. In FIG. 21B, the first and second electrical contacts 351, 352 (only the first electrical contact 351 is illustrated, but the same occurs with the second electrical contact 351) are in a compressed state due to the contact with the first and second electrical contacts 161, 162 of the lamp 150. Thus, the one or more protuberances 187, 188 of the lens plate 180 compress the first and second compressible contacts 351, 352 between the flexible sheet body 151 of the lamp 150 and a wall surface, said wall surface being formed by the floor 384 of the depressions 382, 383.

Figure 22:
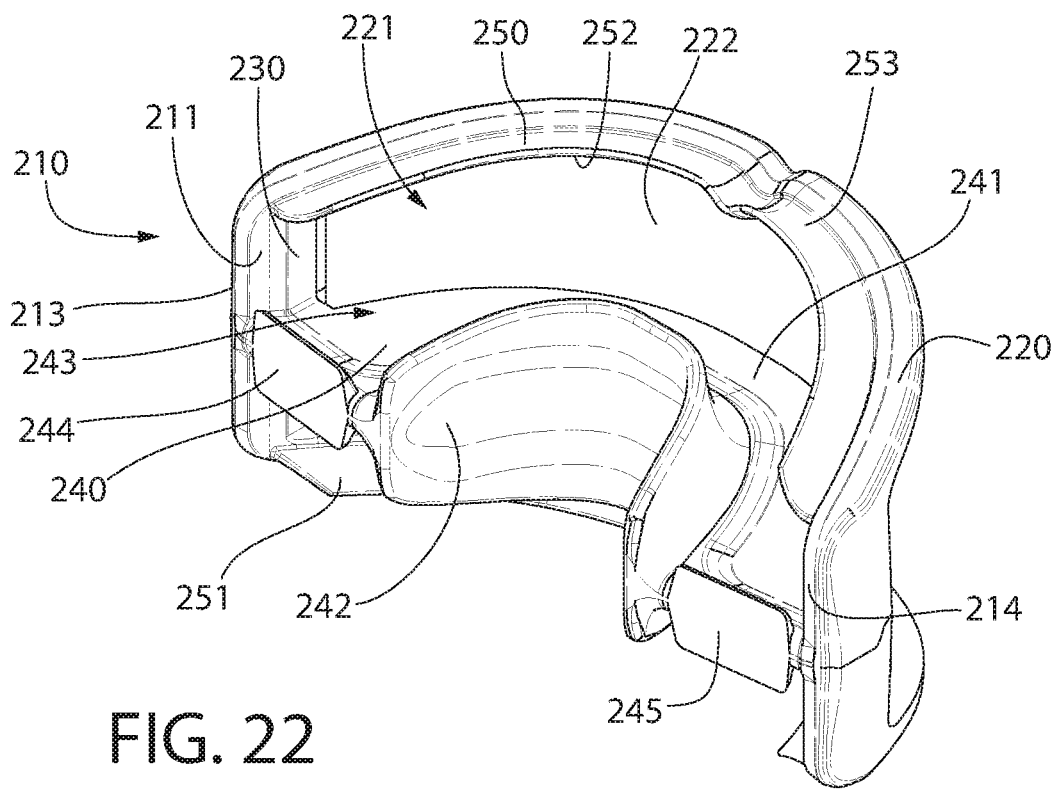
FIG. 22 is a front perspective view of a guard component of the oral treatment device of FIG. 1 in accordance with an embodiment of the present invention.
Figure 23:
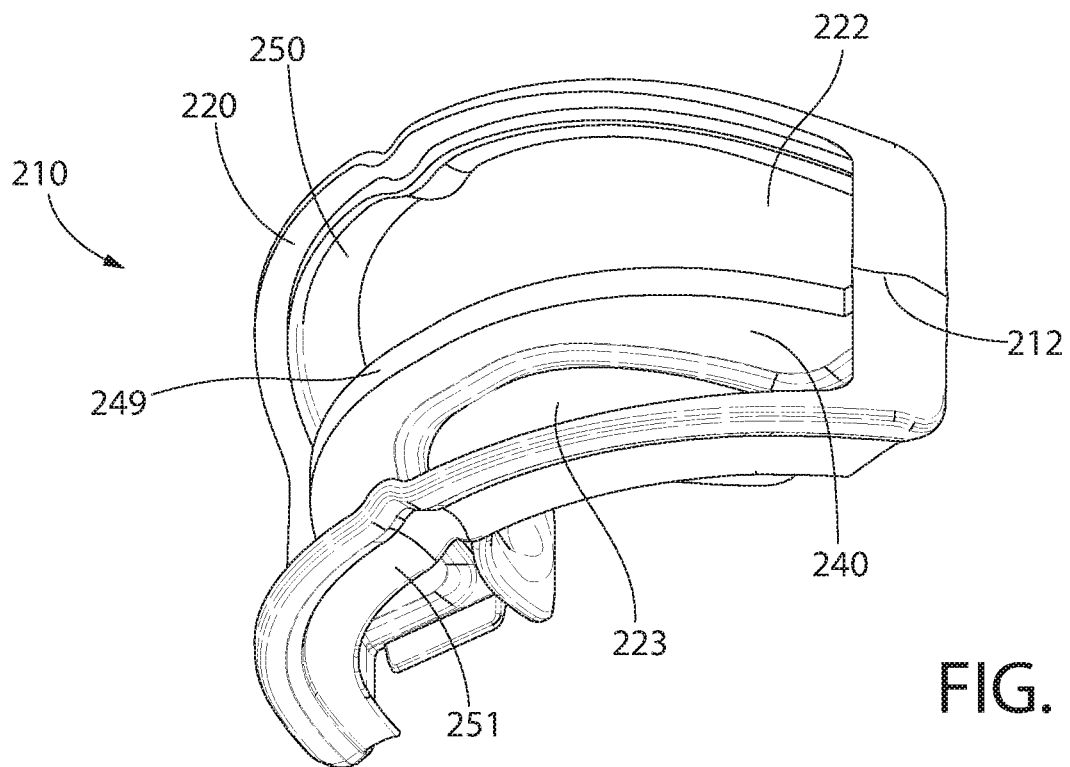
FIG. 23 is a rear perspective view of the guard component of FIG. 22.
Figure 23A:
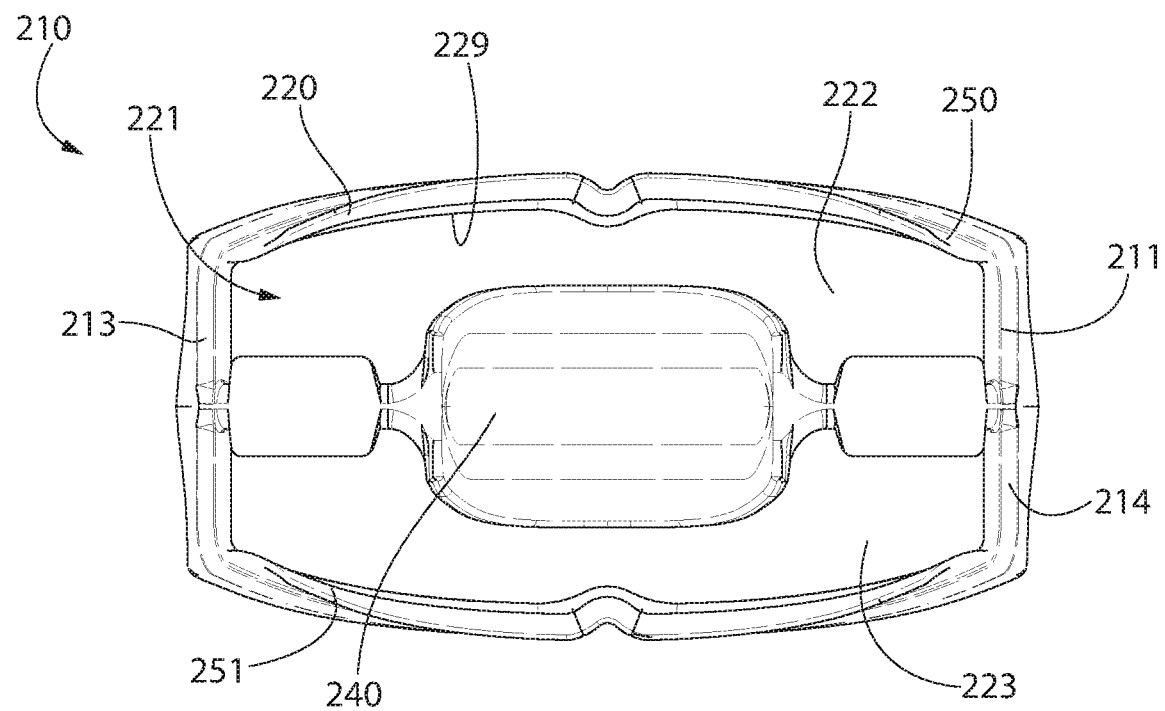
FIG. 23A is a front view of the guard component if FIG. 22.

Referring to FIGS. 22, 23, and 23A, the guard component 210 of the mouthpiece 100 will be described. As mentioned above, the guard component 210 may be formed of a resilient material such as a thermoplastic elastomer or other elastomeric material. Suitable elastomeric materials include, without limitation, thermoplastic elastomers, rubbers, silicones, or other biocompatible resilient materials suitable for uses in an oral hygiene apparatus including thermoset elastomers or the like. The reason for forming the guard component 210 out of an elastomeric material is that the guard component 210 is the main component that directly contacts the user's oral cavity surfaces during use of the oral treatment device 1000. Thus, forming the guard component 210 out of an elastomeric material enhances comfort to the user. The guard component 210 may be injection molded onto the lamp support structure 120 after the lamp 150 and the lens plate 180 are coupled to the lamp support structure 120 to complete the assembly of the mouthpiece 100. Alternatively, the guard component 210 could be formed separately from the lamp support structure 120 and merely coupled thereto using mechanical interfaces/mating between the components.

The guard component 210 has a front surface 211 and a rear surface 212 opposite the front surface 211. The guard component 210 extends from a first side end 213 to a second side end 214 and is generally arcuate in its extension from the first side end 213 to the second side end 214. The guard component 210 is coupled to the lamp support structure 120 with the rear surface 212 facing the lens plate 180, the lamp 150, and the lamp support surface 122. The guard component 210 generally comprises a frame 220, a wall portion 230, and a bite plate portion 240 that forms at least a part, if not the entirety, of the bite platform 104 of the mouthpiece 100.

The frame portion 220 defines a window 221 that is divided by the bite plate portion 240 into an upper window 222 and a lower window 223. The frame 220 forms an enclosed geometric structure having an arcuate shape that appears rectangular when viewed from the front (see FIG. 23A). The frame portion 220 has an inner surface 229 that forms the bounds of the upper and lower windows 222, 223. The upper and lower windows 222, 223 are openings through which the lens plate 180 is exposed in the assembled mouthpiece 100. Thus, electromagnetic radiation emitted by the lamp 150 can pass through the lens plate 180 and through the upper and lower windows 222, 223 to reach a user's teeth and other oral surfaces as desired. More specifically, the electromagnetic radiation emitted by the first and second upper illumination zones 167, 168 of the lamp 150 pass through the upper window 222 and the electromagnetic radiation emitted by the first and second lower illumination zones 169, 170 of the lamp 150 pass through the lower window 223.

As noted above, the bite plate portion 240 of the guard component 210 may in certain embodiments form the entirety of the bite platform 104 of the mouthpiece 100. Thus, as shown in the exemplified embodiment, the bite plate portion 240 of the guard component 210 comprises a horizontal portion 241 that extends horizontally form the wall portion 230 of the guard component 210 and a vertical portion 242 that extends both upwardly and downwardly from the horizontal portion 241. Upper and lower channels 243 (only the upper channel is visible in FIGS. 22 and 23) are defined between the wall portion 230 and the vertical portion 242 of the horizontal portion 241. Stopper elements 244, 245 are provided at the ends of the upper and lower channels 243 that will be adjacent to a user's back-most teeth during use. The stopper elements 244, 245 may ensure that any whitening or other agents provided in the upper and lower channels 243 remain therein during use.

Because the bite platform 104 is formed entirely from the guard component 210 in the exemplified embodiment, the bite platform 104 is formed from an elastomeric material as described herein. During use, the bite platform 104 is located between the user's upper and lower teeth and thus the user may bite down on the bite platform 104. Forming the bite platform 104 entirely out of an elastomeric material may be advantageous in that it will not damage a user's teeth if they happen to bite down with great force.

The guard component 210 also comprises an upper gum guard 250 and a lower gum guard 251. The upper gum guard 250 extends from the frame 220 along an upper edge thereof and the lower gum guard 251 extends from the frame 220 along a lower edge thereof. The upper gum guard 250 has an inner surface 252 that faces the bite plate portion 240 and an outer surface 253 that faces away from the bite plate portion 240. In the exemplified embodiment, the inner surface 252 of the upper gum guard 250 is convex and the outer surface 253 of the upper gum guard 250 is concave. Similarly, the lower gum guard 251 has an inner surface 254 that faces the bite plate portion 240 and an outer surface 255 that faces away from the bite plate portion 240 (best shown in FIG. 26). In the exemplified embodiment, the inner surface 254 is convex and the outer surface 255 is concave. During use, the upper gum guard 250 may pivot upwardly relative to the frame 220 while the lower gum guard 251 may pivot downwardly relative to the frame 220 to cover a greater surface area of the gums for protection thereof (see FIGS. 28 and 29).

Figure 26:
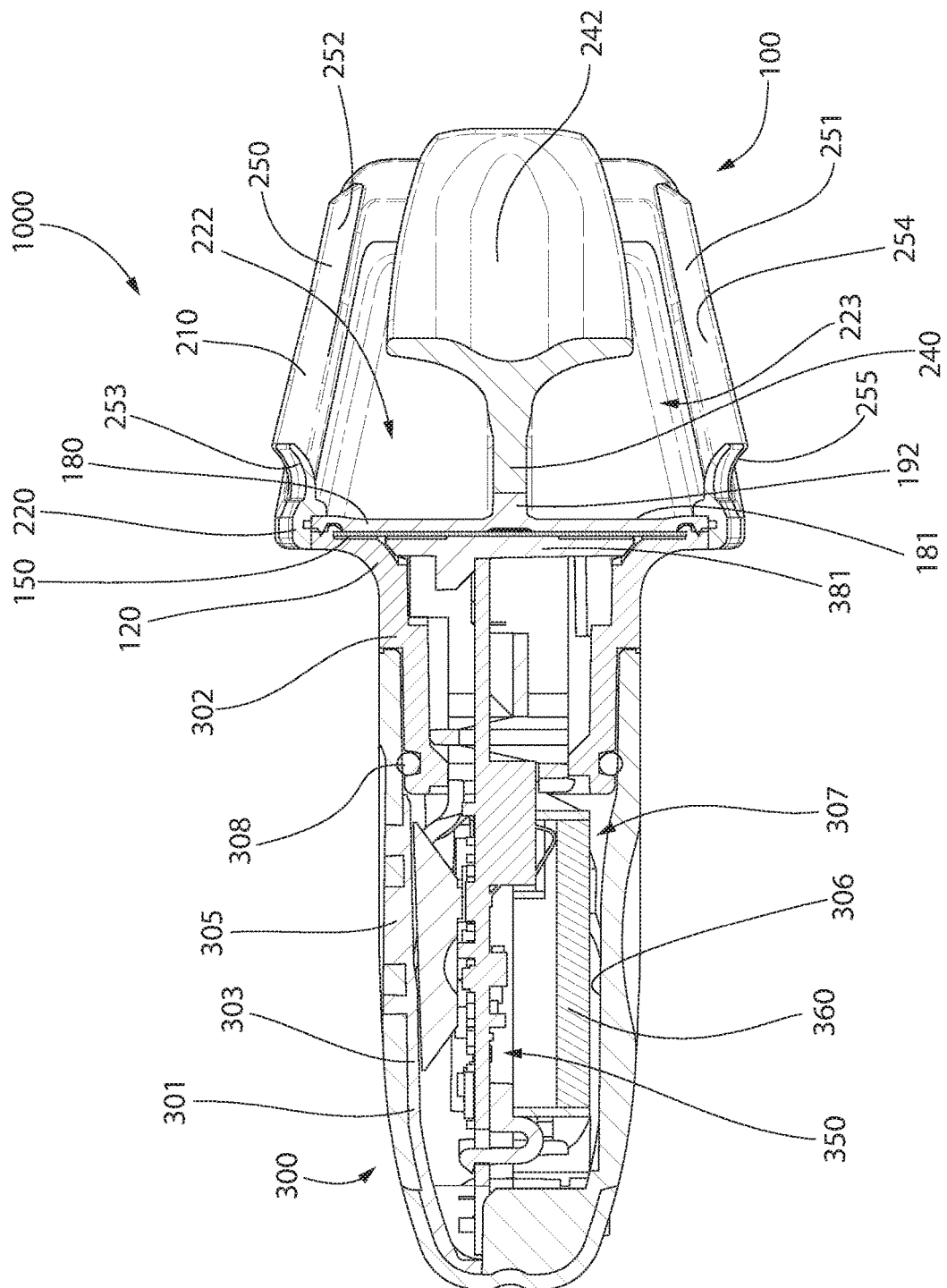
FIG. 26 is a cross-section taken along line XXVI-XXVI of FIG. 3.

As can be seen in FIGS. 24-26, the guard component 210 is coupled to the lamp support structure 120 and seals the lamp 150 in a fluid tight manner between the lens plate 180 and the lamp support structure 120. The guard component 210 covers a perimeter region of the front surface 181 of the lens plate 180 to prevent liquid (i.e., water, saliva, whitening material, etc.) from penetrating through the guard component 210 and contacting the lamp 150 or other electronic components of the oral treatment device 1000. Furthermore, because the guard component 210 is injection molded onto the lamp support structure 120 during manufacturing in the exemplified embodiment, the protuberances 191 extending from the front surface 181 of the lens plate 180 extend into the bite plate portion 240 of the guard component 210 during the injection molding process. Specifically, the protuberances 191 extending from the front surface 181 of the lens plate 180 extend into a rear surface 249 of the bite platform 240 of the guard component 210. This is best seen in FIGS. 21B and 25. This creates a strong bond between the guard component 210 and the lens plate 180 and prevents upward and downward movement of the guard component 210 relative to the lens plate 180 and the remainder of the mouthpiece 100. Even without injection molding, this same structural arrangement can be achieved by forming recesses into the rear surface 249 of the bite platform 240 within which the protuberances 191 extending from the front surface 181 of the lens plate 180 can nest when the guard component 210 is coupled to the remainder of the mouthpiece 100.

Furthermore, as best seen in FIG. 26, a portion of the frame 220 of the guard component 210 directly covers a portion of the front surface 181 of the lens plate 180 along the upper and lower edges and opposing side edges thereof (i.e., along a perimeter region as noted above) to securely retain the lens plate 180 in place between the guard component 210 and the lamp 150/lamp support structure 120. Thus, the guard component 210 directly covers a perimetric portion of the front surface 181 of the lens plate 180. As best shown in FIGS. 24 and 25, the guard component 210 may also wrap around portions of the lamp support structure 120 to the rear surface of the curved support plate 121 to achieve a good, secure coupling between the guard component 210 and the lamp support structure 120.

Referring to FIGS. 1 and 24-26, the oral treatment device 1000 is illustrated in its entirety and in various cross-sections. In these collective views, it can be readily seen that the first portion 302 of the housing 301 formed by the lamp support structure 120 and the second portion 303 of the housing 301 formed by the handle 300 are coupled together to form the enclosed housing 301. The first and second portions 302, 303 of the housing 301 may have coupling elements that facilitate the coupling of the first and second portions 302, 303 of the housing 301 together. Such coupling elements may include mating indents/detents, protuberances/recesses, clips, hooks, or other mechanical coupling members that are configured to mate/interact with one another to couple the components together.

The enclosed housing 301 has an inner surface 306 that defines a cavity 307 within which the control circuit 350 is located. The housing 301 should be completely enclosed and preferably hermetically sealed to prevent water or other liquids from penetrating into the cavity 307, which could cause damage to the control circuit 350 housed therein. The oral treatment device 1000 may include a gasket 308 that is positioned between the first portion 302 of the housing 301 and the second portion 303 of the housing 301 to ensure that the cavity 307 is a sealed interior space. As can be seen in these views, the handle 300 extends from the convex rear surface 102 of the mouthpiece 100 along the dental arch midline plane A-A such that the handle 300 is fixed to the central portion 124 of the curved support plate 121 of the lamp support structure 120.

To reiterate, the first and second compressible electrodes 351, 352 are operably coupled to the power source 360. Furthermore, the first and second electrodes 161, 162 on the rear surface 153 of the lamp 150 are in direct contact with the first and second compressible electrodes 351, 352, thereby electrically coupling the lamp 150 to the power source 360. The protuberances 191 extending from the front surface 181 of the lens plate 180 apply pressure onto the front surface 152 of the lamp 150, which forces the first and second electrodes 161, 162 of the lamp 150 to compress the first and second compressible electrodes 351, 352 as described above. Once the oral treatment device 1000 is activated by pressing a power button or the like, power is transmitted from the power source 360 to the lamp 150 so that the light emitters 154 of the lamp 150 can emit electromagnetic radiation from the front surface 152 of the lamp 150, through the lens plate 180, and through the upper and lower windows 222, 223 of the guard component 210. In this manner, the electromagnetic radiation can be emitted onto teeth or the like that are located within the first and second channels 108, 109 of the oral treatment device 1000.

Figure 27A:
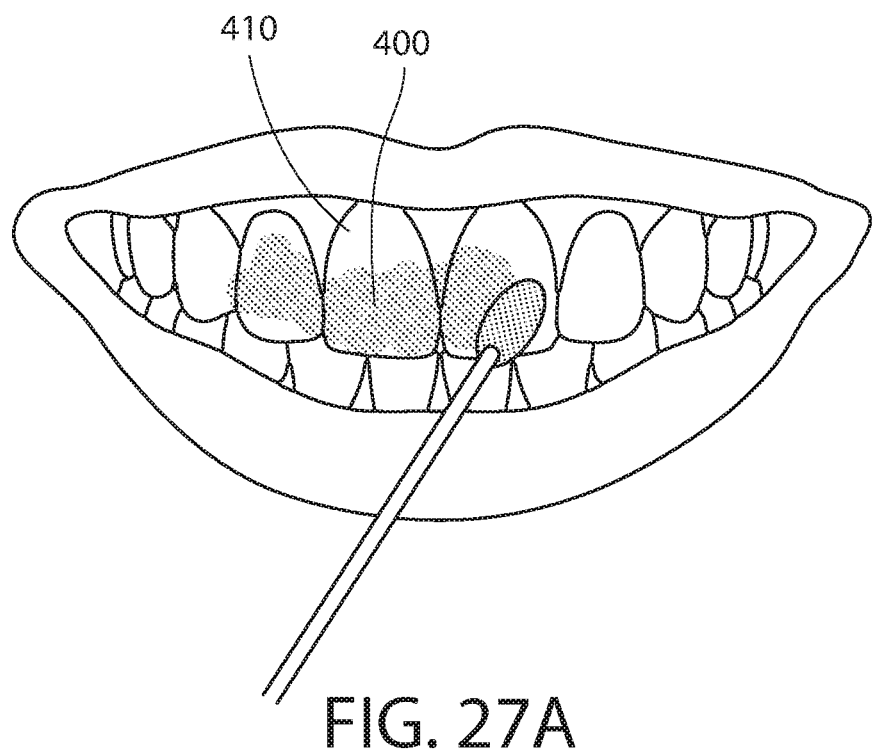
FIG. 27A illustrates applying a teeth whitening material to facial surfaces of a set of teeth in accordance with one embodiment of a method of whitening facial surfaces of a user's teeth.
Figure 27B:
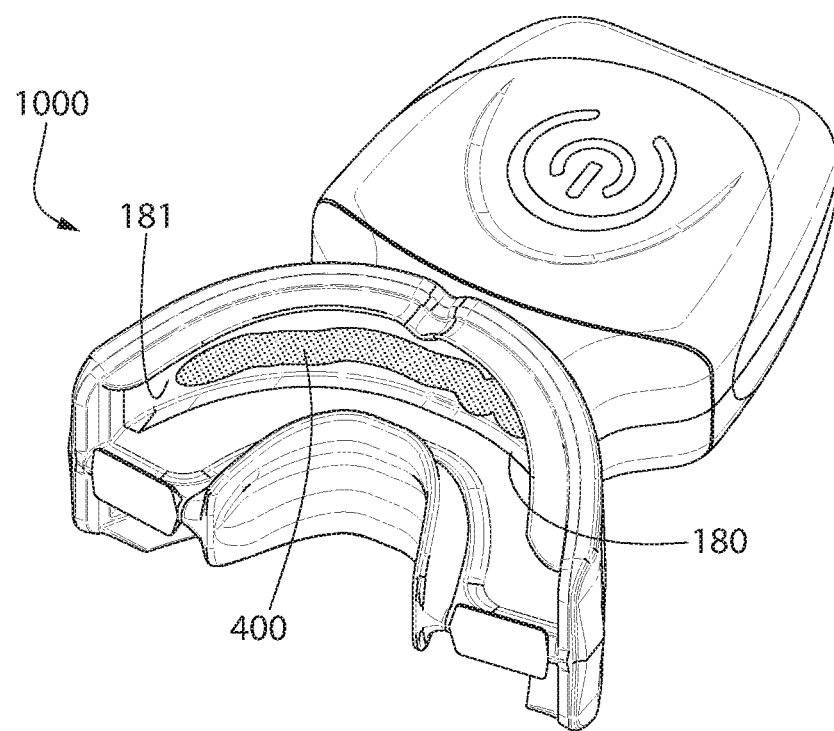
FIG. 27B illustrates applying a teeth whitening material to the oral treatment device of FIG. 1 in accordance with another method of whitening facial surfaces of a user's teeth.

Referring to FIGS. 27A-29, a method of whitening facial surfaces of a user's teeth using the oral treatment device 1000 described herein will be described. FIGS. 27A and 27B illustrate alternative possibilities for the first step in the process. Specifically, the method may comprise applying a teeth whitening material 400 having the third refractive index (described above) to the facial surfaces of a user's teeth 410, as shown in FIG. 27A. This can be achieved using a brush, an applicator, a finger, or the like. Alternatively, the method may comprise applying the teeth whitening material 400 having the third refractive index to the front surface 181 of the lens plate 180 of the oral treatment device 1000. In yet another embodiment, the teeth whitening material 400 may be applied to both the facial surfaces of the user's teeth 410 and to the front surface 181 of the lens plate 180 of the oral treatment device 1000.

Figure 28:
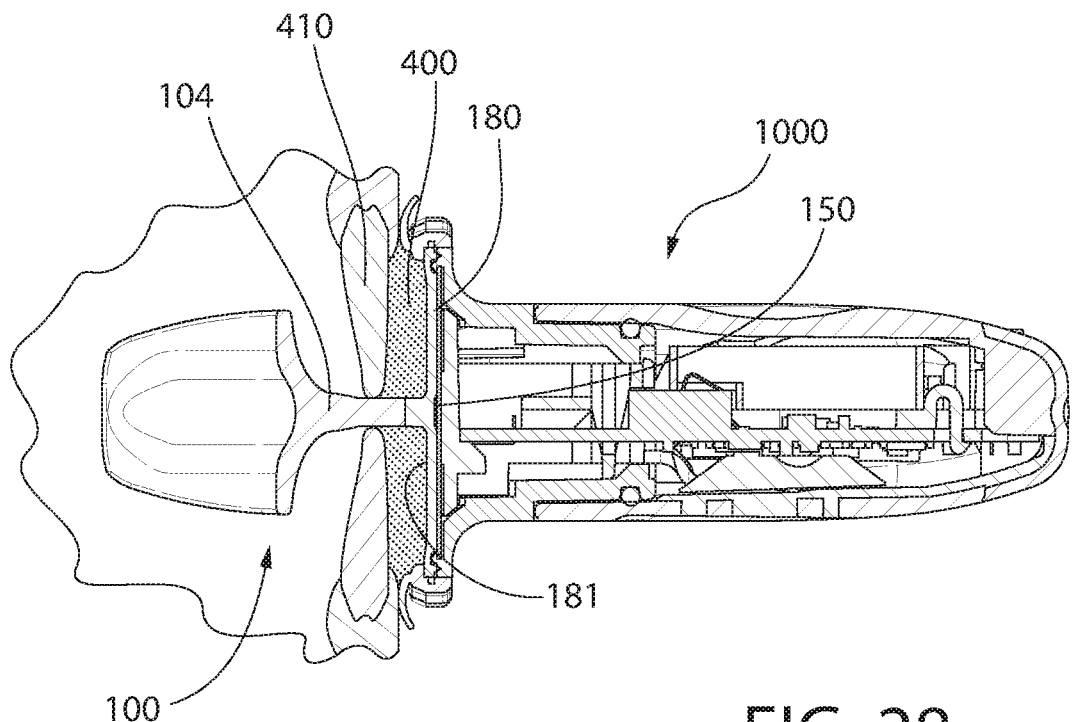
FIG. 28 is a schematic cross-sectional view illustrating the oral treatment device of FIG. 1 placed within a user's oral cavity with the teeth whitening material located between the teeth and the device.

Referring now to FIG. 28, the next step is to position the oral treatment device 1000 within the user's mouth so that the facial surfaces of the user's teeth 410 are adjacent to the front surface 181 of the lens plate 180 of the oral treatment device 1000. During this step, the teeth whitening material 400 may be positioned so that it contacts the teeth 410 and the front surface 181 of the lens plate 180 simultaneously. This may be important in some embodiments to ensure that the electromagnetic radiation is able to be properly emitted onto the teeth. Specifically, because the lamp 150 has a first refractive index, the lens plate 180 has a second refractive index that is less than the first refractive index, and the teeth whitening material 400 has a third refractive index that is less than the second refractive index, having all of these components/materials in contact with one another ensures a proper emission of the electromagnetic radiation from the lamp 150 to the teeth 410. Of course, this is not required in all embodiments and in some other embodiments the teeth whitening material 400 may be located on the facial surfaces of the user's teeth 410 but not also in contact with the lens plate 180. In such an embodiment, the light or electromagnetic radiation being emitted from the lamp 150 will still contact the teeth whitening material 400 to increase its effectiveness.

Figure 29:
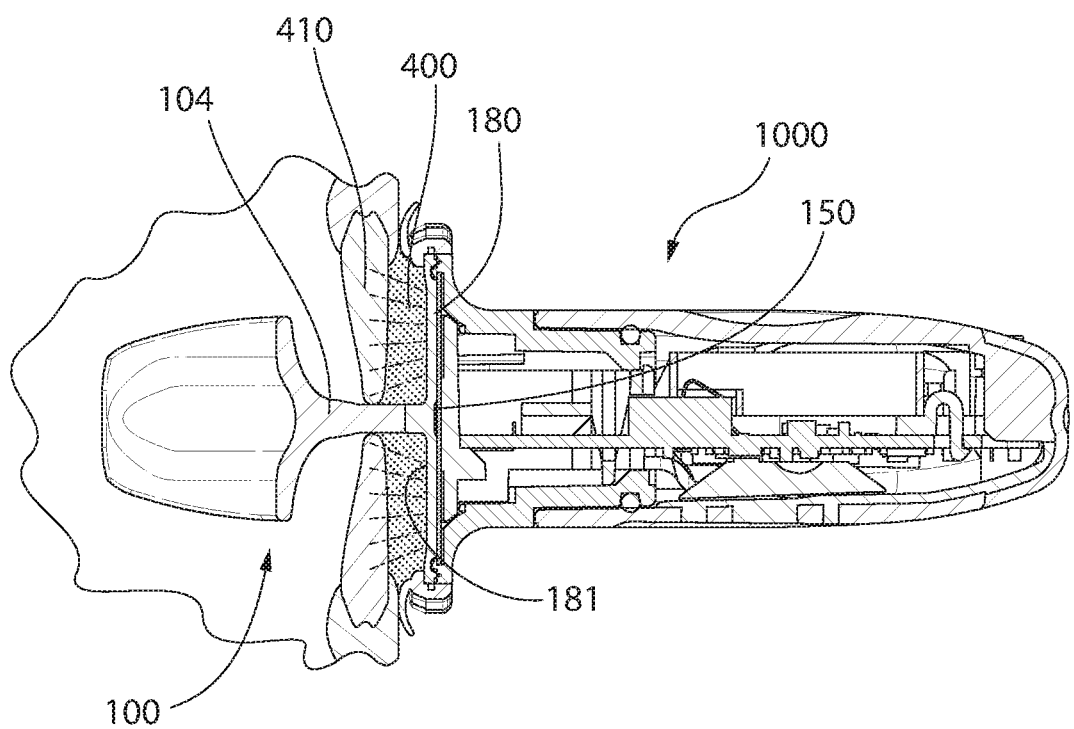
FIG. 29 is the schematic cross-sectional view of FIG. 28 with the oral treatment device powered on and emitting electromagnetic radiation.

Finally, as shown in FIG. 29, the next step is to activate the lamp 150, which can be achieved by pressing a button, sliding a switch, or the like as has been described herein.

Activation of the lamp 150 will cause the light emitters of the lamp 150 to generate electromagnetic radiation or light that passes through the lamp lens plate 159, the lens plate 180, and the teeth whitening material 400. As should be understood, the light will pass through the lamp lens plate 159, the lens plate 180, and the teeth whitening material 400 sequentially.

As can be seen in FIGS. 28 and 29, the lamp 150 and the lens plate 180 are oriented vertically when the mouthpiece 100 or portions thereof are located within a user's oral cavity. Thus, the lamp 150 and the lens plate 180 are not angled, but rather they are oriented so as to be perpendicular to the horizon or to the bite plate 104. Of course, the lamp 150 and the lens plate 180 could be positioned at other orientations in other embodiments if so desired.

As noted above, the oral treatment device 1000 may include a timer that is operably coupled to a processor. A single treatment using the oral treatment device 1000 may have a predetermined treatment time, and thus the oral treatment device 1000 may automatically power off upon the predetermined treatment time being reached or the oral treatment device 1000 may include an indicator to indicate to the user that the predetermined treatment time has been reached. Such an indicator could be a light, a sound (emitted by a speaker), a vibration (emitted by a vibration device), or the like. In some embodiments, the oral treatment device 1000 may be configured to activate an indicator at the halfway point during a treatment session. Thus, if a treatment is intended to last for ten minutes, the indicator may be automatically activated at the expiration of five minutes from the beginning of the treatment time (determined either by the power being activated or by the power being activated and sensing that the mouthpiece 100 is located within a user's oral cavity). The indicator may be an audible tone, a visible light (blinking or the like) or a vibration or other tactile indicator. In some embodiments, the oral treatment device 1000 may emit an audible tone at the halfway point of a treatment session and again at the end of a treatment session/cycle. Of course, the audible tone may readily be replaced by emission of a light or a tactile indicator as described herein. In certain embodiments, the oral treatment device 1000 may include a speaker located inside of the handle 300 to emit the audible tone.

In some embodiments, the speaker may also emit an audible tone, for example three distinct tones or the like, if the battery runs out of power during a treatment session. Thus, the speaker may emit a first audible tone at the halfway point during a treatment session, a second audible tone at the end of a treatment session, and a third audible tone if the battery runs out of power during a treatment session. The first and second audible tones may be the same in some embodiments and they may be different in other embodiments (e.g., the first audible tone could be a single discrete beep and the second audible tone could be two discrete beeps, or the first and second audible tones could have a first sound pattern and the third audible tone could have a second different sound pattern). In some embodiments, the first and second audible tones may be different from one another and from the third audible tone so that a user can readily distinguish between the different tones so that the user understands the information that the oral treatment device 1000 is trying to relay to the user.

The oral treatment device 1000 may in certain embodiments be sold as a kit that includes the mouthpiece/housing and a supply of the tooth whitening material 400. In other embodiments the mouthpiece/housing may be sold by itself without tooth whitening material. Furthermore, in certain embodiments the mouthpiece/housing may be designed and used to dispense the tooth whitening material into contact with the user's teeth. Thus, there is versatility in the use of the devices and systems described herein. Furthermore, it should be appreciated that when the device is used for both dispensing the tooth whitening material and emitting electromagnetic radiation onto the user's teeth, the tooth whitening material may be optically clear to enable the electromagnetic radiation to be transmitted through the tooth whitening material and onto the surfaces of the user's teeth.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the spirit and scope of the invention should be construed broadly as set forth in the appended claims.

What is claimed is:

1. An oral treatment device comprising:
   a control circuit that comprises, in operable coupling, a power source, a first compressible electrical contact having a first electrical charge, and a second compressible electrical contact having a second electrical charge that is opposite the first electrical charge;
   an intraoral mouthpiece comprising:
      a lamp comprising a lamp longitudinal axis and a flexible sheet body having first and second electrical contacts located on the lamp longitudinal axis, the lamp longitudinal axis extending from a first lamp side edge of the flexible sheet body to a second lamp side edge of the flexible sheet body, the lamp configured to generate and emit electromagnetic radiation from a front surface of the lamp;
      wherein the lamp is mounted within the oral treatment device so that the first and second electrical contacts of the lamp are aligned and pressed into contact with the first and second compressible electrical contacts of the control circuit, respectively; and
      wherein a transverse plane contains the lamp longitudinal axis and the transverse plane intersects both of the first and second electrical contacts of the lamp and both of the first and second compressible electrical contacts.

2. The oral care treatment device according to claim 1 wherein the first and second compressible electrical contacts of the control circuit are in a compressed state due to the contact with the first and second electrical contacts of the lamp.

3. The oral care treatment device according to claim 1 wherein each of the first and second compressible electrical contacts comprises a body formed of a compressible material and an electrically conductive layer on the compressible material.

4. The oral care treatment device according to claim 1 wherein each of the first and second compressible electrical contacts comprises an electrically conductive mesh filled with a compressible material.

5. The oral care treatment device according to claim 3 wherein the compressible material is a foam.

6. The oral care treatment device according to claim 1 wherein the first and second compressible electrical contacts are resilient.

7. The oral care treatment device according to claim 1 further comprising:
   the intraoral mouthpiece comprising:
   a lamp support surface having a concave curvature, the lamp mounted to the lamp support surface;
   a curved lens plate overlying a front surface of the flexible sheet body of the lamp, the lamp positioned between the curved lens plate and the lamp support surface, the lens plate comprising one or more protuberances extending from a convex rear surface of the curved lens plate that are aligned with the first and second electrical contacts of the lamp and press the flexible sheet body of the lamp against the first and second compressible electrical contacts to electrically couple the first and second electrical contacts of the lamp with the first and second compressible electrical contacts, respectively.

8. The oral care treatment device according to claim 7 wherein the one or more protuberances compress the first and second compressible electrical contacts between a wall surface and the flexible sheet body.

9. The oral care treatment device according to claim 8 wherein the lamp support surface comprises at least one depression, the wall surface forming a floor surface of the at least one depression.

10. The oral care treatment device according to claim 7 wherein the intraoral mouthpiece comprises a lamp support structure comprising a curved support plate that comprises at least a portion of the lamp support surface.

11. The oral care treatment device according to claim 10 wherein the lamp support structure comprises a perimetric lamp retaining wall protruding from and surrounding the lamp support surface, the lamp positioned against the lamp support surface so that edges of the flexible sheet body of the lamp are retained by the perimetric lamp retaining wall.

12. The oral care treatment device according to claim 10 wherein the intraoral mouthpiece further comprises a guard component formed of an elastomeric material, the guard component coupled to the lamp support structure and sealing the lamp in a fluid tight manner between the curved lens plate the lamp support structure, the guard component comprising a frame portion defining a window through which the curved lens plate is exposed and the electromagnetic radiation emitted by the lamp can pass.

13. The oral care treatment device according to claim 12 wherein the curved lens plate comprises one or more protuberances extending from a concave front surface of the curved lens plate and into a bite plate of the guard component that divides the window into an upper window and a lower window.

14. The oral care treatment device according to claim 10 wherein the curved lens plate comprises one or more alignment elements that mechanically mate with one or more alignment elements of the lamp support structure to maintain the curved lens plate and the lamp support structure in relative alignment with one another.

15. The oral care treatment device according to claim 7 wherein in an uncompressed state, each of the first and second compressible electrical contacts protrude from the lamp support surface.

16. The oral care treatment device according to claim 7 further comprising:
   the flexible sheet body of the lamp comprising at least one upper illumination zone located on the front surface of the flexible sheet body of the lamp above the lamp longitudinal axis and at least one lower illumination zone on the front surface of the flexible sheet body of the lamp located below the lamp longitudinal axis; and
   the one or more protuberances contacting the front surface of the flexible sheet body between the at least one upper illumination zone and the at least one lower illumination zone.

17. The oral care treatment device according to claim 1 wherein the first and second compressible electrical contacts are compressed into a compressed state between a wall surface and the first and second electrical contacts of the lamp.

18. The oral care treatment device according to claim 1 wherein the lamp further comprises a plurality of light emitters embedded within the flexible sheet body that generate light which is emitted from the front surface of the flexible sheet body; and wherein the plurality of light emitters are light emitting diodes printed with an electrically conductive ink.

19. The oral treatment device according to claim 1 wherein the lamp is configured to emit light at a wavelength, or wavelengths, effective to whiten teeth.

20. An oral treatment device comprising:
   a control circuit that comprises, in operable coupling, a power source, a first electrical contact having a first electrical charge, and a second electrical contact having a second electrical charge that is opposite the first electrical charge;
   an intraoral mouthpiece comprising:
   a lamp comprising a flexible sheet body and a plurality of light emitters, the flexible sheet body having first and second electrical contacts;
   a lamp support structure comprising a lamp support surface having a concave curvature, the lamp mounted to the lamp support surface;
   a curved cover lens plate overlying the lamp, the lamp positioned between the curved cover lens plate and the lamp support surface, the curved cover lens plate comprising one or more protuberances extending from a convex rear surface of the curved cover lens plate that are aligned with the first and second electrical contacts of the lamp and press the flexible sheet body of the lamp against the first and second electrical contacts of the control circuit.

21. The oral treatment device according to claim 20 wherein the curved cover lens plate comprises one or more alignment elements that mechanically mate with one or more alignment elements of the lamp support structure to maintain the curved cover lens plate and the lamp support structure in relative alignment with one another.

22. The oral care treatment device according to claim 20 wherein the curved cover lens plate comprises one or more protuberances extending from a concave front surface of the curved cover lens plate and into a bite plate.

23. The oral care treatment device according to claim 22 wherein the intraoral mouthpiece further comprises a guard component formed of an elastomeric material, the guard component coupled to the lamp support structure and sealing the lamp in a fluid tight manner between the curved cover lens plate and the lamp support structure, the guard component comprising a frame portion defining a window through which the curved cover lens plate is exposed and the bite plate, the bite plate dividing the window into an upper window that is aligned and a lower window.

24. The oral care treatment device according to claim 22 wherein the one or more protuberances extending from the concave front surface of the curved cover lens plate are aligned with the one or more protuberances extending from the convex rear surface of the curved cover lens plate.

25. The oral care treatment device according to claim 20 further comprising:
- the lamp extending along a lamp longitudinal axis that extends from a first lamp side edge of the flexible sheet body to a second lamp side edge of the flexible sheet body;
- the flexible sheet body of the lamp comprising at least one upper illumination zone located on the front surface of the flexible sheet body of the lamp above the lamp longitudinal axis and at least one lower illumination zone on the front surface of the flexible sheet body of the lamp located below the lamp longitudinal axis; and
- the first and second electrical contacts of the lamp located along the lamp longitudinal axis, the one or more protuberances contacting the flexible sheet body between the at least one upper illumination zone and the at least one lower illumination zone.

\* \* \* \* \*